United States Patent
Chen et al.

(10) Patent No.: US 11,840,570 B2
(45) Date of Patent: Dec. 12, 2023

(54) PHARMACEUTICAL COMBINATION AND METHOD FOR REGULATION OF TUMOR MICROENVIRONMENT AND IMMUNOTHERAPY

(71) Applicant: Great Novel Therapeutics Biotech & Medicals Corporation, Taipei (TW)

(72) Inventors: Jia-Shiong Chen, Taipei (TW); Ye-Su Chao, Taipei (TW); Chia-Nan Chen, Taipei (TW)

(73) Assignee: Great Novel Therapeutics Biotech & Medicals Corporation, Taipei (TW)

( * ) Notice: Subject to any disclaimer, the term of this patent is extended or adjusted under 35 U.S.C. 154(b) by 273 days.

(21) Appl. No.: 16/240,081

(22) Filed: Jan. 4, 2019

(65) Prior Publication Data

US 2019/0211103 A1    Jul. 11, 2019

Related U.S. Application Data

(60) Provisional application No. 62/614,306, filed on Jan. 5, 2018.

(51) Int. Cl.
```
C07K 16/28      (2006.01)
A61K 45/06      (2006.01)
A61K 31/155     (2006.01)
A61P 35/00      (2006.01)
A61K 31/506     (2006.01)
A61K 31/192     (2006.01)
A61K 31/616     (2006.01)
A61K 39/395     (2006.01)
A61K 31/415     (2006.01)
A61K 31/405     (2006.01)
A61K 31/4406    (2006.01)
A61P 37/04      (2006.01)
A61K 39/00      (2006.01)
```

(52) U.S. Cl.
CPC ........ *C07K 16/2827* (2013.01); *A61K 31/155* (2013.01); *A61K 31/192* (2013.01); *A61K 31/405* (2013.01); *A61K 31/415* (2013.01); *A61K 31/4406* (2013.01); *A61K 31/506* (2013.01); *A61K 31/616* (2013.01); *A61K 39/3955* (2013.01); *A61K 39/39558* (2013.01); *A61K 45/06* (2013.01); *A61P 35/00* (2018.01); *A61P 37/04* (2018.01); *C07K 16/2818* (2013.01); *A61K 2039/505* (2013.01); *A61K 2039/545* (2013.01); *C07K 2317/76* (2013.01)

(58) Field of Classification Search
CPC ... C07K 16/2827; A61P 37/04; A61K 31/155; A61K 31/4406
See application file for complete search history.

(56) References Cited

U.S. PATENT DOCUMENTS

| | | | |
|---|---|---|---|
| 2008/0207724 A1 | 8/2008 | Mink et al. | |
| 2014/0341989 A1 | 11/2014 | Loury et al. | |
| 2017/0231929 A1* | 8/2017 | Udono | A61K 39/0011 424/134.1 |
| 2017/0239297 A1 | 8/2017 | Gunther et al. | |
| 2017/0327582 A1* | 11/2017 | Bissonnette | A61K 31/167 |
| 2018/0021378 A1 | 1/2018 | Kang et al. | |
| 2018/0244783 A1 | 8/2018 | Hoey et al. | |
| 2018/0355042 A1 | 12/2018 | Bissonnette et al. | |
| 2021/0069163 A1* | 3/2021 | Chen | C07K 16/2827 |

FOREIGN PATENT DOCUMENTS

| | | |
|---|---|---|
| EP | 1743654 A1 | 1/2007 |
| EP | 3415908 A1 | 12/2018 |
| KR | 20170100653 | 9/2017 |
| RU | 2609833 C2 | 2/2017 |
| WO | 2007009539 A2 | 1/2007 |
| WO | 2017/035453 A1 | 3/2017 |
| WO | 2017/120591 A1 | 7/2017 |
| WO | 2017/132536 A1 | 8/2017 |
| WO | 2017/197140 A1 | 11/2017 |

OTHER PUBLICATIONS

North GL, Celecoxib as adjunctive therapy for treatment of colorectal cancer, The Annals of Pharmacotherapy, 35, 1638-1643 (Year: 2001).*
Tannock IF, The Basic Science of Oncology, Chapter 19, 338-359, edited by Tannock and Hill, (Year: 1992).*
Chidamide: https://pubchem.ncbi.nlm.nih.gov/compound/Chidamide#section=2D-Structure (Year: 2022).*
Entinostat: https://pubchem.nlm.nih.gov/compound/4261#section=2D-Structure (Year: 2022).*
Mocetinostat: https://pubchem.ncbi.nlm.nih.gov/compound/9865515#section=2D-Structure (Year: 2022).*
Romidepsin: https://pubchem.ncbi.nlm.nih.gov/compound/5352062#section=2D-Structure (Year: 2022).*
Nivolumab: https://www.cancer.gov/about-cancer/treatment/drugs/nivolumab (Year: 2022).*
Li et al., Hydrogel dual delivered celecoxib and anti-PD-1 synergistically improve antitumor immunity, Oncoimmunology, vol. 5, No. 2, e1074374 (Year: 2016).*
Nivolumab (retrieved from: https://www.cancer.gov/about-cancer/treatment/drugs/nivolumab) (Year: 2022).*
Office Action in counterpart Russia Application No. 2019100078, dated Aug. 21, 2019, in 6 pages; English translation provided.
McCaw, Tyler R., et al. "Modulation of antitumor immunity with histone deacetylase inhibitors." Immunotherapy 9.16 (2017): 1359-1372.
Hussain, Muzammal, et al. "Non-steroidal anti-inflammatory drugs, tumour immunity and immunotherapy." Pharmacological Research 66.1 (2012): 7-18.

(Continued)

*Primary Examiner* — Peter J Reddig
*Assistant Examiner* — Cheng Lu
(74) *Attorney, Agent, or Firm* — Prosyla Group PC

(57) ABSTRACT

The invention relates to a method of removing immune suppression in a tumor microenvironment or stimulating an immune system against cancer cells, comprising administering to a subject a combination of a HDAC inhibitor and an NSAID in combination with an immune checkpoint inhibitor.

7 Claims, 89 Drawing Sheets

(56) References Cited

OTHER PUBLICATIONS

Wang, Xiao, Susana Peralta, and Carlos T. Moraes. "Mitochondrial alterations during carcinogenesis: a review of metabolic transformation and targets for anticancer treatments." Advances in Cancer Research. vol. 119. Academic Press, 2013. 127-160; abstract found on Aug. 21, 2019 at https://www.Sciencedirect.Com/topics/medicine-and-dentistry/tumor-microenvironment.
GenBank Q9NZQ7.1 Full=Programmed cell death 1 ligand 1; available at https://www.ncbi.nlm.nih.gov/protein/q9nzq7, 8 pages.
Office Action in counterpart Israel Application No. 264068, dated Nov. 12, 2020, in 3 pages; English transaltion provided.
Hamada, Tsuyoshi, Marios Giannakis, and Shuji Ogino. "Aspirin in the era of immunotherapy." Oncotarget 8.43 (2017): 73370-73371.
Johnpulle, Romany Anne Nilanthi, et al. "Cyclooxygenase inhibition and response to anti-PD1/L1 in advanced melanoma." Journal of Clinical Oncology (2016): 34:15_suppl, e21023, 2 pages.
Office Action in counterpart Taiwan Application No. 108100337, dated Oct. 8, 2019, in 14 pages; English translation provided.
Scharping, Nicole E., et al. "Efficacy of PD-1 blockade is potentiated by metformin-induced reduction of tumor hypoxia." Cancer Immunology Research 5.1 (Jan. 2017): 9-16; Published Online Dec. 9, 2016; DOI: 10.1158/2326-6066.CIR-16-0103.
Office Action in counterpart Russia Application No. 2019100078, dated Apr. 15, 2020, in 6 pages; English translation provided.
A. Ju. Sidullin et al., Pharmaceutical incompatibility at a combination of various drugs in infusion therapy, Medical Practice (published on Oct. 18, 2013), 4 pages; English translation of Abstract provided.
Korea Office Action in KR Counterpart Application No. 10-2019-0000807, dated May 14, 2020, in 5 pages; English translation provided.
Office Action in counterpart China Application No. 201910008912.6, dated Nov. 30, 2020, in 15 pages; English translation provided.
Terranova-Barberio, Manuela, et al. "HDAC inhibition potentiates immunotherapy in triple negative breast cancer." Oncotarget 8.69 (2017): 114156.
Hamada, Tsuyoshi, et al. "Aspirin use and colorectal cancer survival according to tumor CD274 (programmed cell death 1 ligand 1) expression status." Journal of Clinical Oncology 35.16 (2017): 1836.
Extended European Search Report in counterpart European Application No. 19150392.9, dated Jun. 5, 2019, in 8 pages.
Roberta Mazzone et al: "Epi-drugs in combination with immunotherapy: a new avenue to improve anticancer efficacy", Clinical Epigenetics, Biomed Central Ltd, GB, vol. 9, No. 1, May 30, 2017, pp. 1-15.
Briere David et al: "The class I/IV HDAC inhibitor mocetinostat increases tumor antigen presentation, decreases immune suppressive cell types and augments checkpoint inhibitor therapy", Cancer Immunology, Immunotherapy, Springer, Berlin/Heidelberg, vol. 67, No. 3, Nov. 9, 2017, pp. 381-392.
Office Action in counterpart New Zealand Application No. 749727, dated Jul. 12, 2019, in 4 pages.
Zelenay, S., et al. (2015). Cyclooxygenase-Dependent Tumor Growth through Evasion of Immunity. Cell, 162, pp. 1257-1270.
Peulen, O., et al. (2013). The Anti-Tumor Effect of HDAC Inhibition in a Human Pancreas Cancer Model Is Significantly Improved by the Simultaneous Inhibition of Cyclooxygenase 2. PLOS ONE, 8(9), e75102, 12 pages.
Japan Office Action in JP Counterpart Application No. 2019-000290, dated Mar. 10, 2020, in 4 pages; machine English translation provided.
Li, Xiaofei, et al. "Synergistically killing activity of aspirin and histone deacetylase inhibitor valproic acid (VPA) on hepatocellular cancer cells." Biochemical and Biophysical Research Communications 436.2 (2013): 259-264.
Zhang, J., et al., "PD-1/PD-L1 Based Combinational Cancer Therapy: Icing on the Cake," Front. Pharmacol. 11:722. doi: 10.3389/fphar.2020.00722.
Toriyama, S., et al., "A Histone Deacetylase Inhibitor, OBP-801, and Celecoxib Synergistically Inhibit the Cell Growth with Apoptosis via a DR5-Dependent Pathway in Bladder Cancer Cells," Molecular Cancer Therapeutics, Published Online First Jul. 12, 2016; DOI: 10.1158/1535-7163. MCT-16-0010; 2066 Mol Cancer Ther; 15(9) Sep. 2016.
Zhang, G., et al., "Synergistic antitumor effects of the combined treatment with an HDAC6 inhibitor and a COX-2 inhibitor through activation of PTEN," Oncology Reports 38: 2657-2666, 2017.
Twomey, Julianne D. and Zhang, Baolin, "Cancer Immunotherapy Update: FDA-Approved Checkpoint Inhibitors and Companion Diagnostics," AAPS Journal, 2021, vol. 23, No. 39, pp. 1-11.
Vaddepally, Ruju K. et al., "Review of Indications of FDA-Approved Immune Checkpoint Inhibitors per NCCN Guidelines with the Level of Evidence," Cancers, 2020, vol. 17, No. 738, pp. 1-19.

* cited by examiner

PD: ≥ 5 fold initial GR
SD: 2-5 fold initial GR
PR: ≤ 2 fold initial GR

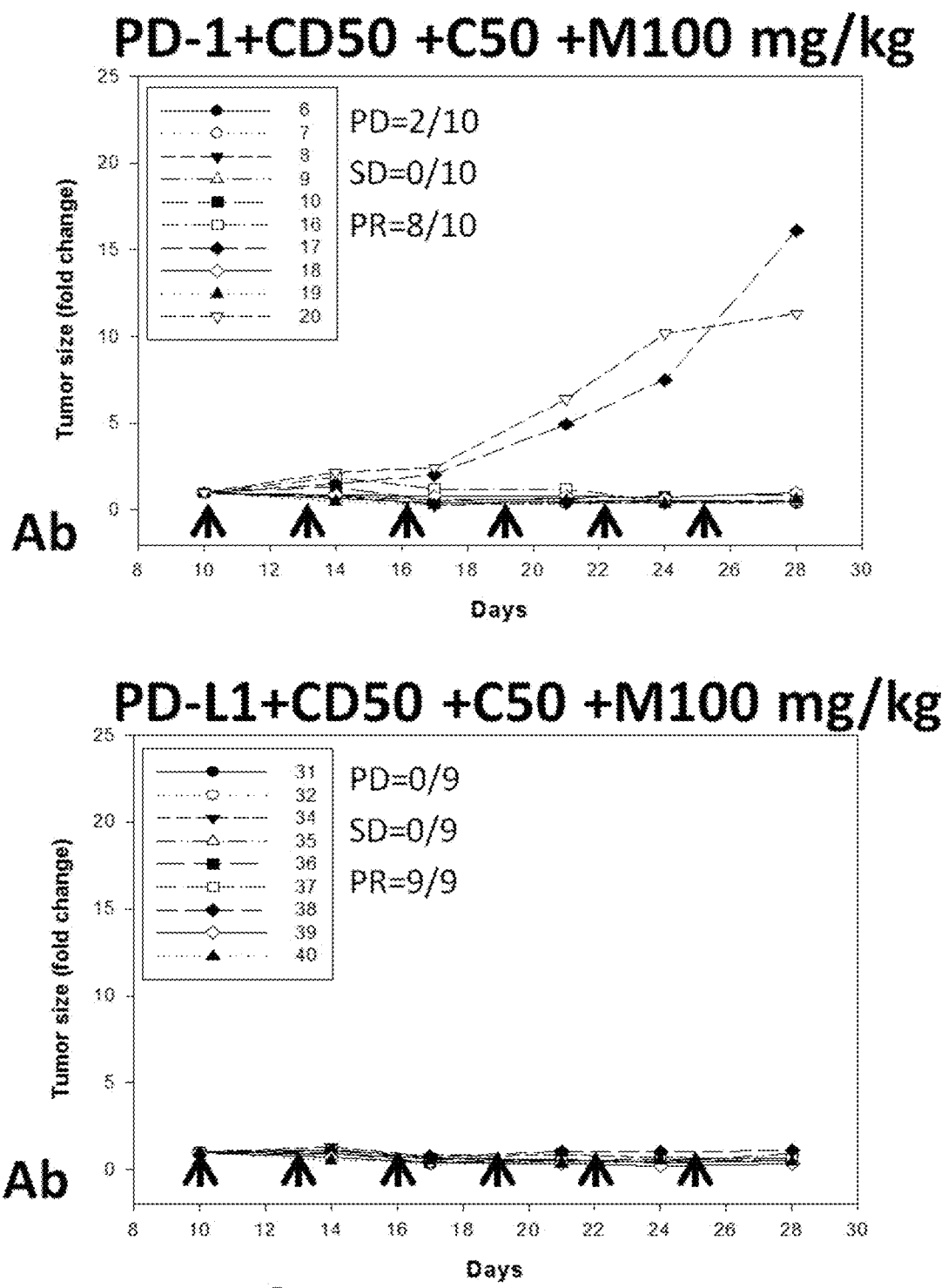

Nude mice

PHARMACEUTICAL COMBINATION AND METHOD FOR REGULATION OF TUMOR MICROENVIRONMENT AND IMMUNOTHERAPY

FIELD OF THE INVENTION

The present invention relates to immunotherapy. Particularly, the present invention provides a pharmaceutical combination and its applications in regulating tumor microenvironment and cancer immunotherapy.

BACKGROUND OF THE INVENTION

Cancer immune therapy is a rapidly developing field that has yielded impressive and promising breakthroughs. The discovery of the existence of tumor associated antigens has now raised the possibility of using a host's immune system to intervene in tumor growth. Various mechanisms of harnessing both the humoral and cellular arms of the immune system are currently being explored for cancer immunotherapy.

Several strategies have been proposed to break immune tolerance including adoptive transfer of immune effectors, immunomodulatory therapy, and vaccination. But, these strategies still do not prevent immune escape. The main escape pathway occurs in cancer cells including anti-apoptotic signaling, mitogen-activated protein kinase (MAPK), and cyclic adenosine monophosphate (cAMP) related mechanisms. The tumor microenvironment is an important field of research because it is dynamic based on tumor progression. Tumors evolve mechanisms to escape immune control by a process called immune editing, which provides a selective pressure in the tumor microenvironment that can lead to malignant progression. In the tumor-promoting phase referred to as 'immune escape', the immune system can further tumor progression either by selecting cancer cells that are more capable of surviving the host's immunocompetence or by modifying the tumor microenvironment in such a way that tumor outgrowth is facilitated.

Immune system homeostasis includes the presence of both stimulatory and inhibitory mechanisms to control the balance in immune system response. The inhibitory mechanisms include cytotoxic T lymphocyte associated antigen-4 (CTLA-4, a CD28 homolog), and programmed cell death protein-1 (PD-1) or its ligand (PD-L1), TIM-3 (T cell immunoglobulin-3), BTLA (B and T lymphocyte attenuator), VISTA (V-domain Ig suppressor of T cell activation) and LAG-3 (lymphocyte-activation gene 3). Currently, many immune checkpoint inhibitors monoclonal antibodies including anti-CTLA-4, anti-PD-1, and anti-PD-L1 antibodies have been approved by the US FDA and EMA for therapeutic use in several oncological indications. However, for these immune checkpoint inhibitors, about 20%-30% cancer patients have provided tumor response for monotherapy. The efficacy is still unsatisfactory.

US 20180244783 provides Wnt pathway inhibitors in combination with immunotherapeutic agents for the treatment of cancer and other diseases. US 20180355042 provides combinations that include an HDACi and a PD-1 inhibitor that are useful for treating cancer, including reducing and/or preventing cancer metastasis. However, there is still a need to develop a therapeutic solution to achieve more pronounced antitumor activity.

SUMMARY OF THE INVENTION

The present invention surprisingly found that the combination of a histone deacetylase (HDAC) inhibitor and a nonsteroidal anti-inflammatory drugs (NSAIDs) can influence tumor microenvironment, suggesting that such combination in combination with an immune checkpoint inhibitors markedly improves anti-cancer activity. The present invention found that the treatment with the pharmaceutical combination combined with an immune checkpoint inhibitor significantly augments anti-cancer activity in comparison with the immune checkpoint inhibitor alone. Co-treatment with the pharmaceutical combination and an immune checkpoint inhibitor provides more potency in inhibiting tumor growth than with the HDAC inhibitor plus the immune checkpoint inhibitor. Furthermore, the combination of the pharmaceutical combination and an immune checkpoint inhibitor significantly eradicates the tumor and augments survival rate to about 70-80%.

In one embodiment, the present invention provides a method of removing immune suppression in a tumor microenvironment or stimulating an immune system against cancer cells, comprising administering to a subject a combination of an HDAC inhibitor and an NSAID in combination with an immune checkpoint inhibitor. The method can inhibit or treat a cancer through immunotherapy. In an embodiment, the amounts of the HDAC inhibitor and NSAID in the combination range from about 5% to about 40% (w/w) and about 5% to about 40% (w/w), respectively.

In a further embodiment, the combination further comprises a biguanide compound. The amount of biguanide compound ranges from about 40% to 80% (w/w).

In some embodiments, the HDAC inhibitor is a selective inhibitor of class I HDAC. Particularly, the HDAC inhibitor is a benzamide class of HDAC inhibitor. Certain embodiments of the HDAC inhibitor include chidamide, entinostat, vorinostat, romidepsin, panobinostat, belinostat, panobinostat, valproic acid, mocetinostat, abexinostat, entinostat, pracinostat, resminostat, givinostat and quisinostat.

In some embodiments, the NSAID is aspirin, ibuprofen, indomethacin, naproxen or a COX-2 inhibitor. Certain embodiments of the COX-2 inhibitor include celecoxib, rofecoxib and etoricoxib.

In some embodiments, the immune checkpoint inhibitor is an anti-CTLA-4 antibody, anti-PD-1 antibody or an anti-PD-L1 antibody. Certain embodiments of the immune checkpoint inhibitor include lambrolizumab, pidilizumab, nivolumab, durvalumab, avelumab, atezolizumab and MIHI.

Certain embodiments of the cancer include glioblastoma, liver cancer, colorectal carcinoma, glioblastoma, gastric cancer, colorectal cancer, esophageal cancer, lung cancer, pancreatic cancer, renal cell carcinoma, benign prostate hyperplasia, prostate cancer, ovarian cancer, melanoma, breast cancer, chronic lymphocytic leukemia (CLL), Merkel cell carcinoma, Non-Hodgkin lymphoma, acute myeloid leukemia (AML), gallbladder cancer, cholangiocarcinoma, urinary bladder cancer, and uterine cancer.

In one embodiment, the method further comprises administering one or more additional anti-cancer agents.

In one embodiment, the invention provides a pharmaceutical combination comprising an HDAC inhibitor, an NSAID and an immune checkpoint inhibitor. The embodiments of the HDAC inhibitor, the NSAID and the immune checkpoint inhibitor are those described herein. In one embodiment, the pharmaceutical combination further comprises a biguanide compound.

Figure 1A:
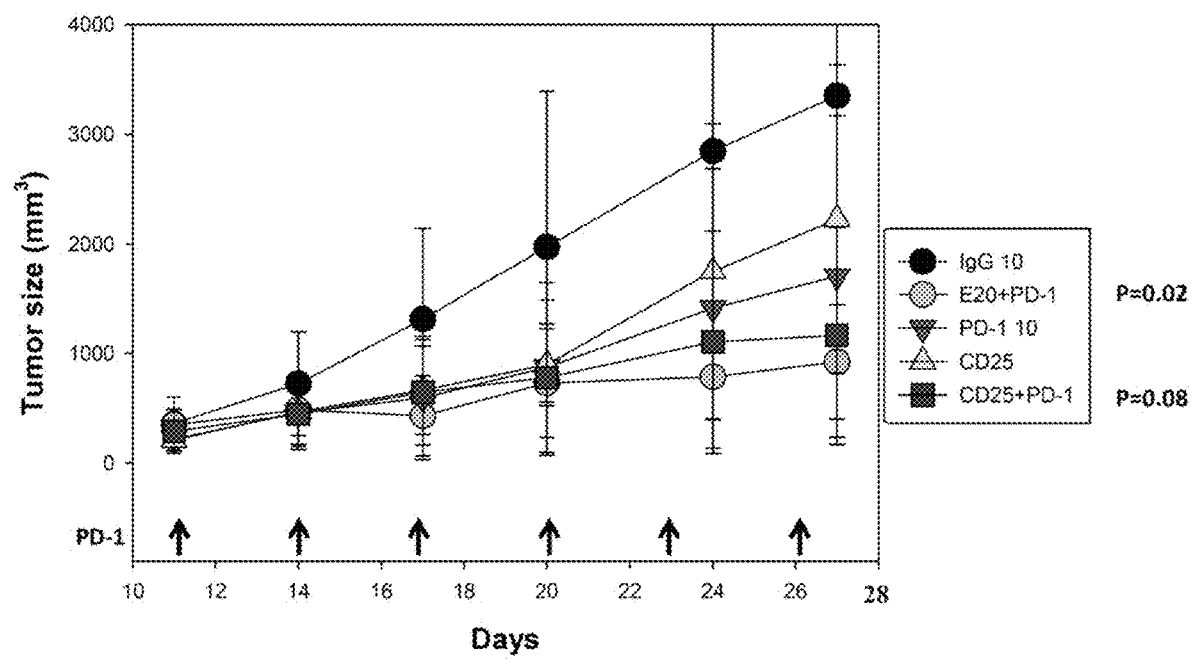
FIGS. 1 A to D show the therapeutic response of chidamide or entinostat combined with anti-PD-1 antibody in CT26 tumor-bearing mice. BALB/c mice bearing a CT26 colon tumor were treated with various therapeutic modalities as indicated. IgG, Anti-IgG control (vehicle, 10 mg/kg); PD-1, Anti-PD-1 monoclonal antibody (10 mg/kg); CD, chidamide (25 mg/kg); E, MS-275 (entinostat, 20 mg/kg). Total tumor volumes (A), individual tumor volumes (B), CT26 tumor bearing-mice body weight (C), and animal survival (D) were recorded. CT26 tumor bearing mice were treated as indicated and euthanized when tumor volume reached 3000 mm$^3$ after tumor implantation. Means and SDs are shown. The number of animals used in each experimental arm and P values are also indicated.*P<0.05. P-values were calculated using Student's t-test that compared tumor size at indication group with IgG group.

FIGS. 9 A to H show the therapeutic response of chidamide plus celecoxib at various dose regimens combined with anti-PD-1 antibody in CT26 tumor-bearing mice. BALB/c mice bearing a CT26 colon tumor were treated with various therapeutic modalities as indicated. IgG, Anti-IgG control (vehicle, 2.5 mg/kg); PD-1, Anti-PD-1 monoclonal antibody (2.5 mg/kg); CD, chidamide (12.5, 25 or 50 mg/kg); C, celecoxib (12.5, 25 or 50 mg/kg). The total tumor volumes after treatment with anti-PD-1 antibody combined with chidamide 12.5 mg/kg plus celecoxib at various doses (12.5, 25.0, or 50 mg/kg) (A), the total tumor volumes after treatment with anti-PD-1 antibody combined with chidamide 25 mg/kg plus celecoxib at various doses (12.5, 25.0, or 50 mg/kg) (B), the total tumor volumes after treatment with anti-PD-1 antibody combined with chidamide 50 mg/kg plus celecoxib at various doses (12.5, 25.0, or 50 mg/kg) (C), individual tumor volumes after treatment with various therapeutic modalities as indicated (D), CT26 tumor-bearing-mice body weight (E), and animal survival (F to H) were recorded. CT26 tumor bearing mice were treated as indicated and euthanized at tumor volume of 3,000 mm$^3$ after tumor implantation. Means and SDs are shown. The number of animals used in each experimental arm and P values are also indicated.*P<0.05. P-values were calculated using Student's t-test that compared tumor size at indication group with IgG group.

FIGS. 10 A to H show the therapeutic response of HDAC inhibitors (chidamide and mocetinostat) plus COX-2 inhibitors (celecoxib, aspirin, and ibuprofen) combined with anti-PD-1 or anti-CTLA-4 antibody in CT26 tumor-bearing mice. BALB/c mice bearing a CT26 colon tumor were treated with various therapeutic modalities as indicated. IgG, Anti-IgG control (vehicle, 2.5 mg/kg); PD-1, Anti-PD-1 monoclonal antibody (2.5 mg/kg); CTLA4: Anti-CTLA4 monoclonal antibody (2.5 mg/kg); CD, chidamide (50 mg/kg); Moc, mocetinostat (30 mg/kg); C, celecoxib (50 mg/kg); Asp, aspirin (50 mg/kg); Ibu, ibuprofen (50 mg/kg). The total tumor volumes after treatment with anti-PD-1 antibody combined with chidamide (50 mg/kg) plus COX-2 inhibitor (celecoxib 50 mg/kg, aspirin 50 mg/kg, or ibuprofen 50 mg/kg) compared to those of control groups (anti-PD-1 antibody alone and combination without anti-PD-1 antibody) (A), the total tumor volumes after treatment with anti-PD-1 antibody combined with celecoxib 50 mg/kg plus HDAC inhibitor (chidamide 50 mg/kg or mocetinostat 30 mg/kg) (B), the total tumor volumes after treatment with anti-CTLA4 or anti-PD-1 antibody combined with chidamide 50 mg/kg plus celecoxib 50 mg/kg (C), individual tumor volumes after treatment with various therapeutic modalities as indicated (D), CT26 tumor-bearing-mice body weight (E), and animal survival (F to H) were recorded. CT26 tumor bearing mice were treated as indicated and euthanized at tumor volume of 3,000 mm$^3$ after tumor implantation. Means and SDs are shown. The number of animals used in each experimental arm and P values are also indicated.*P<0.05. P-values were calculated using Student's t-test that compared tumor size at indication group with IgG group.

FIGS. 11 A to D confirm the therapeutic response of chidamide plus celecoxib at fixed dose combined with anti-PD-1 antibody in CT26 tumor-bearing mice. BALB/c mice bearing a CT26 colon tumor were treated with various therapeutic modalities as indicated. IgG, Anti-IgG control (vehicle, 2.5 mg/kg); PD-1, Anti-PD-1 monoclonal antibody (2.5 mg/kg); CD, chidamide (50 mg/kg); C, celecoxib (50 mg/kg). The total tumor volumes after treatment with chidamide plus celecoxib combined with or without anti-PD-1 antibody (A), individual tumor volumes after treatment with various therapeutic modalities as indicated (B), CT26 tumor-bearing-mice body weight (C), and animal survival (D) were recorded. CT26 tumor bearing mice were treated as indicated and euthanized at tumor volume of 3,000 mm$^3$ after tumor implantation. Means and SDs are shown. The number of animals were increased in each experimental arm and P values are also indicated.*P<0.05. P-values were calculated using Student's t-test that compared tumor size at indication group with IgG group.

FIGS. 12 A to E show the therapeutic response of chidamide plus metformin and celecoxib at fixed dose combined with anti-PD-L1 antibody in CT26 tumor-bearing nude mice. BALB/c nude mice bearing a CT26 colon tumor were treated with various therapeutic modalities as indicated. IgG, Anti-IgG control (vehicle, 2.5 mg/kg); PD-L1, Anti-PD-L1 monoclonal antibody (2.5 mg/kg); CD, chidamide (50 mg/kg); C, celecoxib (50 mg/kg); M, metformin (100 mg/kg). The total tumor volumes after treatment with anti-PD-L1 antibody combined with chidamide plus celecoxib and metformin compared to those of control groups (A), individual tumor volumes after treatment with various therapeutic modalities as indicated (B), CT26 tumor-bearing-mice body weight (C), tumor weight (D), and comparison of anti-tumor activities between normal and nude mice (E) were recorded.

FIGS. 13 A to F show the response of immune cells following treatment with anti-PD-1 antibody and chidamide combined with celecoxib. BALB/c mice bearing metastatic CT26 tumors were treated with the indicated therapeutic modalities, and FACS analyses were utilized to assess circulating and tumor-infiltrating immune cells. Means and SDs are shown, with P values indicated. IgG, Anti-IgG control (vehicle, 2.5 mg/kg); PD-1, Anti-PD-1 monoclonal antibody (2.5 mg/kg); CD, chidamide (50 mg/kg); C, celecoxib (50 mg/kg). FIG. 13A shows FACS results for CD4, CD8, PMN-MDSC, M-MDSC, and Treg cells. Representative FACS data showing percentages of Ly6G$^+$Ly6C$^{low}$ cells (PMN-MDSCs) and Ly6C$^+$Ly6G$^-$ cells (M-MDSCs) in CD45$^+$CD11b$^+$ gated circulating cells. Non-tumor-bearing mice n=6; Tumor-bearing mice n=11. FIG. 13B shows FACS results for circulating M-MDSC cells by indicated different therapeutic treatments in tumor-bearing mice, in comparison with the non-tumor-bearing mice. FIG. 13C shows FACS results for circulating Ly6C+Ly6G$^-$ cells (M-MDSCs) at day 12 correlated with corresponding tumor size at day 23 after indicated treatment in the mice as shown in FIG. 13B. FIG. 13D shows FACS results for circulating FoxP3+ Tregs cells by indicated treatment at day 8 and day 12. Representative FACS data show percentages of FoxP3 and CD25 double positive cells in circulating leukocytes. FIG. 13E shows FACS results for tumor-infiltrating myeloid (CD11b+), TAM, and M-MDSC cells by indicated treatment at day 8. FIG. 13F shows FACS results for tumor-infiltrating CD4+CD25+FoxP3+ Tregs, CD4+ T cells, and CD8+ T cells by indicated treatment at day 8. FIG. 13G shows the relative ratio of CD4+ T cells and Treg cells in tumor tissues from CT26 tumor-bearing mice after various treatments as examined by flow cytometric analysis. FIG. 13H shows the relative ratio of CD8+ T cells and Treg cells in tumor tissues from CT26 tumor-bearing mice after various treatments as examined by flow cytometric analysis. *P<0.05. Data assay for circulating immune cells in each group n=6, data assay for tumor-infiltrating immune cells in each group n=2.

DETAILED DESCRIPTION OF THE INVENTION

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference.

The term "a" and "an" refers to one or to more than one (i.e., to at least one) of the grammatical object of the article. By way of example, "an element" means one element or more than one element. The use of "or" means "and/or," unless specifically stated otherwise.

As used herein, "subject," "individual" and "patient" are used interchangeably to refer to a vertebrate, preferably a mammal, more preferably a human. Mammals include, but are not limited to, murines, simians, humans, farm animals, sport animals, and pets. Tissues, cells and their progeny of a biological entity obtained in vitro or cultured in vitro are also encompassed.

As used herein, "therapeutically effective amount" means an amount sufficient to treat a subject afflicted with a disease (e.g., a neurodegenerative disease) or to alleviate a symptom or a complication associated with the disease.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the term "immunotherapy" refers to the treatment of a subject afflicted with, or at risk of contracting or suffering a recurrence of, a disease by a method comprising inducing, enhancing, suppressing or otherwise modifying an immune response.

As used herein, the term "programmed cell death protein 1 (PD-1)" refers to an immunoinhibitory receptor belonging to the CD28 family PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863.

As used herein, the term "programmed death-ligand1 (PD-L1)" is one of two cell surface glycoprotein ligands for PD-1 (the other being PD-L2) that downregulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7.

As used herein, an "antibody" and "antigen-binding fragments thereof" encompass naturally occurring immunoglobulins (e.g., IgM, IgG, IgD, IgA, IgE, etc.) as well as non-naturally occurring immunoglobulins, including, for example, single chain antibodies, chimeric antibodies (e.g., humanized murine antibodies), heteroconjugate antibodies (e.g., bispecific antibodies), Fab', F(ab').sub.2, Fab, Fv, and rIgG. As used herein, an "antigen-binding fragment" is a portion of the full length antibody that retains the ability to specifically recognize the antigen, as well as various combinations of such portions.

As used herein, the term "cancer" refers to a broad group of various diseases characterized by the uncontrolled growth of abnormal cells in the body. Unregulated cell division and growth results in the formation of malignant tumors that invade neighboring tissues and can also metastasize to distant parts of the body through the lymphatic system or bloodstream. "Cancer" as used herein refers to primary, metastatic and recurrent cancers.

The present disclosure develops methods that focuses on the regulation of tumor microenvironment components, whereby removing immune suppression in a tumor microenvironment or stimulating an immune system against cancer cells. The tumor microenvironment is an important aspect of cancer biology that contributes to tumor initiation, tumor progression and responses to therapy. The tumor microenvironment is composed of a heterogeneous cell population that includes malignant cells and cells that support tumor proliferation, invasion, and metastatic potential though extensive crosstalk. Tumor cells often induce an immunosuppressive microenvironment, which favors the development of immunosuppressive populations of immune cells, such as myeloid-derived suppressor cells (MDSCs) and regulatory T cells (Tregs). Therefore, targets within the tumor microenvironment have been uncovered that can help direct and improve the actions of various cancer therapies, notably immunotherapies that work by potentiating host antitumor immune responses.

Accordingly, the first aspect of the present disclosure is to provide a method of removing immune suppression in a tumor microenvironment or stimulating an immune system against cancer cells, comprising administering to a subject a pharmaceutical combination of an HDAC inhibitor and an NSAID in combination with an immune checkpoint inhibitor. Alternatively, the present disclosure provides a use of a pharmaceutical combination of an HDAC inhibitor and an NSAID in the manufacture of a medicament for removing immune suppression in a tumor microenvironment or stimulating an immune system against cancer cells, wherein the pharmaceutical combination is administered in combination with an immune checkpoint inhibitor. Alternatively, the present disclosure provides a pharmaceutical combination for removing immune suppression in a tumor microenvironment or stimulating an immune system against cancer cells, wherein the pharmaceutical combination comprises an HDAC inhibitor and an NSAID and is administered in combination with an immune checkpoint inhibitor.

The second aspect of the present disclosure is to provide a pharmaceutical combination comprising an HDAC inhibitor, an NSAID and an immune checkpoint inhibitor.

In one embodiment, the amounts of the HDAC inhibitor, the NSAID such as COX-2 inhibitor and the immune checkpoint inhibitor in the pharmaceutical combination are about 10% to about 70% (w/w), about 10% to about 70% (w/w) and about 0.5% to about 20%, respectively.

In some embodiments, the amount of the HDAC inhibitor in the pharmaceutical combination ranges from about 20% (w/w) to about 70% (w/w), about 30% to about 70% (w/w), about 40% to about 70% (w/w), about 20% to about 60% (w/w), about 30% to about 60% (w/w), about 40% to about 60% (w/w) or about 35% to about 60% (w/w).

In some embodiments, the amount of the NSAID in the pharmaceutical combination ranges from about 20% to about 70% (w/w), about 30% to about 70% (w/w), about 40% to about 70% (w/w), about 20% to about 60% (w/w), about 30% to about 60% (w/w), about 40% to about 60% (w/w) or about 35% to about 60% (w/w).

HDACs have been shown to be involved in oncogenic transformation by mediated gene expression that influence the cell cycle progression, proliferation, and apoptosis. HDACs are investigated as possible treatment targets for cancers, parasitic and inflammatory diseases. Based on their homology of accessory domains to yeast histone deacetylases, the 18 currently known human histone deacetylases are classified into four groups (I-IV). Class I, which includes HDAC1, -2, -3 and -8 is related to yeast RPD3 gene; Class IIA includes HDAC4, -5, -7 and -9; Class IIB-6, and -10 is related to yeast Hdal gene; Class III, also known as the sirtuins is related to the Sir2 gene and includes SIRT1-7; and Class IV, which contains only HDAC11 has features of both Class I and II.

In one embodiment of the present disclosure, the HDAC inhibitor is a class I HDAC inhibitor. Preferably, the HDAC inhibitor is a selective inhibitor of class I HDACs. In some embodiments, the HDAC inhibitor is a benzamide class of histone deacetylase (HDAC) inhibitor. In some embodiments, the HDAC inhibitor includes, but is not limited to, chidamide, vorinostat, romidepsin, panobinostat, belinostat, panobinostat, valproic acid, mocetinostat, abexinostat, entinostat, pracinostat, resminostat, givinostat and quisinostat. In some embodiments, the HDAC inhibitor is chidamide, entinostat, or mocetinostat.

NSAID is a class of drugs that reduce pain, decrease fever, and, in higher doses, decrease inflammation. Most NSAIDs inhibit the activity of cyclooxygenase-1 (COX-1) and cyclooxygenase-2 (COX-2), and thereby the synthesis of thromboxanes and prostaglandins. It is thought that inhibiting COX-2 leads to the anti-inflammatory, analgesic and antipyretic effects, whereas those NSAIDs also inhibiting COX-1, particularly aspirin, may cause gastrointestinal bleeding and ulcers in large doses. COX-2 inhibitors are widely used to treat autoimmune and inflammatory diseases. Cyclooxygenase (COX), which has two isoforms, COX-1 and COX-2, is the enzyme responsible for the rate-determining step in the synthesis of bioactive lipids of prostanoids consisting of prostaglandin D2 (PGD2), PGE2, PGF2a, prostacyclin PGI2 and thromboxane TXA2. COX-1 is constitutively expressed in body tissues to maintain homeostatic prostanoids and involved in several biological functions such as angiogenesis, vasodilation, and tissue maintenance. However, COX-2 is expressed in low levels in normal condition. COX-2 is rapidly induced by stimuli such as infection, injury and pain to initiate pro-inflammatory processes. Selective COX-2 inhibitors are a type of non-steroidal anti-inflammatory drugs (NSAIDs).

In some embodiments, the NSAID includes, but is not limited to, aspirin, ibuprofen, indomethacin, naproxen and a COX-2 inhibitor. In some embodiments of the present invention, the NSAID is a COX2 inhibitor. In some embodiments, the COX2 inhibitor includes, but is not limited to, Celebrex (generic name is celecoxib), Rofecoxib and Etoricoxib. Preferably, the COX2 inhibitor is celecoxib.

In one embodiment, the immune checkpoint inhibitor can be used in combination with the pharmaceutical combination described herein to stimulate an immune system against cancer cells and treat a cancer Immune checkpoint inhibitors suitable for use in the present disclosure comprise an antagonist of an inhibitory receptor which inhibits the PD-1, CTLA-4, T cell immunoglobulin-3, B and T lymphocyte attenuator, V-domain Ig suppressor of T cell activation or lymphocyte-activation gene 3 pathway, such as anti-PD-1 antibodie, anti-PD-L1 antibodie, anti-CTLA-4 antibodies, anti-TIM-3 (T cell immunoglobulin-3) antibodies, anti-BTLA (B and T lymphocyte attenuator) antibodies, anti-VISTA (V-domain Ig suppressor of T cell activation) antibodies and anti-LAG-3 (lymphocyte-activation gene 3) antibodies. Examples of PD-1 or PD-L1 inhibitors include without limitation humanized antibodies blocking human PD-1 such as lambrolizumab (anti-PD-1 Ab, trade name Keytruda) or pidilizumab (anti-PD-1 Ab), Bavencio (anti-PD-L1 Ab, avelumab), Imfinzi (anti-PD-L1 Ab, durvalumab), and Tecentriq (anti-PD-L1 Ab, atezolizumab) as well as fully human antibodies such as nivolumab (anti-PD-1 Ab, trade name Opdivo) and cemiplimab-rwlc (anti-PD-1 Ab, trade name Libtayo). Other PD-1 inhibitors may include presentations of soluble PD-1 ligand including without limitation PD-L2 Fc fusion protein also known as B7-DC-Ig or AMP-244 and other PD-1 inhibitors presently under investigation and/or development for use in therapy. In addition, immune checkpoint inhibitors may include without limitation humanized or fully human antibodies blocking PD-L1 such as durvalumab and MIH1 and other PD-L1 inhibitors presently under investigation. In some embodiments, the amount of the immune checkpoint inhibitor ranges from about 0.5% (w/w) to about 15% (w/w), 0.5% (w/w) to about 10% (w/w), 0.5% (w/w) to about 5% (w/w), 1.0% (w/w) to about 20% (w/w), 1.0% (w/w) to about 15% (w/w), 1.0% (w/w) to about 10% (w/w) or 1.0% (w/w) to about 5% (w/w).

In one embodiment, the combination described herein further comprises a biguanide compound. In some embodiments, the amount of the biguanide compound ranges from about 30% to about 70% (w/w), about 30% to about 60% (w/w), about 30% to about 50% (w/w), about 50% to about 80% (w/w), about 60% to about 80% (w/w) or about 60% to about 70% (w/w), 40% to about 70% (w/w), about 40% to about 60% (w/w) or about 40% to about 50% (w/w).

Biguanide is an organic compound with the formula $HN(C(NH)NH_2)_2$. A variety of derivatives of biguanide are used as pharmaceutical drugs. The term "biguanidine" often refers specifically to a class of drugs that function as oral antihyperglycemic drugs used for diabetes mellitus or pre-diabetes treatment.

In some embodiment of the present disclosure, the biguanide compound includes, but is not limited to, metformin, phenformin, proguanil and chlorproguanil. Preferably, the biguanide compound is metformin.

In one embodiment, the pharmaceutical combination of an HDAC inhibitor and an NSAID is administered with the immune checkpoint inhibitor simultaneously or sequentially in either order or in alternation. In some embodiments of the present disclosure, the HDAC inhibitor, the NSAID, the immune checkpoint inhibitor and a biguanide compound are administered simultaneously. In some embodiments, the HDAC inhibitor, NSAID, the immune checkpoint inhibitor and the biguanide compound are administered sequentially in either order or in alternation.

In a further embodiment, the method further comprises administering one or more additional anti-cancer agents. The additional anti-cancer agent is any anti-cancer agent described herein or known in the art. In one embodiment, the additional anti-cancer agent is a chemotherapy or a platinum-based doublet chemotherapy. In certain embodiments, the additional anti-cancer agent is a tyrosine kinase inhibitor (TM). In one embodiment, the additional anti-cancer agent is an anti-VEGF antibody. In other embodiments, the anti-cancer agent is a platinum agent (e.g., cisplatin, carboplatin), a mitotic inhibitor (e.g., paclitaxel, albumin-bound paclitaxel, docetaxel, taxotere, docecad), a fluorinated Vinca alkaloid (e.g., vinflunine, javlor), vinorelbine, vinblastine, etoposide, or pemetrexed gemcitabin. In one embodiment, the additional anti-cancer agent is 5-flurouracil (5-FU). In certain embodiments, the additional anti-cancer agent is any other anti-cancer agent known in the art.

The pharmaceutical combination of the present invention may be formulated with a "carrier." As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. For example, the pharmaceutical combinations can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, lotion, gel, ointment, or a controlled-release patch or spray applied to the skin; (4) intravaginally or intrarectally, for example, as a pessary, cream, suppository or foam; (5) sublingually; (6) ocularly; (7) transdermally; (8) transmucosally; or (9) nasally.

In a further aspect, the present invention provides a method of treating a cancer in a subject, the method comprising administering a pharmaceutical combination of the invention to the subject.

In some embodiments, the cancer includes, but is not limited to, glioblastoma, liver cancer (such as hepatocellular carcinoma), colorectal carcinoma, glioblastoma, gastric cancer, colorectal cancer, esophageal cancer, lung cancer (such as non-small cell lung cancer (NSCLC) and small cell lung cancer), pancreatic cancer, renal cell carcinoma, benign prostate hyperplasia, prostate cancer, ovarian cancer, melanoma, breast cancer, chronic lymphocytic leukemia (CLL), Merkel cell carcinoma, Non-Hodgkin lymphoma, acute myeloid leukemia (AML), gallbladder cancer, cholangiocarcinoma, urinary bladder cancer, and uterine cancer.

In some embodiments, the pharmaceutical combination of the invention may be provided in a single formulation. In other embodiments, the pharmaceutical combination of the invention may be provided in separate formulations. A pharmaceutical combination may be formulated in a variety of and/or a plurality forms adapted to one or more preferred routes of administration. Thus, a pharmaceutical combination can be administered via one or more known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical combination, or a portion thereof, can be administered to a mucosal surface, such as by administration to, for example, the nasal or respiratory mucosa (e.g., by spray or aerosol). A pharmaceutical combination, or a portion thereof, also can be administered via a sustained or delayed release.

A formulation may be conveniently presented in unit dosage form and may be prepared by methods well known in the art of pharmacy. Methods of preparing a combination with a pharmaceutically acceptable carrier include the step of bringing the pharmaceutical combination of the invention into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

In some embodiments, the method can include administering a sufficient amount of the pharmaceutical combination to provide a dose of, for example, from about 10 mg/kg to about 1,000 mg/kg to the subject.

The present invention is illustrated by the following examples. It is to be understood that the particular examples, materials, amounts, and procedures are to be interpreted broadly in accordance with the scope and spirit of the invention as set forth herein.

EXAMPLES

Materials and Methods

Reagent.

Gibco RPMI 1640 and DMEM with L-glutamine were purchased from Invitrogen Life Technologies. HyClone FBS was purchased from Thermo Scientific. Chidamide was provided from GNTbm. Entinostat, mocetinostat, aspirin, ibuprofen, celecoxib and metformin were purchased from Cayman Chemical (Ann Arbor, Mich.). The following antibodies and reagents were used for animal experiments: mouse anti-PD-L1 (B7-H1) monoclonal antibody (10F.9G2; Bio X Cell), mouse anti-PD-1 (CD279) monoclonal antibody (RMP1-14; Bio X Cell), mouse anti-CTLA4 (CD152) monoclonal antibody (BE0164; Bio X Cell), and rat anti-IgG2a isotype control monoclonal antibody (2A3; Bio X Cell).

Cell Lines.

JC (CRL-2116; murine breast tumor cells) and CT26 (CRL-2638; murine colorectal adenocarcinoma) were purchased from ATCC. Both tumor cell lines were grown in McCoy's 5A supplemented with 10% (vol/vol) FBS at 37° C., 5% $CO_2$.

Anti-Cancer Activity in Animal Models.

Animal research was approved and overseen by The Taipei Medical University Institutional Animal Care and Use Committee (TMU IACUC). Six- to eight-wk-old male BALB/C mice (BioLASCO Taiwan) were used for all animal experiments. JC ($1 \times 10^7$), or CT26 ($5 \times 10^6 \sim 1 \times 10^7$) cancer cells were inoculated by s.c. into the right flank of each mouse. Tumors were allowed to grow for 11 d (tumor size about 200-300 mm$^3$) before randomization and treatment. CT26-bearing and JC-bearing mice were given 10 or 2.5 mg/kg of anti-IgG, anti-PD-1 and/or anti-PD-L1 and anti-CTLA-4 (2.5 mg/kg) antibodies i.p. on days 11, 14, 17, 20, 23, and 26 post-tumor implantation, and all antibodies were diluted to appropriate concentrations in 100 μL of sterile PBS (pH 7.4) (Invitrogen Life Technologies). Celecoxib, chidamide, metformin, mocetinostat, entinostat, aspirin, and ibuprofen treatments were administrated orally on day 11 post-tumor implantation. Daily treatment with celecoxib (12.5, 25.0, and 50 mg/kg) or metformin (100 or 200 mg/kg) was performed from days 11 to 26. Chidamide was administered to treat tumor bearing mice at doses of 6.25, 12.5, 25, and 50 mg/kg or as a single dose. Chidamide was orally administered daily from days 11 to 26. Entinostat was orally administered at a dose of 20 mg/kg every two days from days 11 to 25. Mocetinostat was orally administered at a dose of 30 mg/kg daily treatment from days 11 to 26. Aspirin and ibuprofen was orally administered at a dose of 50 mg/kg daily treatment from days 11 to 26. The anti-cancer activity was measured from the start of the treatment of tumor growth until the tumor volume reached 3,000 mm$^3$. Tumor volume was calculated as length×width$^2$×0.5.

Survival Rate in Animal Models.

The administration of antibody or drugs was performed from days 11 to 25 or 26. The tumor continued to grow in the tumor bearing mice. The tumor volume of the mice was measured once every three days. The tumor bearing mice were regarded as dead when the tumor volume reached 3,000 mm$^3$. All treatment groups were recorded and analyzed.

In Vivo Xenograft Experiment.

Animal research was approved and overseen by The Taipei Medical University Institutional Animal Care and Use Committee (TMU IACUC). Nude BALB/c mice (6 week old, female, 20 g body weight) were purchase from BioLASCO, Taiwan, and maintained under pathogen-free conditions. The mouse CT26 xenograft tumor model was developed by injecting 5×10$^6$ cells of a 150 μL CT26 cells. CT26 cancer cells were inoculated s.c. into the right flank of each mouse. Tumor cells were allowed to grow for 2 weeks once the tumor size reached 350-400 mm$^3$ before randomization and treatment. Nineteen nude mice were classified into five groups and treatment. Test animal received anti-IgG Ab 2.5 mg/kg as control, anti-PD-L1 Ab 2.5 mg/kg combined with chidamide 50 mg/kg plus celecoxib 50 mg/kg and metformin 100 mg/kg, chidamide 50 mg/kg combined with celecoxib 50 mg/kg and metformin 100 mg/kg, chidamide 50 mg/kg, and celecoxib 50 mg/kg. The treatment process was similar for all BALB/C mice. The anti-cancer activity was measured from the start of the treatment of tumor growth until day 29 to sacrifice and weighing the tumor. Tumor volume was calculated as length×width$^2$×0.5.

Flow Cytometry.

The following antibodies and reagents were used for flow cytometry: CD3 APC (17A2; Biolegend), CD4 PE (GK1.5; Biolegend), CD8a PerCP (53-6.7; Biolegend), CD25 PerCP (PC61; Biolegend), Foxp3 PE (MF-14; Biolegend), CD11b APC (M1/70; Biolegend), Ly-6C PerCP (HK1.4; Biolegend), Ly-6G PE (1A8; BioLegend), CD45 FITC (30-F11; Biolegend), MHCII (M5/114.15.2; eBioscience). Flow cytometry was performed with a BD FACSCalibur™ (BD Biosciences) and the data were analyzed with FACSDiva software (BD Biosciences). To assess the level of circulating myeloid derived suppressor cell (MDSC) population and lymphoid derived T cells, blood samples were collected from the mice day 8 and day 12 after initiation of the anti-PD-1 antibody (2.5 mg/kg) treatments with or without chidamide (50 mg/kg) plus celecoxib (50 mg/kg). One hundred and fifty microliters of blood was collected in an Eppendorf tube from either the right or left facial vein. RBCs from anticoagulated blood samples were immediately lysed using 2 mL of 1×BD FACS Lyse (BD Biosciences) for 3 min, and the samples were washed twice in ice-cold BD FACS Buffer (BD Biosciences). The samples were stained with the appropriate antibodies. For analysis, we used previously established phenotypic criteria of these cells as PMN-MDSC: CD45$^+$CD11b$^+$Ly6G$^+$Ly6C$^{low}$ cells, M-MDSC: CD45$^+$CD11b$^+$Ly6G$^-$Ly6C$^+$ cells, CD4$^+$ T-cells: CD45$^+$CD3$^+$CD4$^+$ cells, CD8$^+$ T-cells: CD45$^+$CD3$^+$CD8$^+$ cells, Treg cells: CD45$^+$CD3$^+$CD25$^+$ FOXP3$^+$ cells, TAM cells: CD45$^+$CD11b$^+$MHCII$^+$ cells and total CD45$^+$ cells were used as a common denominator. On the other hand, to assess the level of intratumoral CD8$^+$ and regulatory T-cell (Treg) populations, lymphocytes were first purified from tumor samples excised from mice day 8 after initiation of the anti-PD-1 antibody (2.5 mg/kg) treatments with or without chidamide (50 mg/kg) plus celecoxib (50 mg/kg). Briefly, primary tumor tissues were harvested, weighed, and minced to fine fragments. Mouse tumor Dissociation Kit (Cat: 130-096-730) was employed. The three enzymes were added to each sample at a ratio of 1 mL per 200 mg of tumor tissue. Samples were incubated on an end-over-end shaker for 120 min at 37° C. The resulting tissue homogenates were 0.4-μm filtered and washed three times in ice-cold PBS, and 1×10$^6$ cells per sample were used for antibody labeling. CD8$^+$ T-cell level was assessed using previously established phenotypic criteria of CD45$^+$CD3$^+$CD8$^+$, and total CD45$^+$CD3$^+$ cells were used as a common denominator. Treg cell level was assessed using previously established phenotypic criteria of CD45$^+$CD3$^+$CD25$^+$FOXP3$^+$, and total CD45$^+$CD3$^+$ cells were used as a common denominator.

Statistics. Means and standard errors were calculated for all data points from at least four independent experiments. Pairwise comparisons of tumor size between each of the experimental condition and the IgG control group were performed using a Student's two-sample t test (Systat Software, San Jose, Calif., USA).

Example 1 Effects of Anti-PD-1 Antibody

To understand the anti-cancer activity of anti-PD-1 antibody on the CT-26 colon cancer cell -bearing BALB/c mice, the anti-PD-1 antibody was administered into CT26-bearing mice at 10 mg/kg of anti-PD-1 and/or anti-IgG antibodies i.p. on days 11, 14, 17, 20, 23, and 26 of post tumor implantation. The experiment was started when tumor size grew to approximately 200-300 mm$^3$. The response rate was evaluated by several assays. In this study, we defined Partial Response (PR, 2 times tumor growth in the tumor bearing mice at the end of the treatment); Stable Disease (SD, between two and five times tumor growth in the tumor bearing mice at the end of the treatment); Progressive Disease (PD, equal to or greater than five times tumor growth in the tumor bearing mice at the end of the treatment). Normally, over ten to fifteen times tumor growth (about 3,000 mm$^3$) was found in the control group. Anti-PD-1 antibody significantly inhibited tumor growth in comparison with the control group (treated with anti-IgG group) (see FIG. 1A). When the tumor size of the control group reached approximately 3,000 mm$^3$, that of the anti-PD-1 antibody group grew to approximately 1,200 mm$^3$ (FIG. 1A). However, anti-PD-1 antibody only inhibited tumor growth for a short time; then the tumor continued to grow. In the anti-PD-1 antibody group, SD was observed in 3 mice and PD was observed in 3 mice (see FIG. 1B).

Example 2 Effects of Epigenetic Modulator Combined with Anti-PD-1 Antibody

Figure 1B:
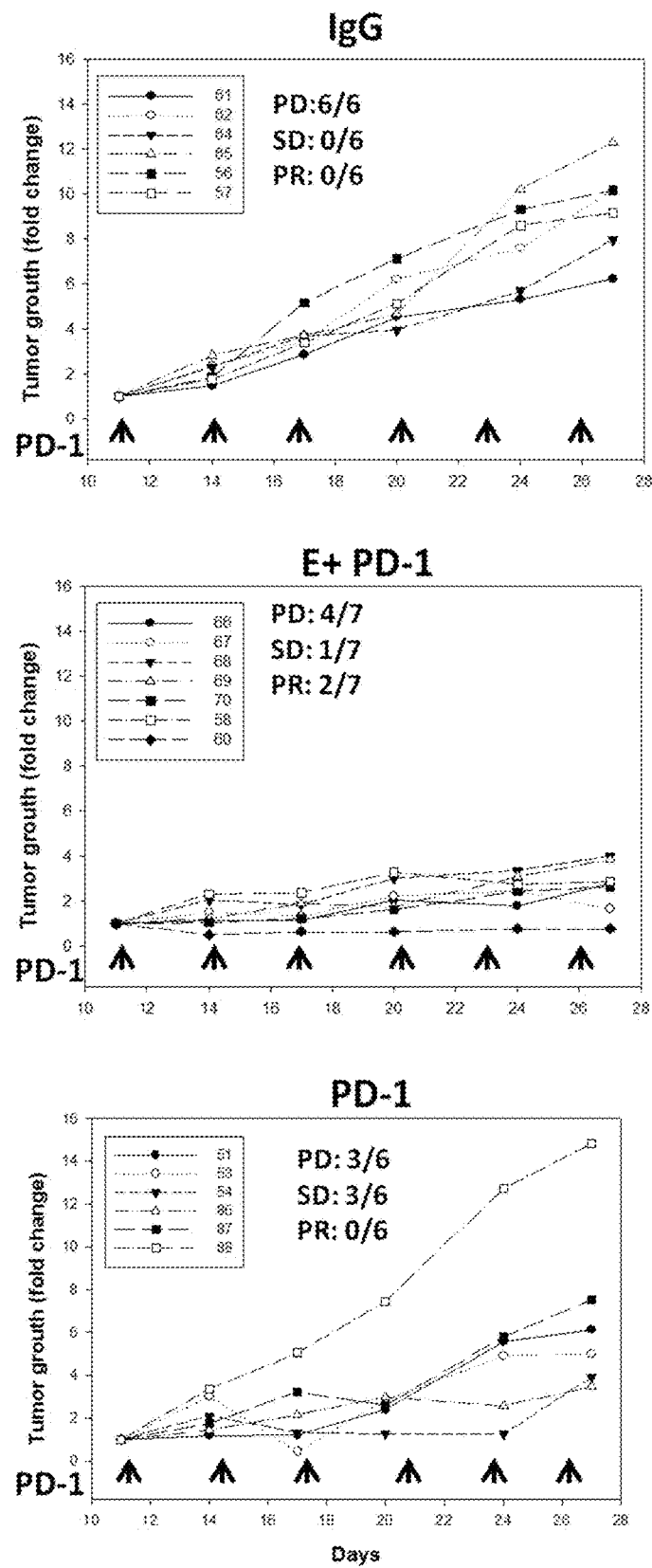
Figure 1B:
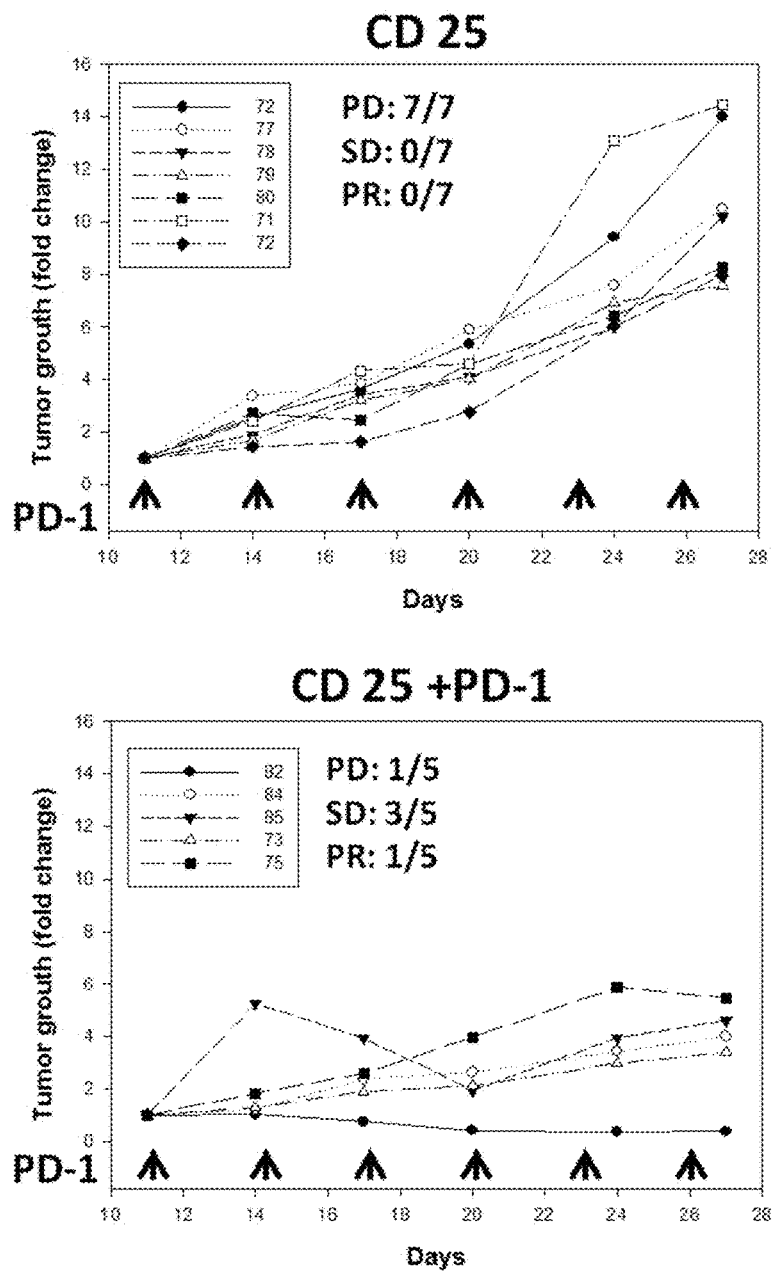
Figure 1C:
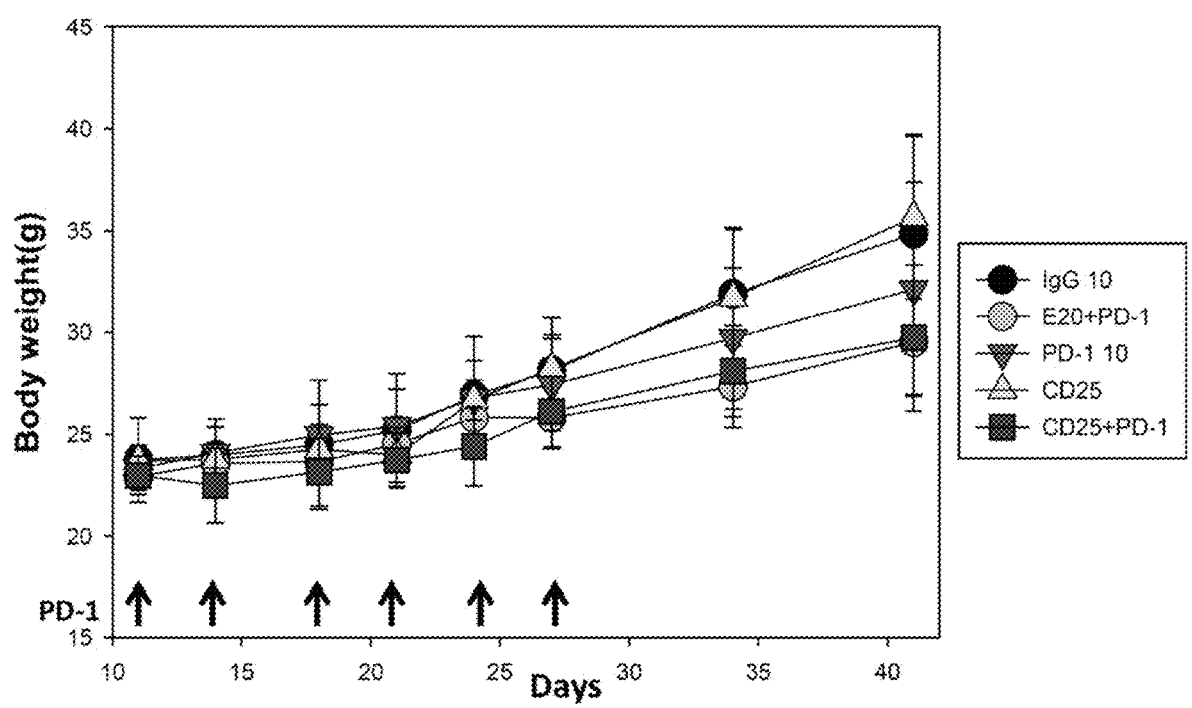
Figure 1D:
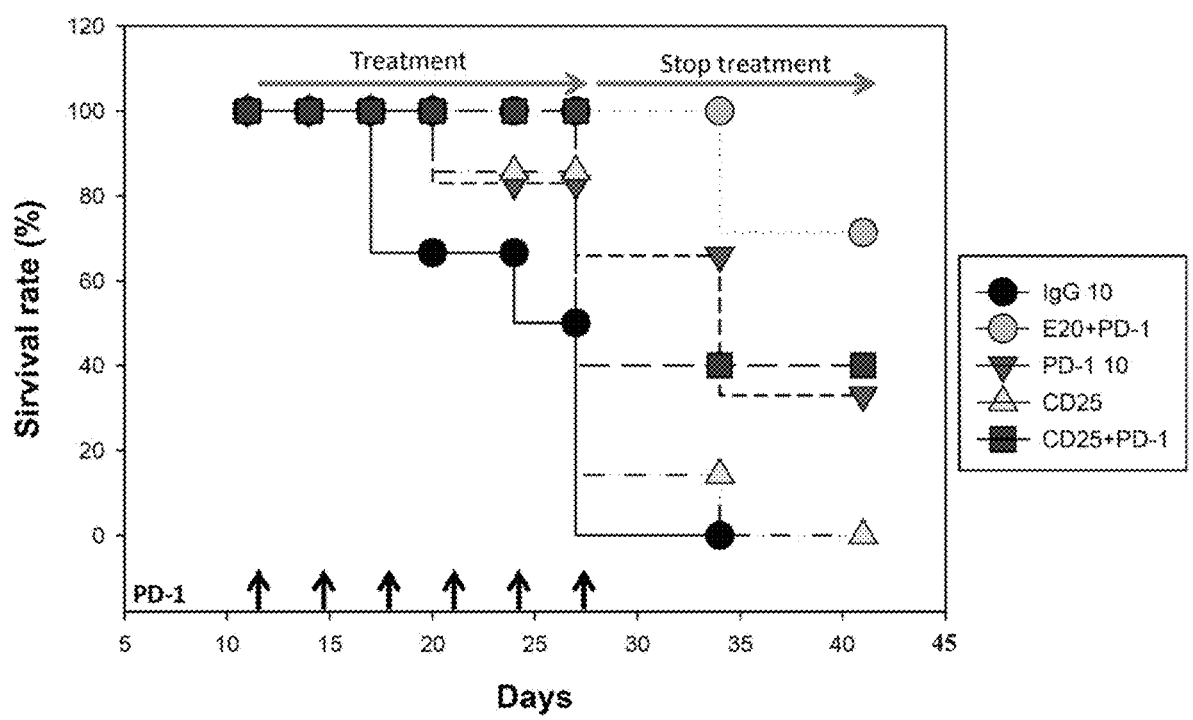

The anti-cancer activity of chidamide or entinostat in combination with anti-PD-1 antibody was evaluated in CT26 tumor cells bearing mice. The chidamide or entinostat were orally administered to CT26-bearing mice at a dose of 25 mg/kg and 20 mg/kg, respectively. Chidamide was administered daily and entinostat was administered every two days. Chidamide or entinostat combined with anti-PD-1 antibody exhibited more potent anti-cancer activity than anti-PD-1 antibody alone (FIG. 1A). Chidamide combined with the anti-PD-1 antibody was more effective in inhibiting tumor growth than chidamide alone. Our results show that one mouse achieved PR, SD was observed in three mice, and PD was observed in one mouse in the group of chidamide in combination with anti-PD-1 antibody (FIG. 1B). However, the entinostat combined with anti-PD-1 antibody group shows more potency in inhibiting tumor growth than the chidamide combined with anti-PD-1 antibody group (FIG. 1B). In all groups, the mice did not lose weight (FIG. 1C). The survival rate was evaluated with the tumor bearing mice model. The survival rate was evaluated when the tumor size reached approximately 3,000 mm$^3$. All drugs were administered from 11 to 26 days. The results show that chidamide combined with anti-PD-1 antibody group had a 40% survival rate at day 42, while the anti-PD-1 antibody group and entinostat combined with anti-PD-1 antibody group have survival rates of about 33% and 71%, respectively (FIG. 1D).

Figure 2A:
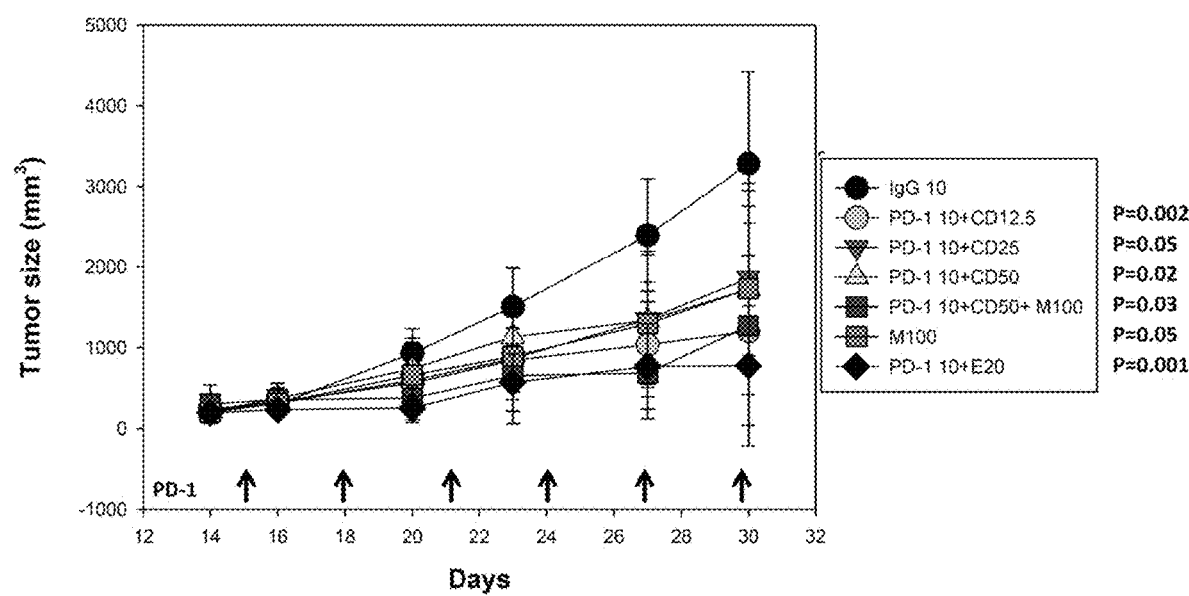
FIGS. 2 A to D show the therapeutic response of chidamide plus metformin combined with anti-PD-1 antibody in CT26 tumor-bearing mice. BALB/c mice bearing a CT26 colon tumor were treated with various therapeutic modalities as indicated. IgG, Anti-IgG control (vehicle, 10 mg/kg); PD-1, Anti-PD-1 monoclonal antibody (10 mg/kg); CD, chidamide (12.5, 25, or 50 mg/kg); E, MS-275 (entinostat, 20 mg/kg); M, metformin (100 mg/kg). Total tumor volumes (A), individual tumor volumes (B), CT26 tumor bearing-mice body weight (C), and animal survival (D) were recorded. CT26 tumor bearing mice were treated as indicated and euthanized at tumor volume of 3,000 mm$^3$ after tumor implantation. Means and SDs are shown. The number of animals used in each experimental arm and P values are also indicated.*P<0.05. P-values were calculated using Student's t-test that compared tumor size at indication group with IgG group.
Figure 2B:
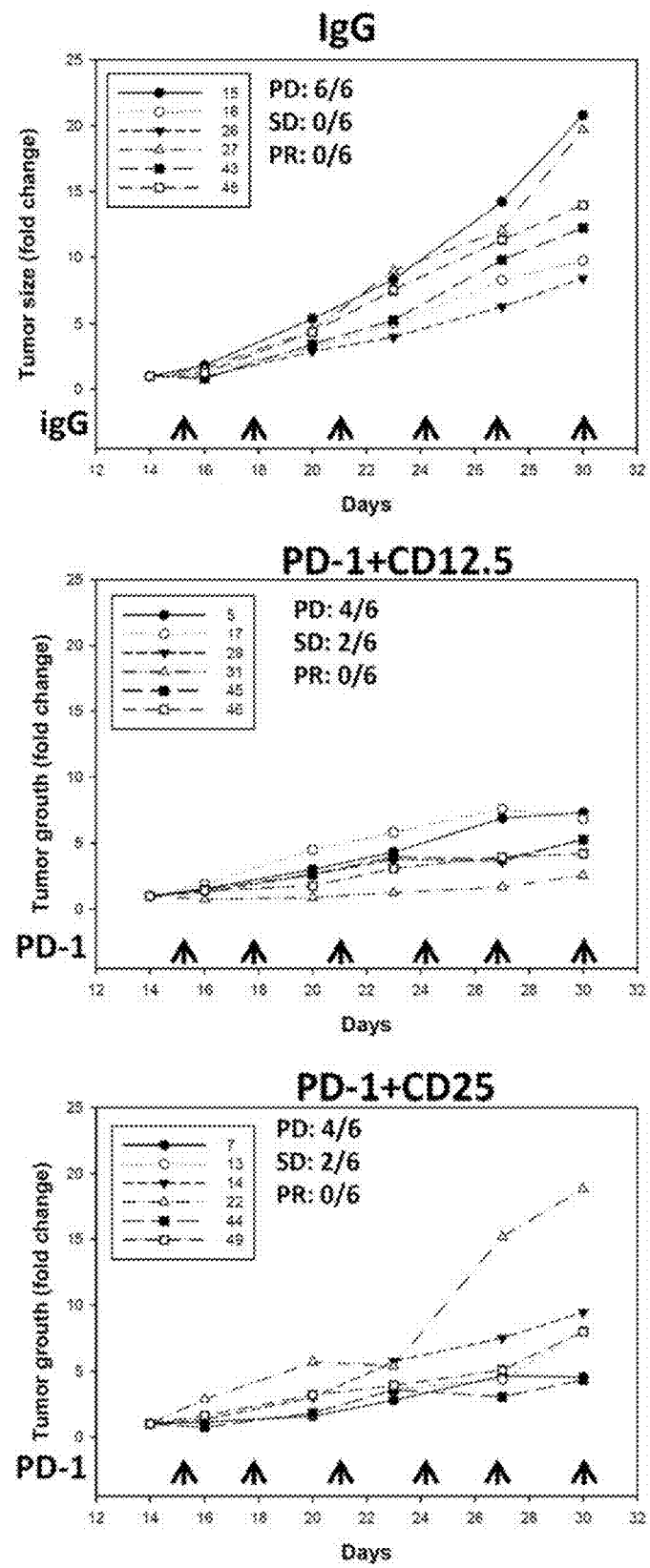
Figure 2B:
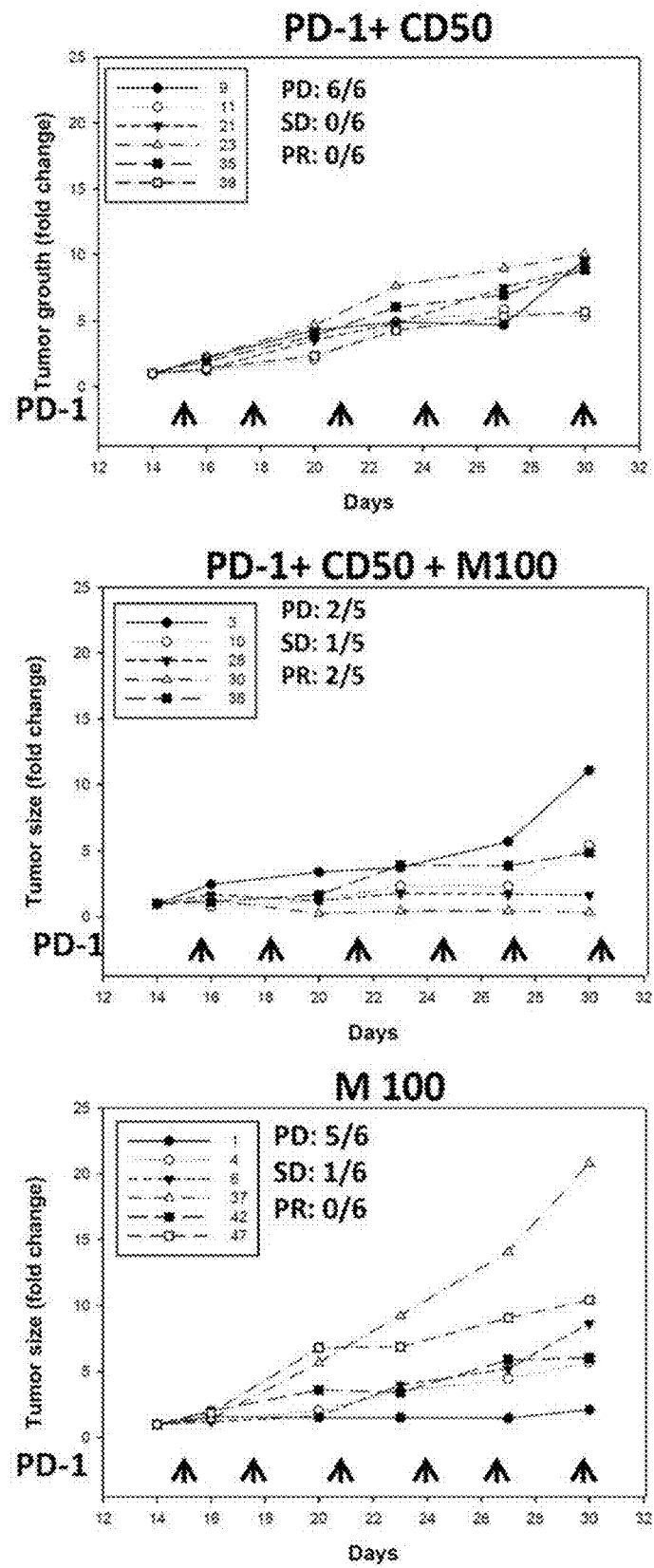
Figure 2B:
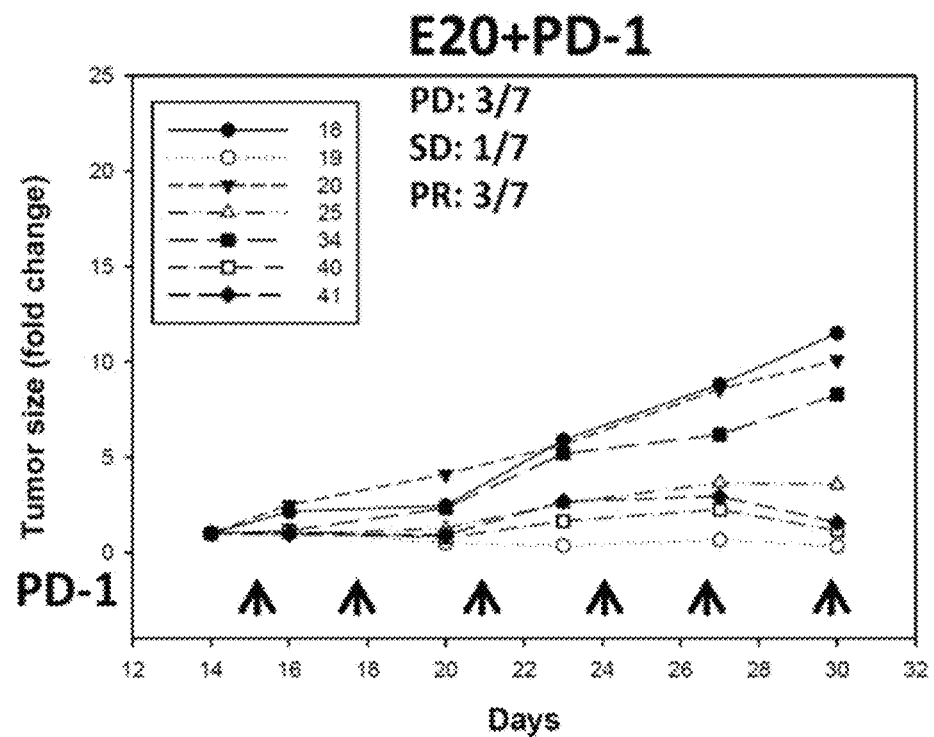
Figure 2C:
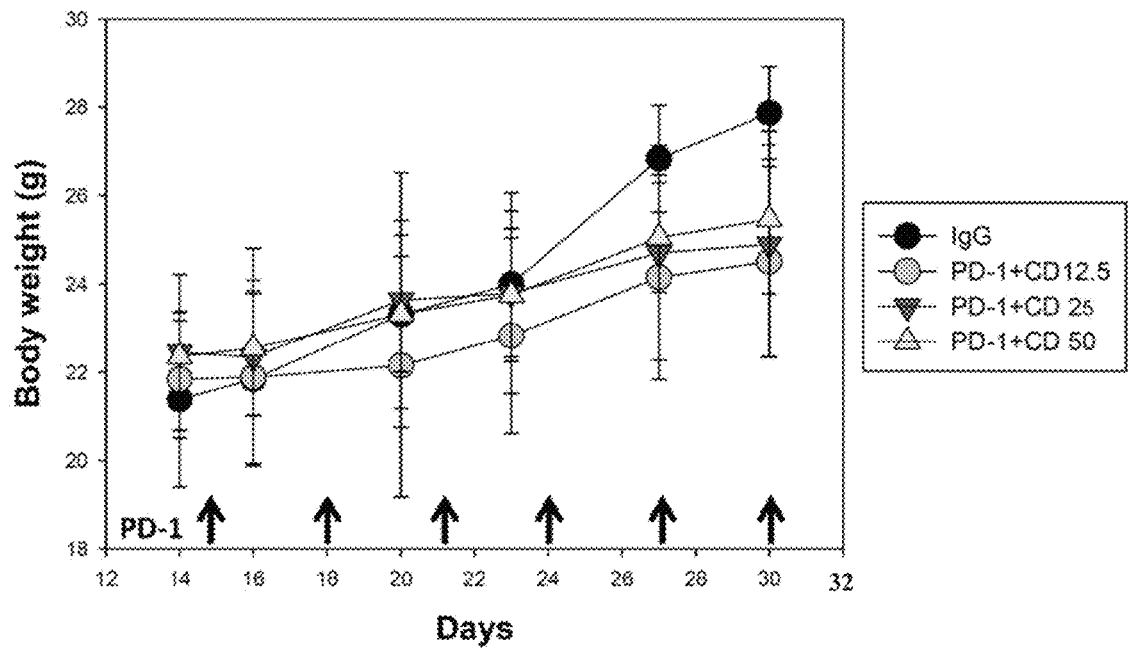
Figure 2C:
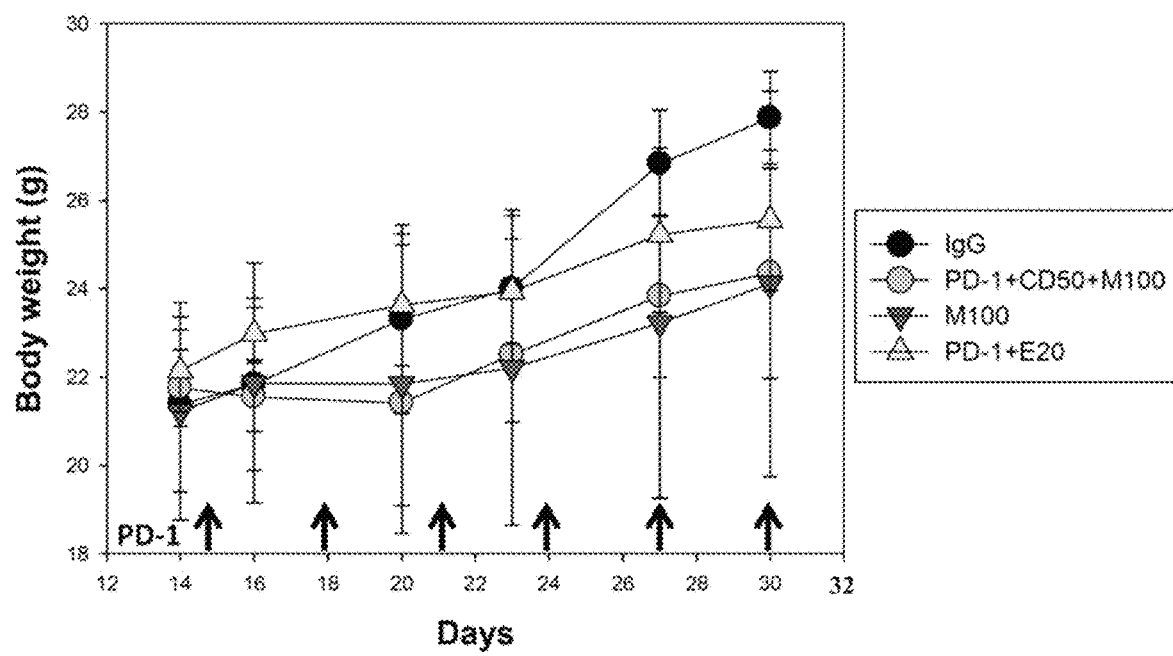
Figure 2D:
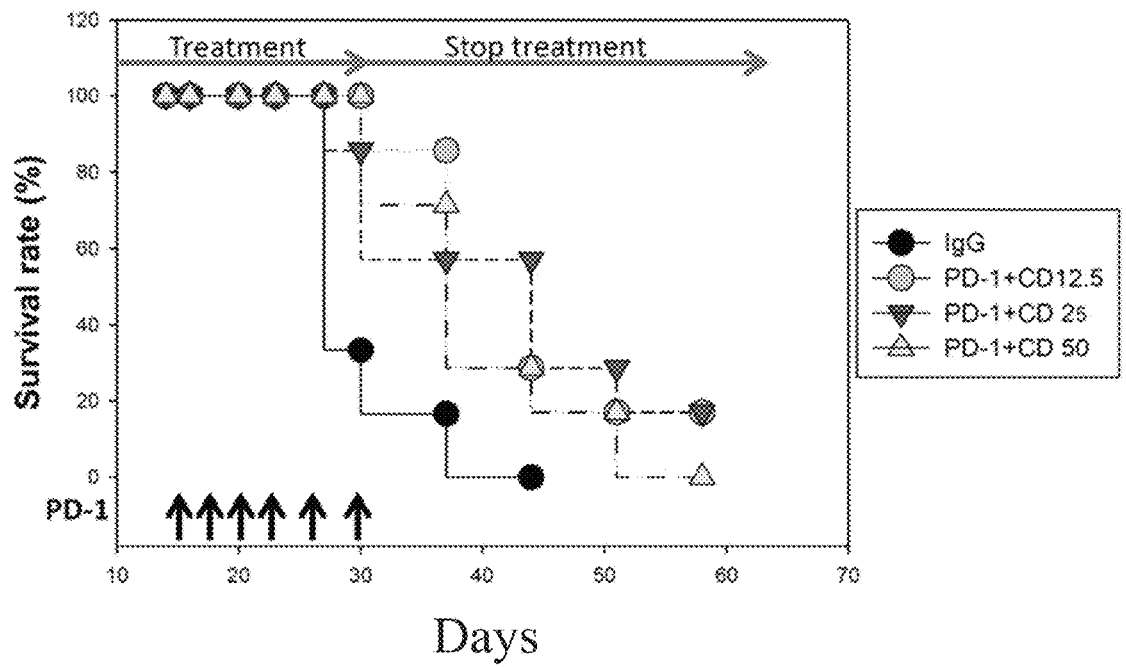
Figure 2D:
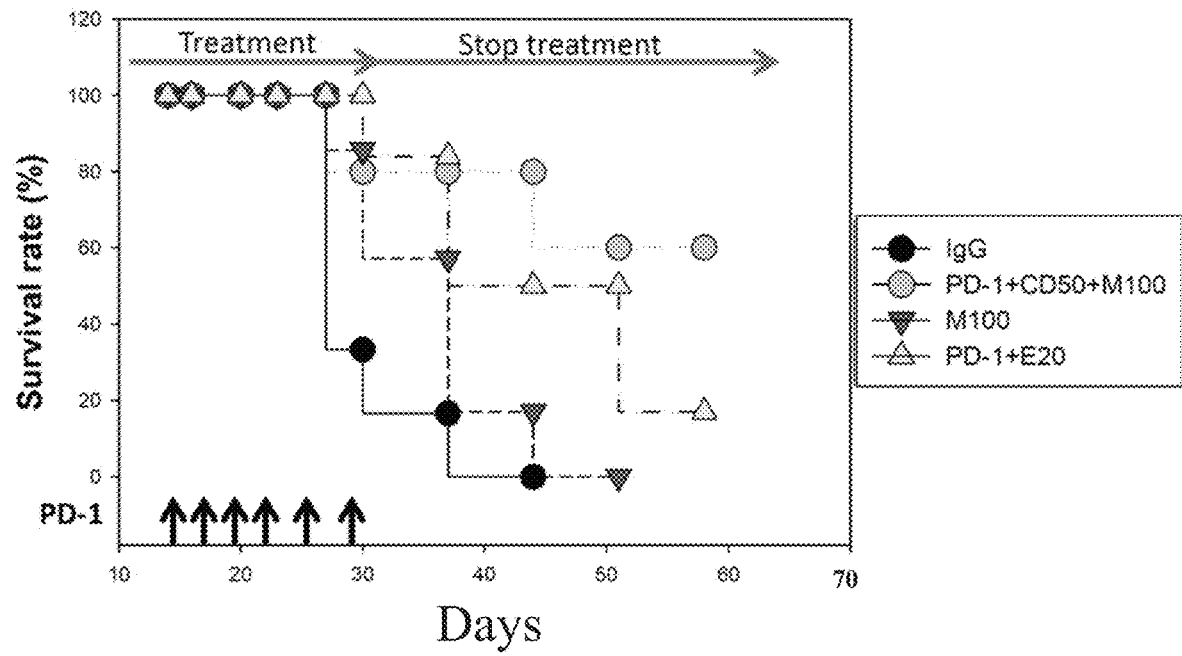

Example 3 Effects of Chidamide Combined with Metformin and Anti-PD-1 Antibody 100 mg/kg of metformin was orally administered to tumor bearing mice. The results show that the tumor growth was markedly inhibited in comparison with control group (see FIG. 2A). In the metformin group, SD was observed in one mouse and PD was observed in five mice (FIG. 2B). In the entinostat combined with anti-PD-1 antibody group (positive control), three mice achieved PR, SD was observed in one mouse and PD was observed in three mice (FIG. 2B). As shown in FIG. 2A, a higher dose (50 mg/kg) of chidamide combined with anti-PD-1 antibody has lower anti-cancer activity than a low dose (12.5 mg/kg) of chidamide combined with anti-PD-1 antibody. The treatment with chidamide at 12.5 mg/kg combined with anti-PD-1 antibody was more potent in inhibiting tumor growth than chidamide at 25 or 50 mg/kg combined with anti-PD-1 antibody (FIG. 2B). In the 12.5 mg/kg chidamide combined with anti-PD-1 antibody group, SD was observed in two mice and PD was observed in four mice. However, the increase of chidamide dose did not boost the anti-cancer activity (FIG. 2B). Two groups, chidamide (50 mg/kg) combined with anti-PD-1 antibody and chidamide (50 mg/kg) plus metformin (100 mg/kg) combined with anti-PD-1 antibody, were tested and the results are shown in FIG. 2B. The results show that the treatment with chidamide combined with metformin and anti-PD-1 antibody is more potent in inhibiting tumor growth than that with chidamide combined with anti-PD-1 antibody. As shown in FIG. 2B, two mice achieved PR, SD was observed in one mouse, and PD was observed in two mice. The mice in the treatment groups did not lose body weight (see FIG. 2C). Next, the survival rate of the mice in the treatment groups was determined at day 58. As shown in FIG. 2D, the drug treatment stopped at day 30. The treatment with chidamide (50 mg/kg) combined with metformin and anti-PD-1 antibody experienced more potent inhibition of tumor growth, and significantly increased the survival rate compared to other combination treatments. In the chidamide (50 mg/kg) combined with metformin and anti-PD-1 antibody group, the survival rate increased to 60%, while the positive control group (entinostat combined with anti-PD-1 Ab) only had around 20% of the survival rate. Chidamide (50 mg/kg) combined with anti-PD-1 antibody (10 mg/kg) cannot stop tumor growth; however, after adding metformin (100 mg/kg) to the combination, the inhibitory activity and survival rate increased. The result suggests that metformin can influence the tumor carbohydrate metabolite in a tumor microenvironment and thus improves immune checkpoint inhibitor anti-cancer activity (FIG. 2D).

Figure 3A:
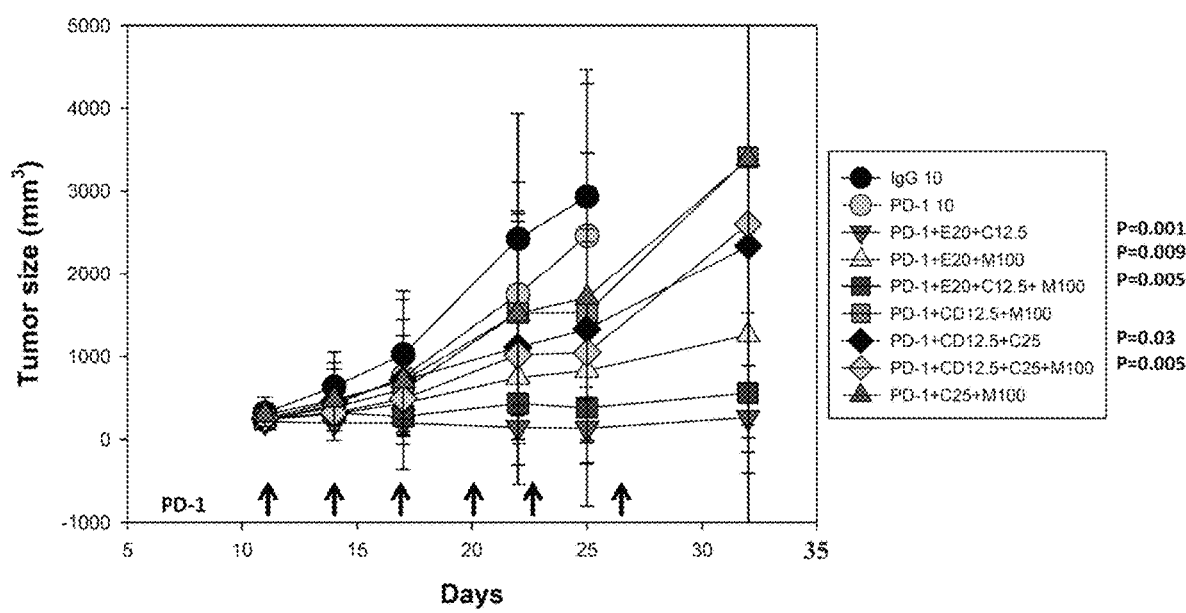
FIGS. 3 A to D show the therapeutic response of chidamide or entinostat plus metformin and celecoxib combined with anti-PD-1 antibody in CT26 tumor-bearing mice. BALB/c mice bearing a CT26 colon tumor were treated with various therapeutic modalities as indicated. IgG, Anti-IgG control (vehicle, 10 mg/kg); PD-1, Anti-PD-1 monoclonal antibody (10 mg/kg); CD, chidamide (12.5 mg/kg); E, MS-275 (entinostat, 20 mg/kg); C, celecoxib (25 mg/kg); M, metformin (100 mg/kg). Total tumor volumes (A), individual tumor volumes (B), bearing-mice body weight (C), and animal survival (D) were recorded. CT26 tumor bearing-mice were treated as indicated and euthanized at tumor volume of 3,000 mm$^3$ after tumor implantation. Means and SDs are shown. The number of animals used in each experimental arm and P values are also indicated.*P<0.05. P-values were calculated using Student's t-test that compared tumor size at indication group with IgG group.
Figure 3B:
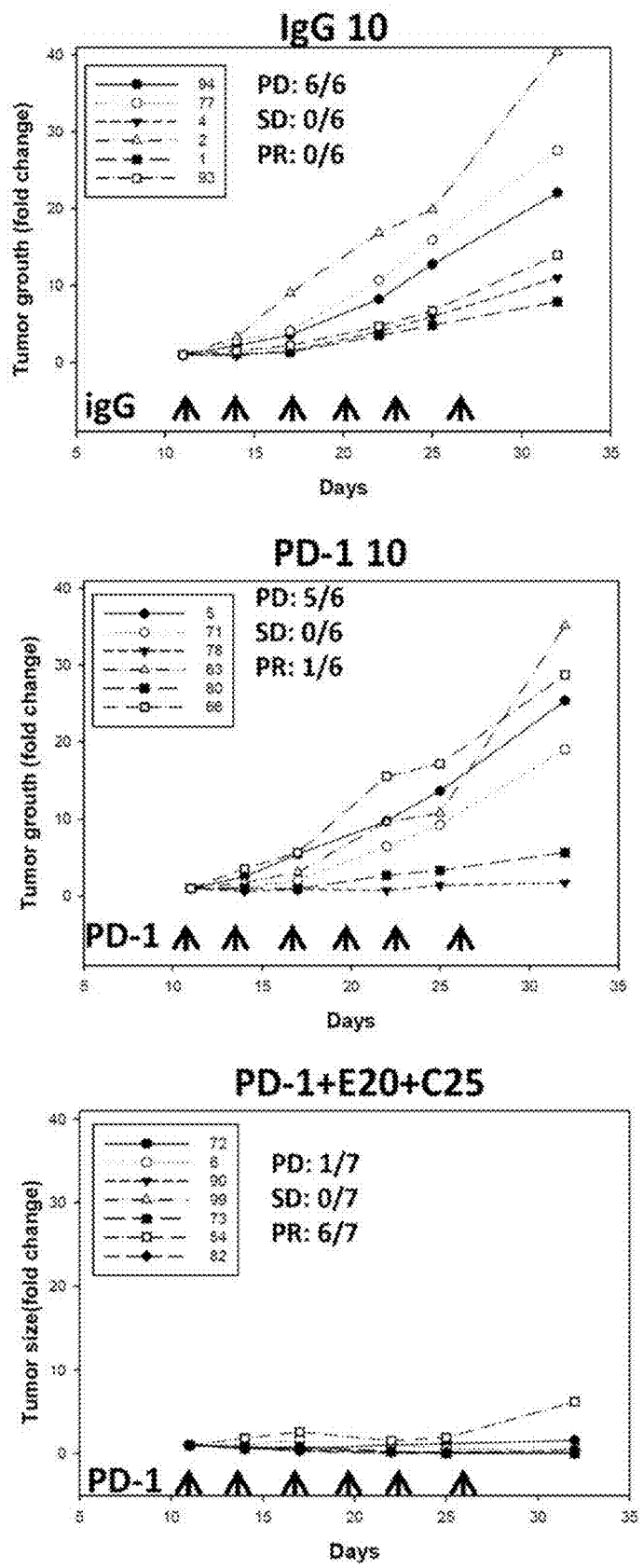
Figure 3B:
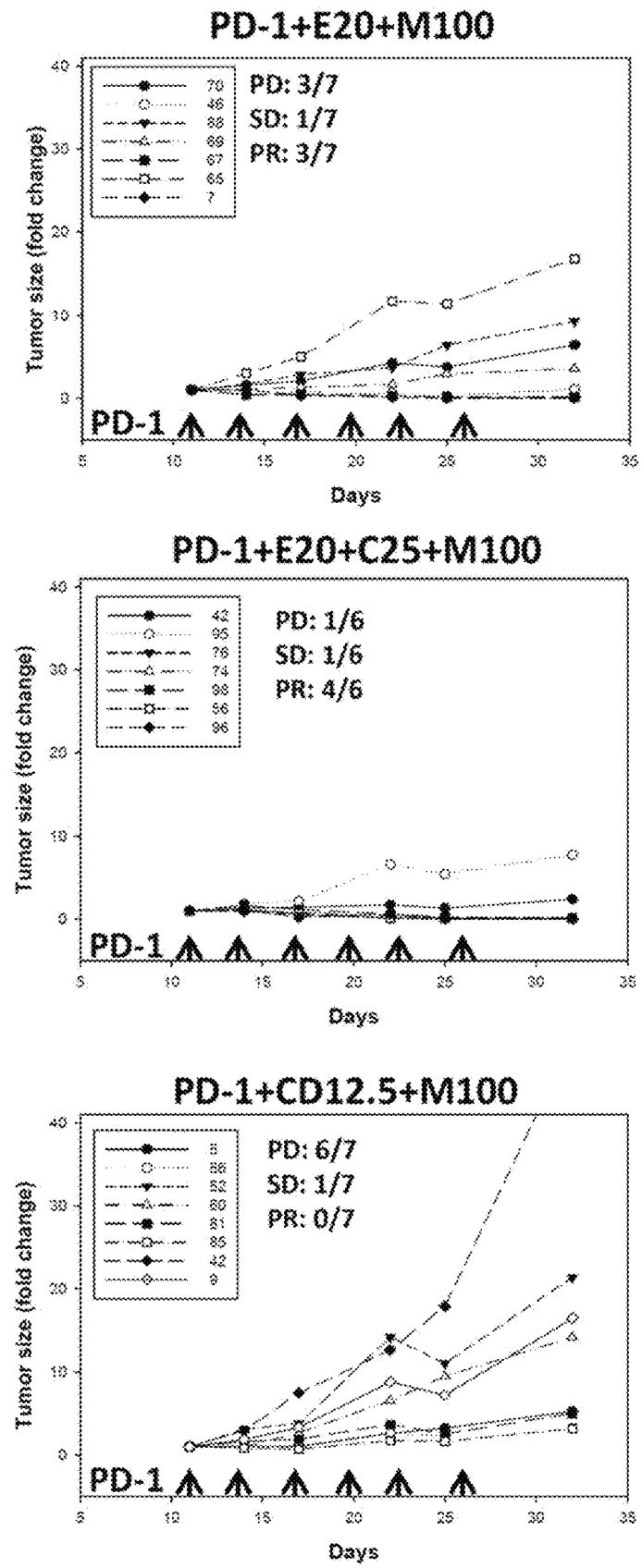
Figure 3B:
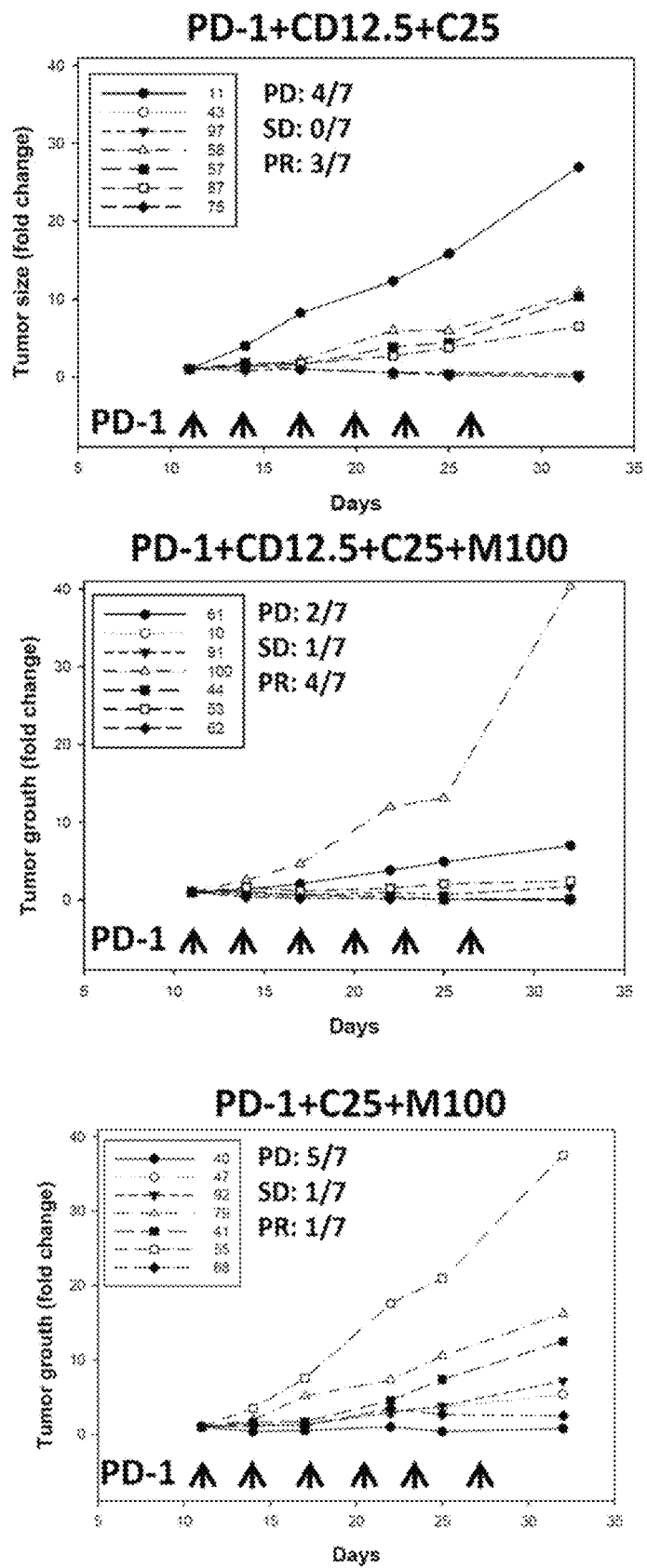
Figure 3C:
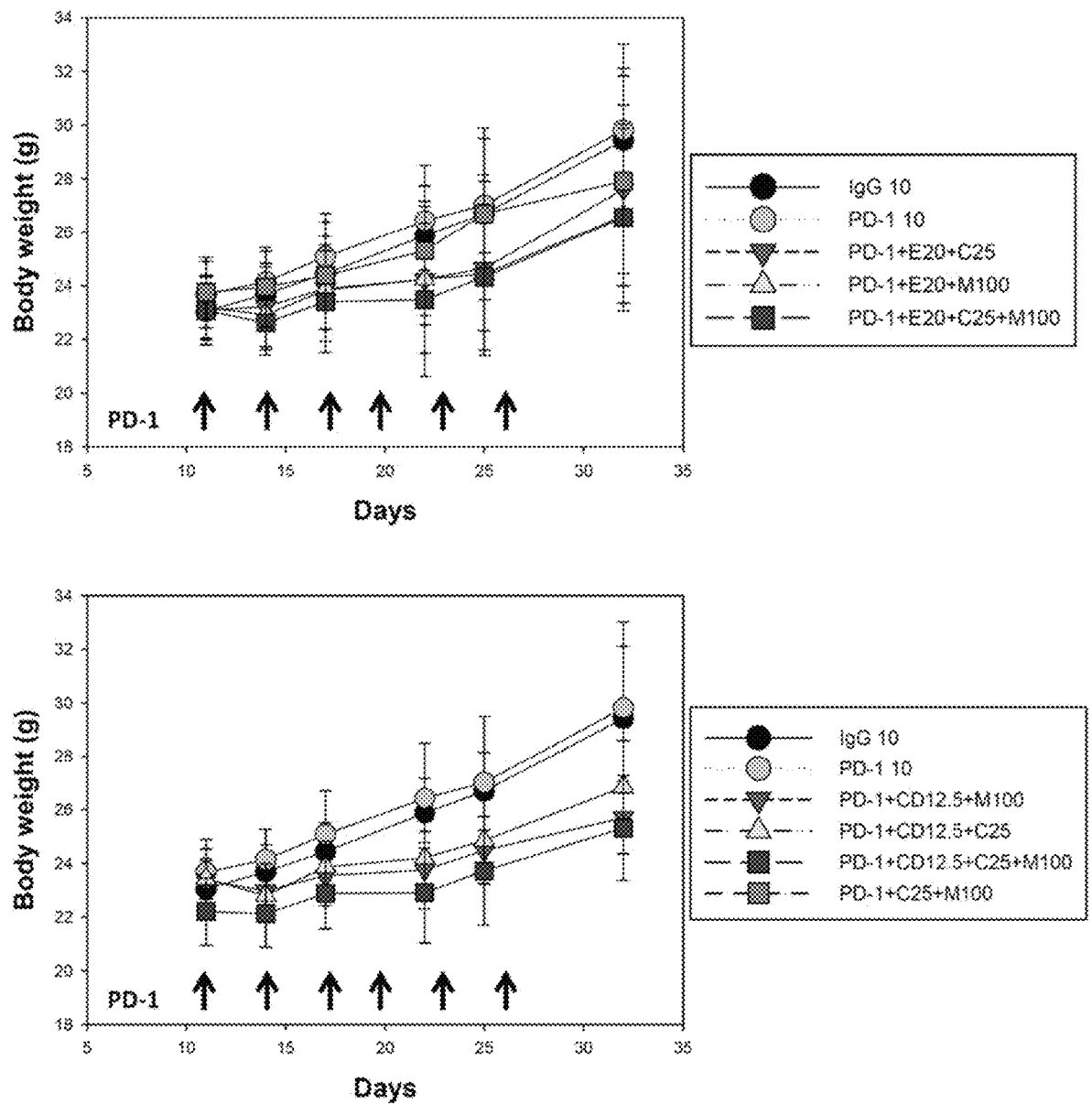
Figure 3D:
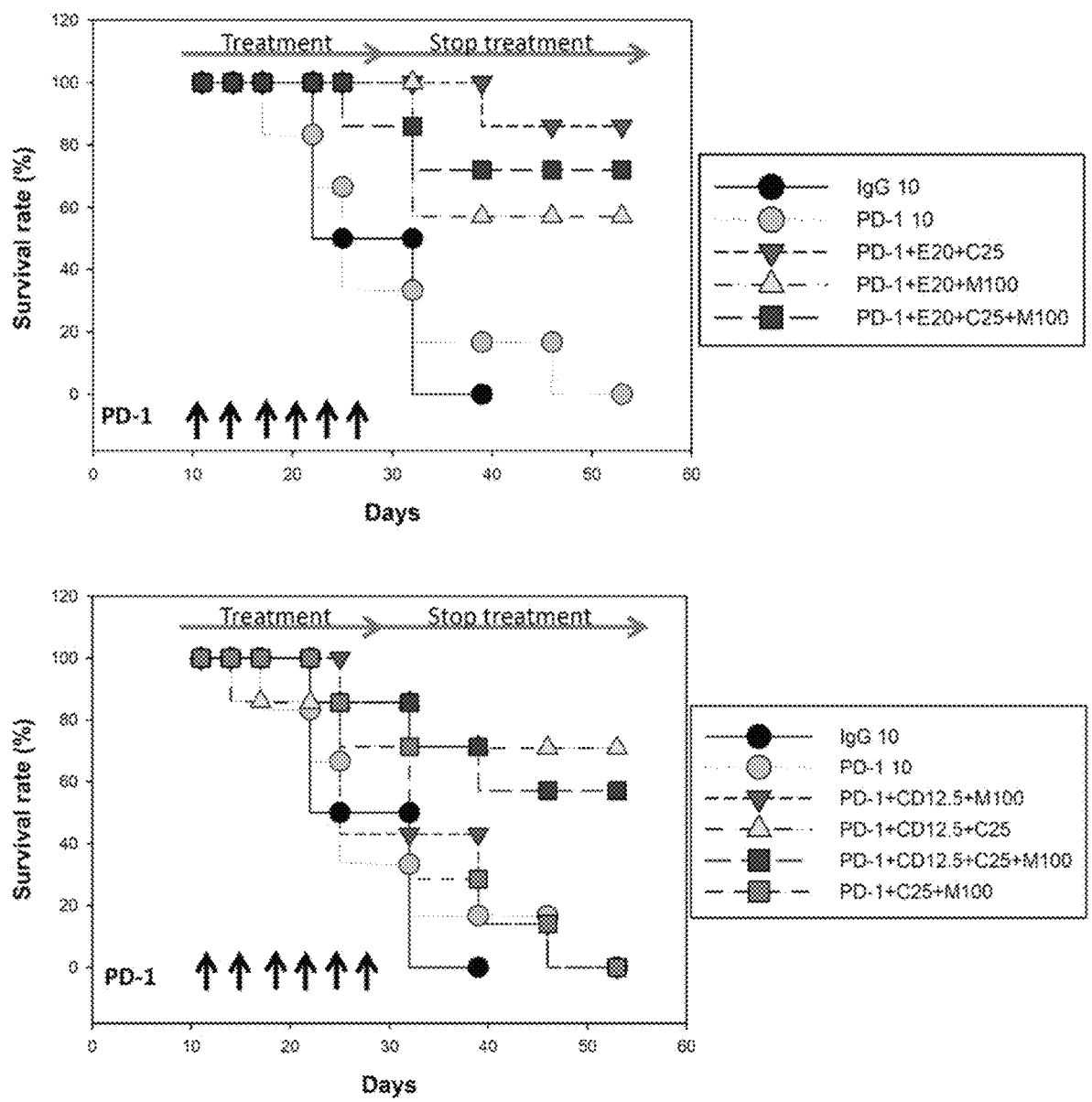

Example 4 Effects of Chidamide or Entinostat+Metformin+Celecoxib Combined with anti-PD-1 antibody The treatment with chidamide+metformin+celecoxib+anti-PD-1 antibody or entinostat+metformin+celecoxib+anti-PD-1 antibody was more potent in inhibiting tumor growth than that without celecoxib (FIG. 3A). The entinostat group is more potent than the chidamide group. However, in the absence of an epigenetic modulator, the treatment group of metformin+celecoxib combined with anti-PD-1 antibody showed decreased anti-cancer activity. No mice in the treatment groups lost any body weight (FIG. 3C). Furthermore, FIG. 3B shows the tumor growth of all the mice in the treatment groups. Our results show that the entinostat+metformin combined with the anti-PD-1 antibody and the entinostat+celecoxib combined with anti-PD-1 antibody are very potent in achieving a high percentage of PR. Celecoxib plays a more important role in the anti-tumor in a tumor microenvironment than metformin (FIG. 3B). The chidamide+metformin combined with anti-PD-1 antibody or chidamide+celecoxib combined with the anti-PD-1 antibody shows similar results, which achieve a high percentage of PR. However, in the absence of chidamide or entinostat, the anti-cancer activity in the immune checkpoint inhibitor-treatment groups decreases (FIG. 3B). The results suggest that the immune checkpoint inhibitors need to be combined with the epigenetics modulator to improve anti-cancer activity. The improvement may result from the control of the carbohydrate metabolite and PGE2 production in a tumor microenvironment by metformin and celecoxib, and therefore it will result in significantly increased response rate of the CT26 tumor bearing mice. Moreover, the survival rate of the entinostat or chidamide+metformin+celecoxib combined with anti-PD-1 antibody group increases to about 60-80%. However, in the absence of chidamide/entinostat, the survival rate decreases (see the metformin plus celecoxib combined with anti-PD-1 antibody group in FIG. 3D). Regarding survival rate, celecoxib exhibits increased survival rates as compared to metformin (FIG. 3D). We found that celecoxib alone or celecoxib combined with metformin are important factors in synergizing the effect of class I HDAC inhibitor combined with the anti-PD-1 antibody in augmenting the anti-cancer activity. The combination of the class I HDAC inhibitor+metformin+celecoxib combined with immune checkpoint inhibitors shows promise in its ability to cure cancer in the tumor bearing mice model.

Figure 4A:
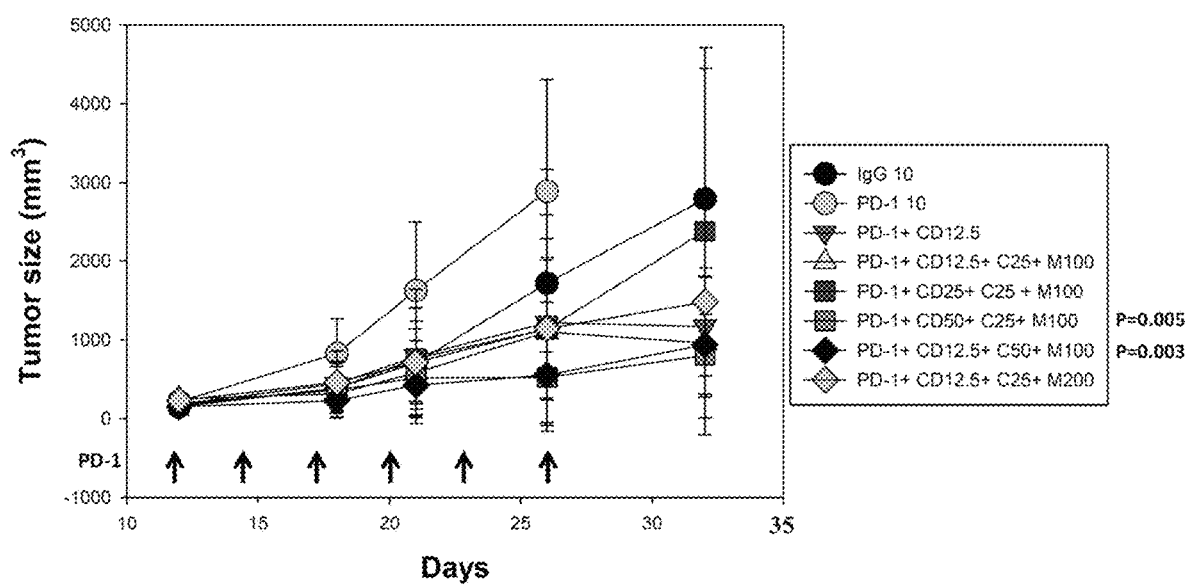
FIGS. 4 A to D show the therapeutic response of chidamide plus metformin and celecoxib at various doses combined with anti-PD-1 antibody in CT26 tumor-bearing mice. BALB/c mice bearing a CT26 colon tumor were treated with various therapeutic modalities as indicated. IgG, Anti-IgG control (vehicle, 10 mg/kg); PD-1, Anti-PD-1 monoclonal antibody (10 mg/kg); CD, chidamide (12.5, 25, or 50 mg/kg); C, celecoxib (25 or 50 mg/kg); M, metformin (100 or 200 mg/kg). Total tumor volumes (A), individual tumor volumes (B), CT26 tumor bearing-mice body weight (C), and animal survival (D) were recorded. CT26 tumor bearing mice were treated as indicated and euthanized at tumor volume of 3,000 mm$^3$ after tumor implantation. Means and SDs are shown. The number of animals used in each experimental arm and P values are also indicated.*P<0.05. P-values were calculated using Student's t-test that compared tumor size at indication group with IgG group.
Figure 4B:
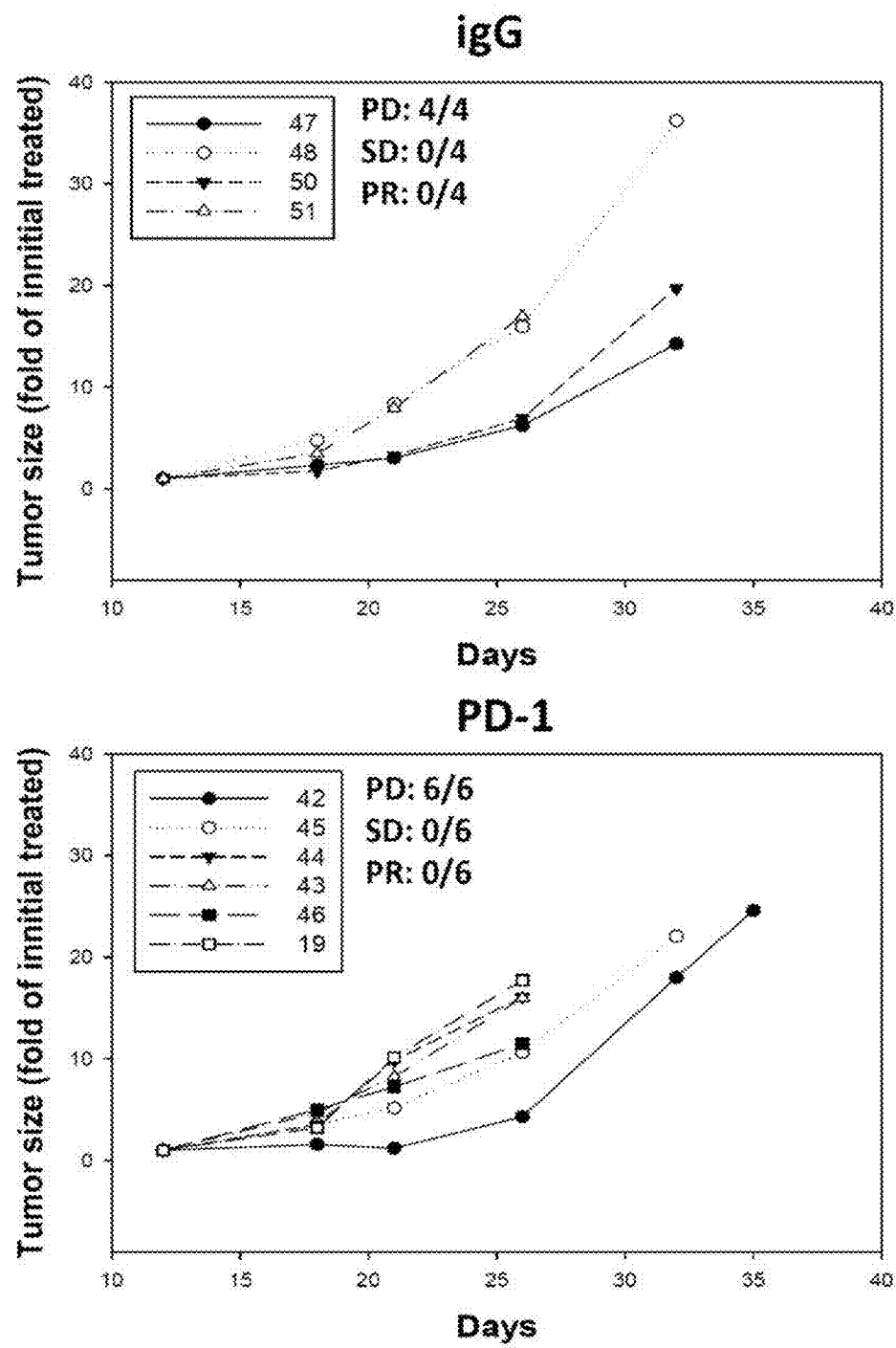
Figure 4B:
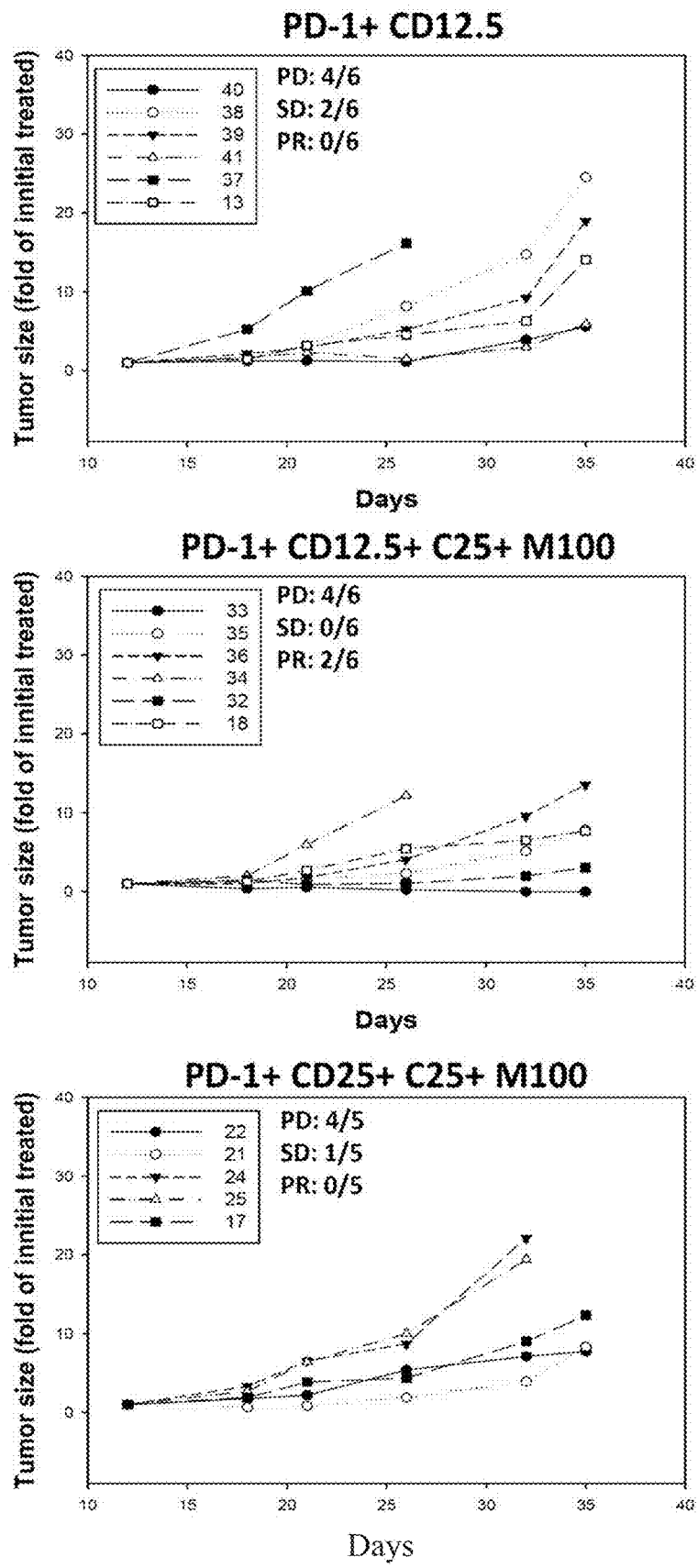
Figure 4B:
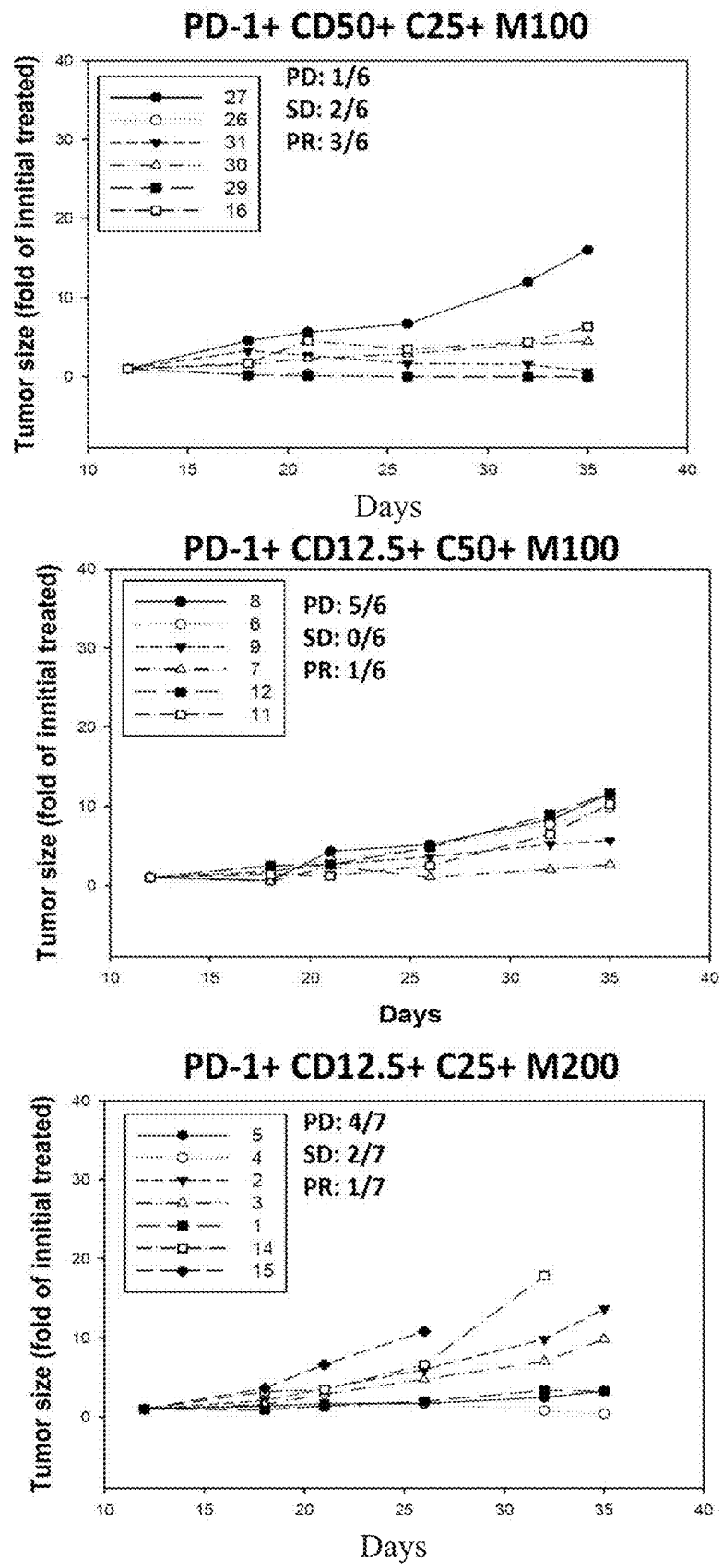
Figure 4C:
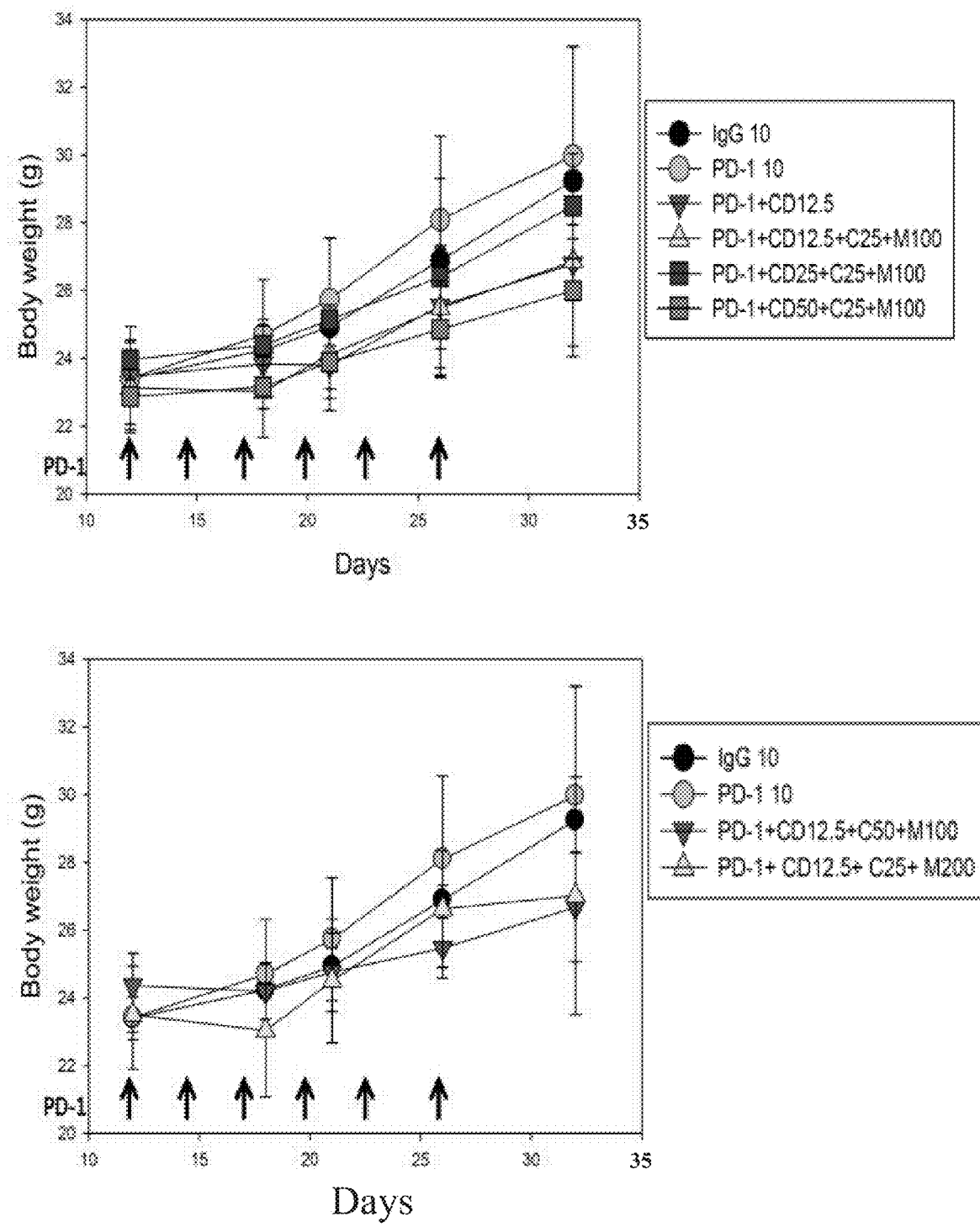
Figure 4D:
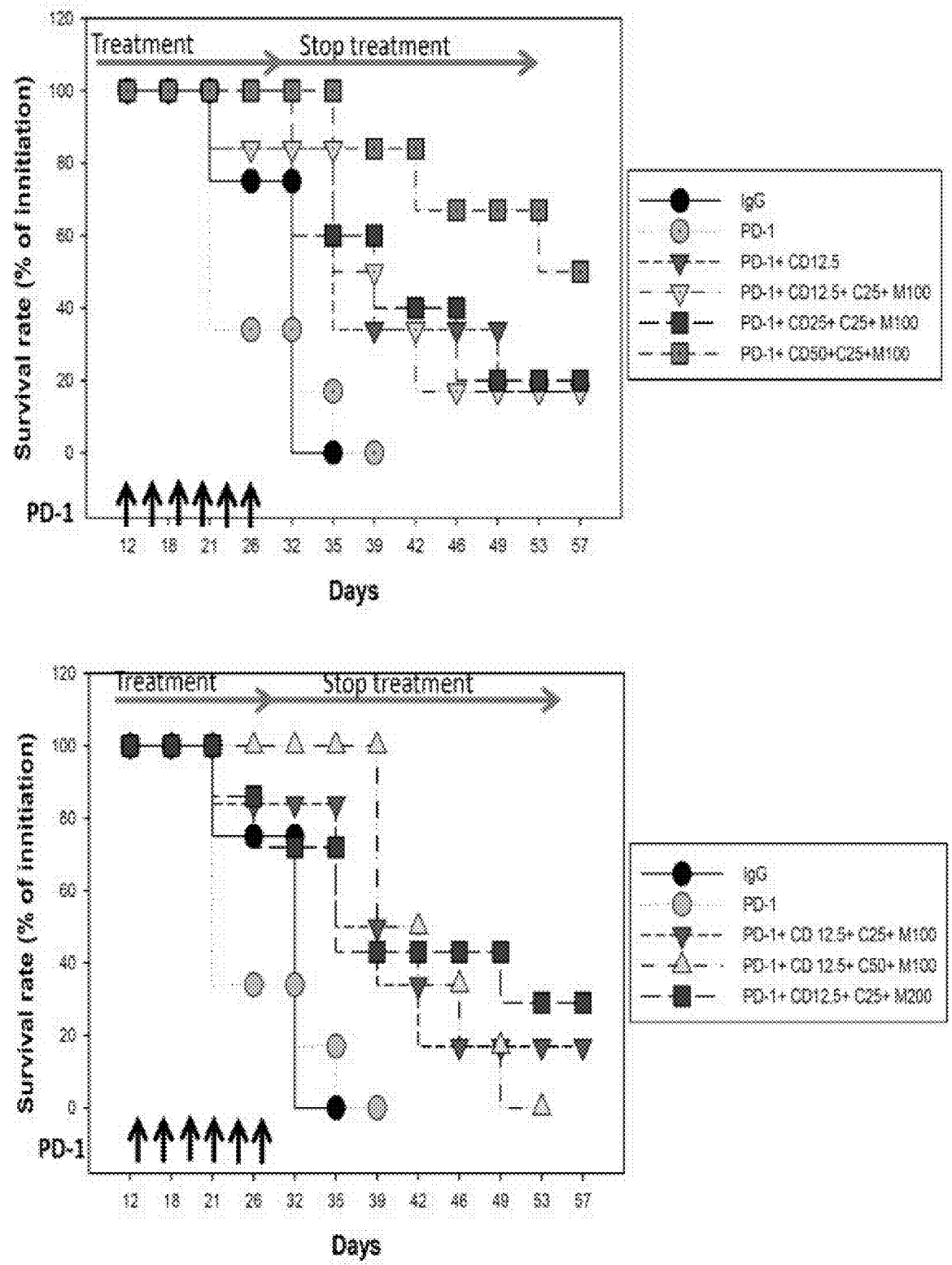

Next, the optimal response dose of chidamide was determined. As shown in FIG. 4A, treatments with different therapeutic regimens with a fixed dose of the anti-PD-1 antibody (10 mg/kg), various doses of chidamide (12.5, 25.0, and 50 mg/kg), various doses of celecoxib (25 and 50 mg/kg), and various doses of metformin (100 and 200 mg/kg) were performed in CT26 tumor cells bearing mice. The tumor growth in all mice in these treatment groups is significantly inhibited in comparison with the anti-PD-1 group or the vehicle group (anti-IgG group). As shown in FIG. 4B, tumor growth is inhibited in all treatment groups. The group of chidamide combined with the anti-PD-1 antibody shows more potent inhibition in tumor growth than the treatment with the anti-PD-1 antibody only. Furthermore, the regimen of chidamide (12.5 mg/kg) plus celecoxib (25 mg/kg) and metformin (100 mg/kg) combined with the anti-PD-1 antibody achieved a PR proportion of about 33% (two mice achieved PR), and is more active in suppressing tumor growth than chidamide (12.5 mg/kg) combined with the anti-PD-1 antibody. However, no PR was found in the group of chidamide (12.5 mg/kg) combined with the anti-PD-1 antibody. The result suggests that celecoxib and metformin play an important role to boost the response rate in the treatment with immune checkpoint inhibitors. Various doses of chidamide were tested in similar regimens to analyze the response rate of the CT26 tumor cells bearing mice. The results show that a dose of 50 mg/kg dose is optimal for chidamide in inhibiting tumor growth, and has a high proportion of PR (about 50%) and SD (about 33%) in the treatment regimen of chidamide (50 mg/kg) plus celecoxib (25 mg/kg) and metformin (100 mg/kg) combined with the anti-PD-1 antibody group. The result suggests that chidamide is a key factor in achieving therapeutic effect. Next, the optimum dose of celecoxib was determined. The results show that celecoxib at a dose of 50 mg/kg is more active than at 25 mg/kg to suppress tumor growth in each mouse in the treatment group (FIG. 4B). However, the immune checkpoint inhibitor has a very low response rate. We surprisingly found that celecoxib at 50 mg/kg can up-regulate the response rate in immunotherapy. Furthermore, the optimum dose of metformin was determined. It was found that metformin at a dose of 100 or 200 mg/kg of regimen makes no difference in anti-cancer activity (FIG. 4B). These data suggest that chidamide and celecoxib are more important than metformin in combination with an immune checkpoint inhibitor. As shown in FIG. 4C, none of the mice in any treatment groups lost any body weight. FIG. 4D shows the survival rates of the mice in the treatment groups. These data suggest that the regimen of chidamide (50 mg/kg) plus celecoxib (25 mg/kg) and metformin (100 mg/kg) combined with the anti-PD-1 antibody (10 mg/kg) is the best combination, which has a powerful ability to suppress tumor growth and raises the survival rate up to about 50%. The survival rate of other groups also increased in comparison with the anti-PD-1 antibody group alone. Although chidamide at 50 mg/kg plus celecoxib 25 mg/kg and metformin 100 mg/kg combined with the anti-PD-1 antibody (10 mg/kg) is the optimum regimen in this in vivo experiment, celecoxib at 50 mg/kg may also provide more contribution to the anti-cancer activity and also increase the survival rate in the CT26 tumor cells bearing mice.

Figure 5A:
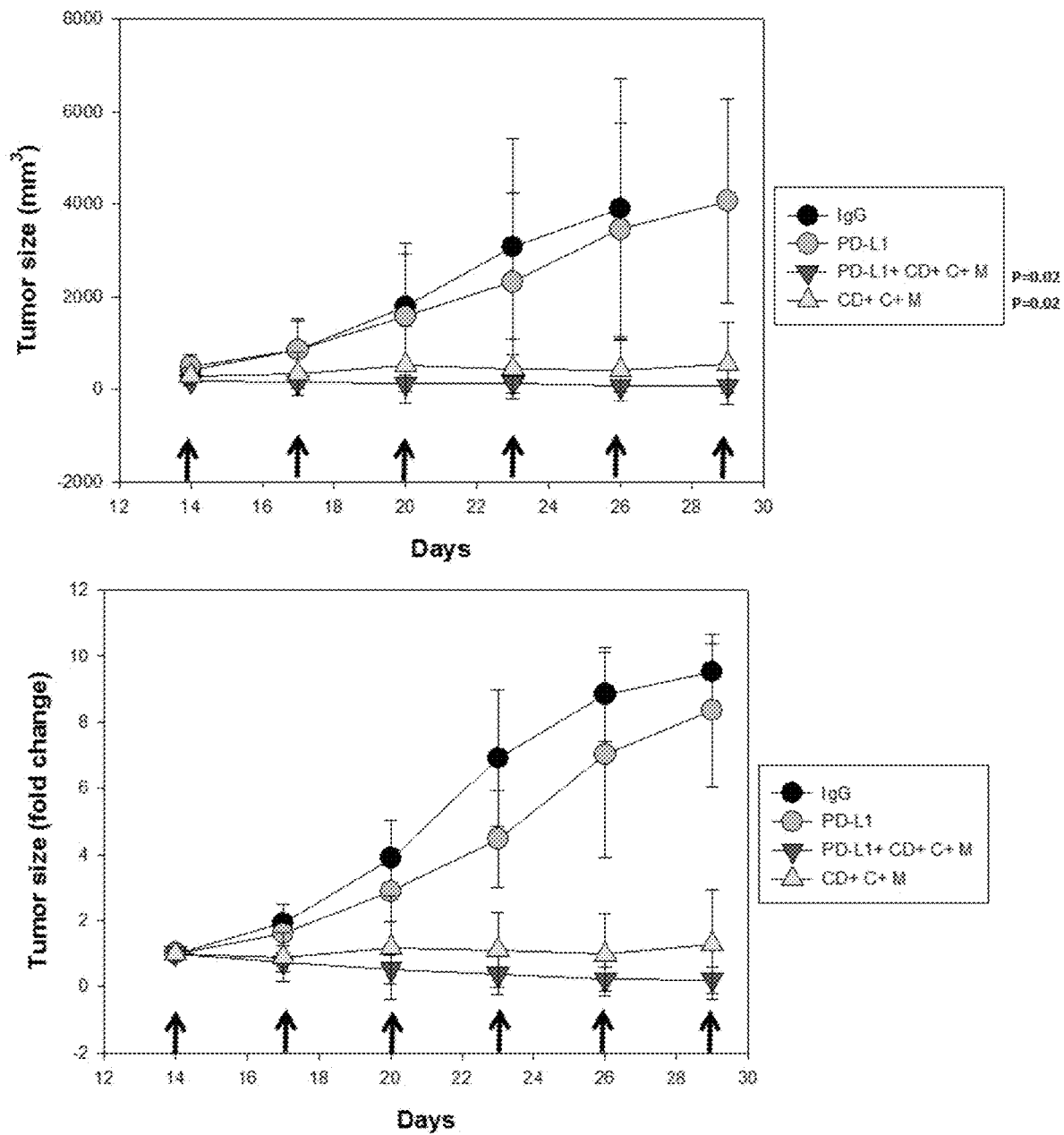
FIGS. 5 A to D show the therapeutic response of chidamide plus metformin and celecoxib combined with anti-PD-L1 antibody in CT26 tumor-bearing mice. BALB/c mice bearing a CT26 colon tumor were treated with various therapeutic modalities as indicated. IgG, Anti-IgG control (vehicle, 10 mg/kg); PD-L1, Anti-PD-L1 monoclonal antibody (10 mg/kg); CD, chidamide (50 mg/kg); C, celecoxib (50 mg/kg); M, metformin (100 mg/kg). Total tumor volumes (A), individual tumor volumes (B), CT26 tumor-bearing-mice body weight (C), and animal survival (D) were recorded. CT26 tumor bearing mice were treated as indicated and euthanized at tumor volume of 3,000 mm$^3$ after tumor implantation. Means and SDs are shown. The number of animals used in each experimental arm and P values are also indicated.*P<0.05. P-values were calculated using Student's t-test that compared tumor size at indication group with IgG group.
Figure 5B:
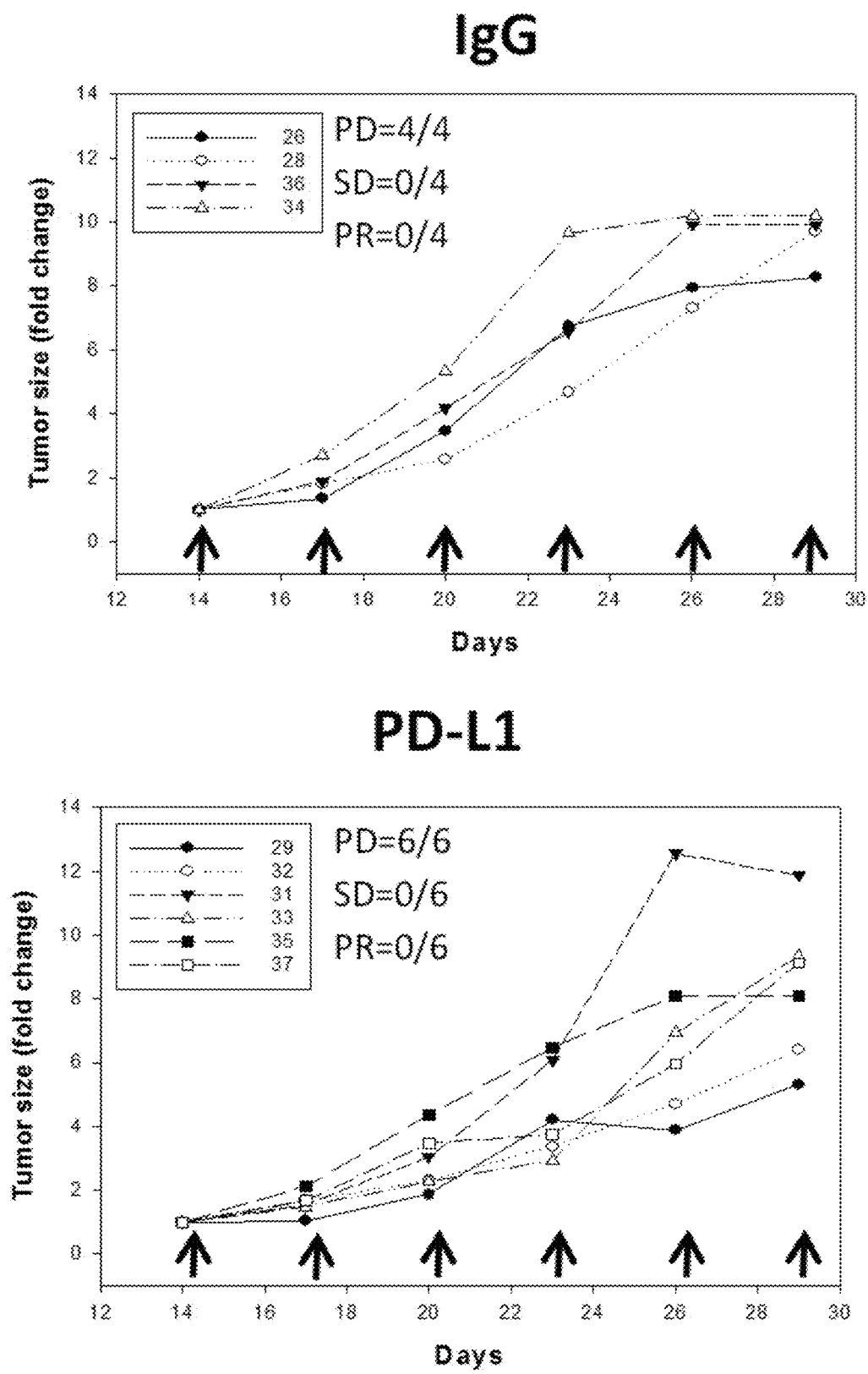
Figure 5B:
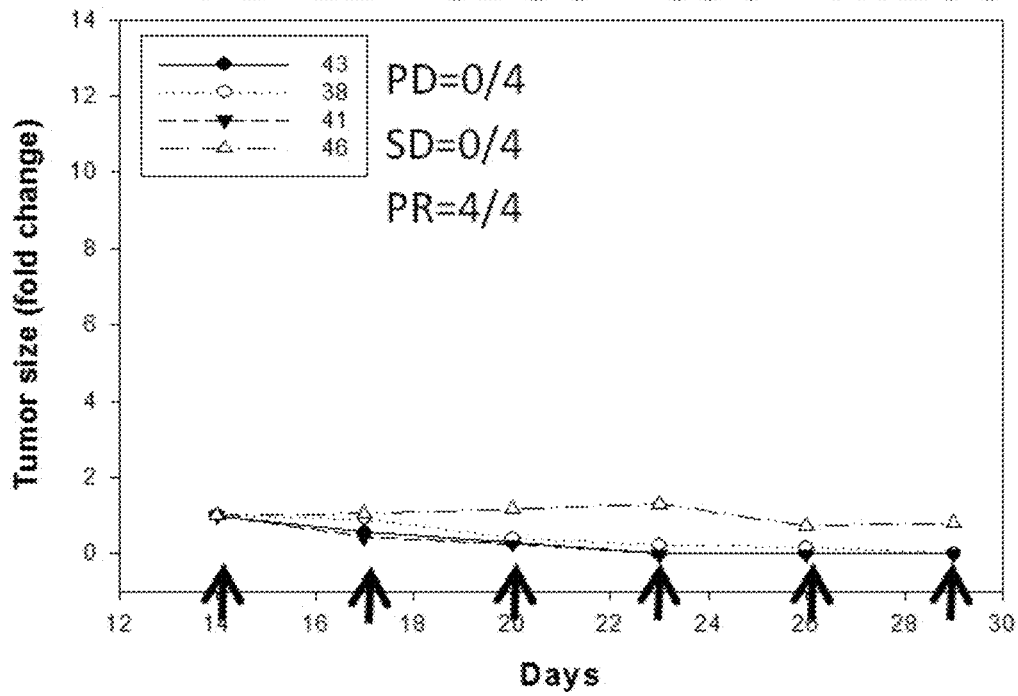
Figure 5B:
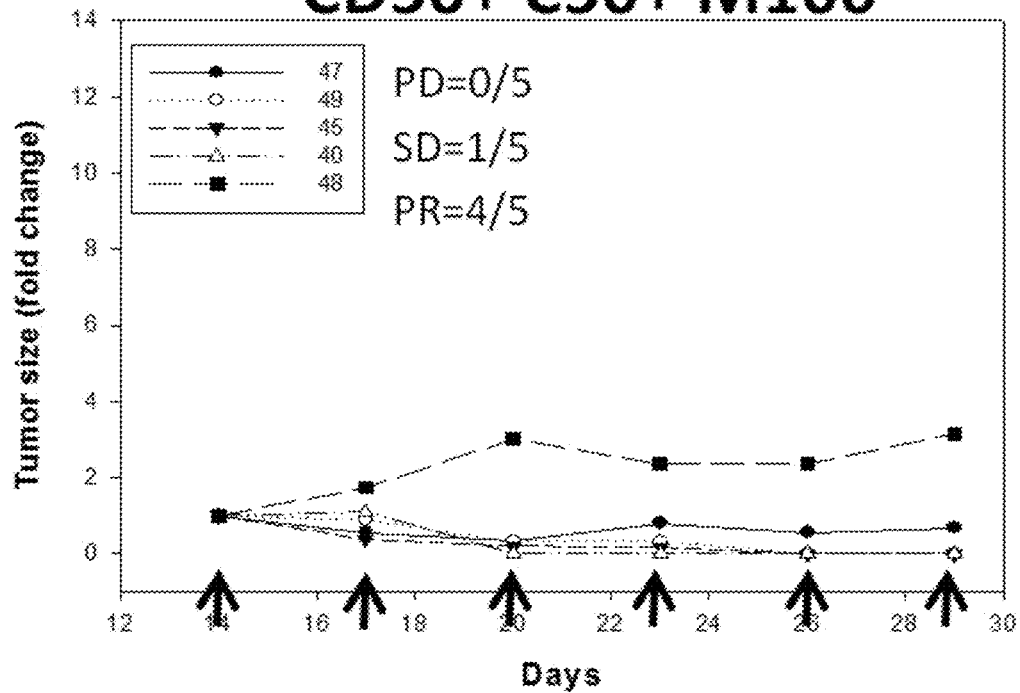
Figure 5C:
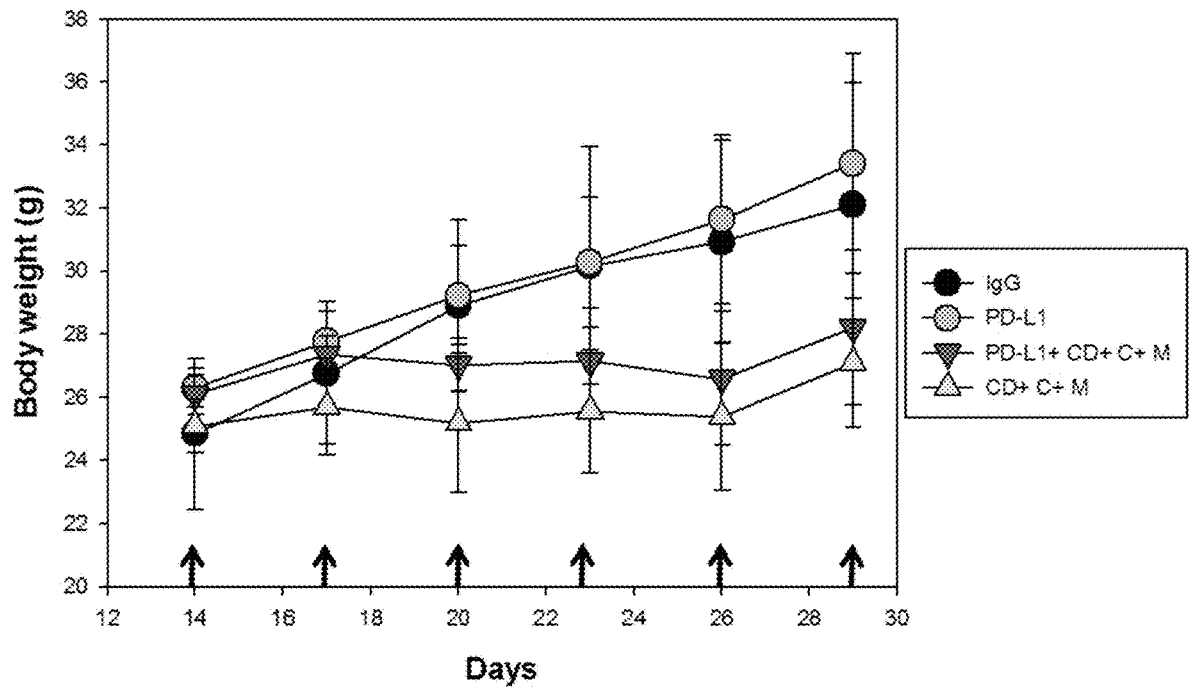
Figure 5D:
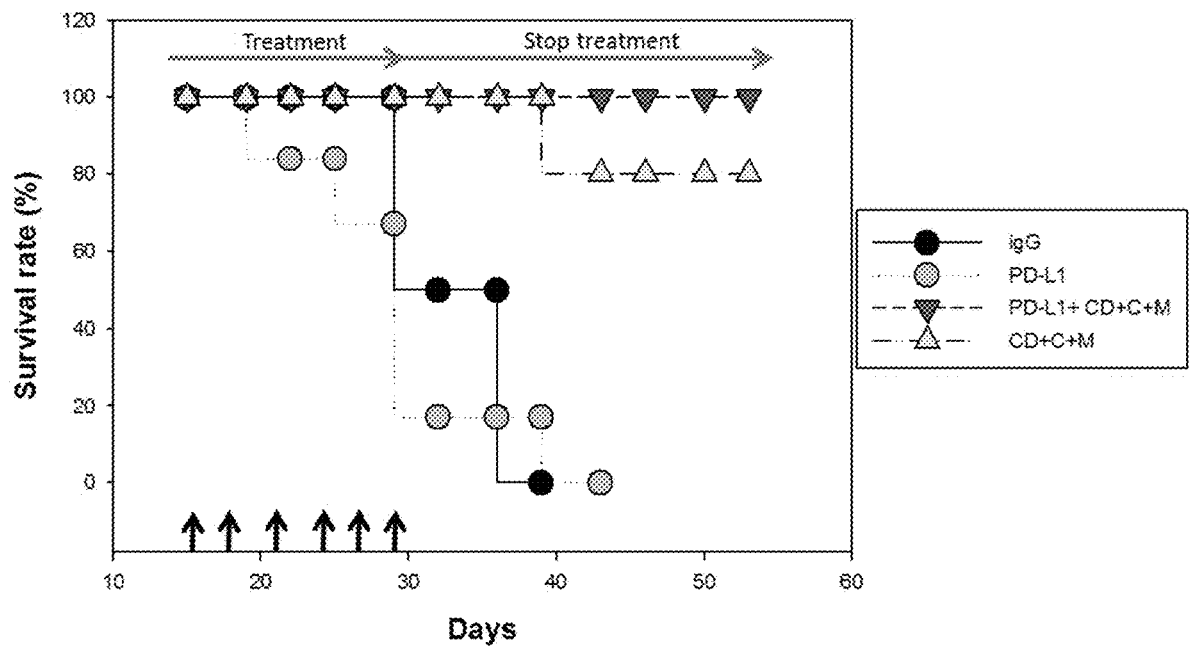

Example 5 Effects of Chidamide+Metformin+Celecoxib Combined with Anti-PD-L1 Antibody We have demonstrated that chidamide plus metformin and celecoxib combined with the anti-PD-1 antibody possesses a significant inhibition in tumor growth in the CT26-bearing mice (see FIG. 4). As shown in FIG. 5A, chidamide (50 mg/kg) plus metformin (100 mg/kg) and celecoxib (50 mg/kg) combined with the anti-PD-L1 antibody (10 mg/kg) was administered to the CT26-bearing mice. Chidamide, metformin, and celecoxib were administered daily. However, the anti-PD-L1 antibody was i.p. administered every 3 days. Our data shows that chidamide plus metformin and celecoxib is potent with regard to inhibiting tumor growth in the CT26-bearing mice (see FIG. 5A). We surprisingly found that chidamide plus metformin and celecoxib in the absence of anti-PD-L1 antibody significantly inhibits tumor growth in the CT26-bearing mice (FIG. 5A). The treatment with anti-PD-L1 (10 mg/kg) alone slightly inhibits tumor growth (FIG. 5A). From these results, it is shown that chidamide plus metformin and celecoxib possesses a powerful capacity to inhibit tumor growth. FIG. 5B shows that the chidamide plus metformin and celecoxib group and the chidamide plus metformin and celecoxib combined with the anti-PD-L1 antibody group significantly inhibit tumor growth and have high percentage of PR. As shown in FIG. 5C, all treatment regimens did not cause any loss of body weight. As shown in FIG. 5D, chidamide combined with metformin and celecoxib significantly increases the survival rate to about 80%. This result shows that chidamide combined with metformin and celecoxib was highly effective in the control of a tumor microenvironment and triggering immunotherapy. Moreover, chidamide plus metformin and celecoxib combined with anti-PD-L1 antibody is more powerful to inhibit tumor growth and achieves a 100% survival rate at day 53. At day 53, the survival rates were similar between these two regimens. The results indicate that chidamide combined with metformin and celecoxib possesses potent tumor growth inhibitory activity. The combination with the anti-PD-L1 antibody increased inhibition on tumor growth and survival rate (FIG. 5D).

Figure 6A:
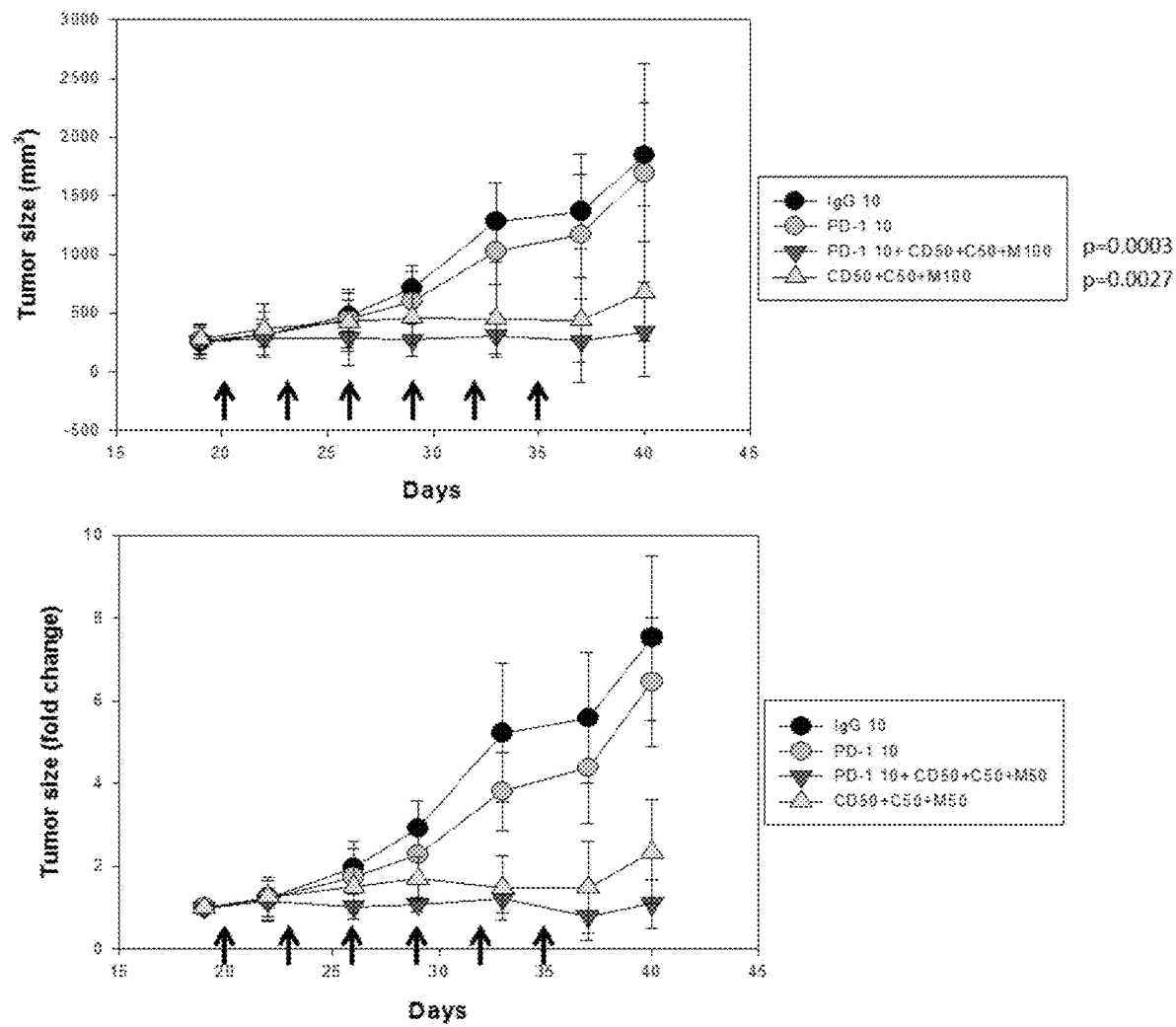
FIGS. 6 A to D show the therapeutic response of chidamide plus metformin and celecoxib combined with anti-PD-1 antibody in JC tumor-bearing mice. BALB/c mice bearing a JC breast tumor was treated with various therapeutic modalities as indicated. IgG, Anti-IgG control (vehicle, 10 mg/kg); PD-1, Anti-PD-1 monoclonal antibody (10 mg/kg); CD, chidamide (50 mg/kg); C, celecoxib (50 mg/kg); M, metformin (100 mg/kg). Total tumor volumes (A), individual tumor volumes (B), JC tumor bearing-mice body weight (C), and animal survival (D) were recorded. JC tumor bearing mice were treated as indicated and euthanized at tumor volume of 3,000 mm$^3$ after tumor implantation. Means and SDs are shown. The number of animals used in each experimental arm and P values are also indicated.*P<0.05. P-values were calculated using Student's t-test that compared tumor size at indication group with IgG group.
Figure 6B:
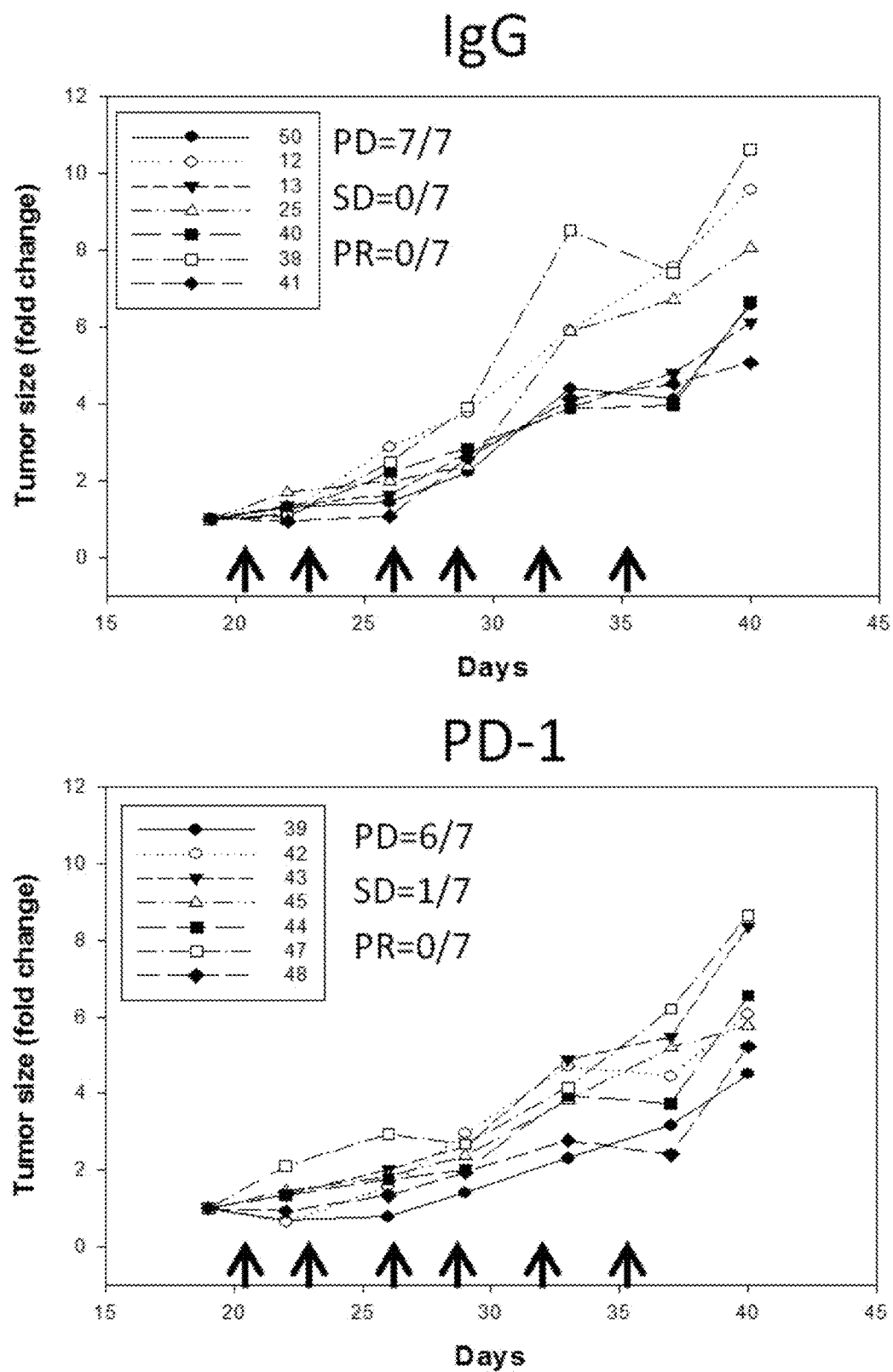
Figure 6B:
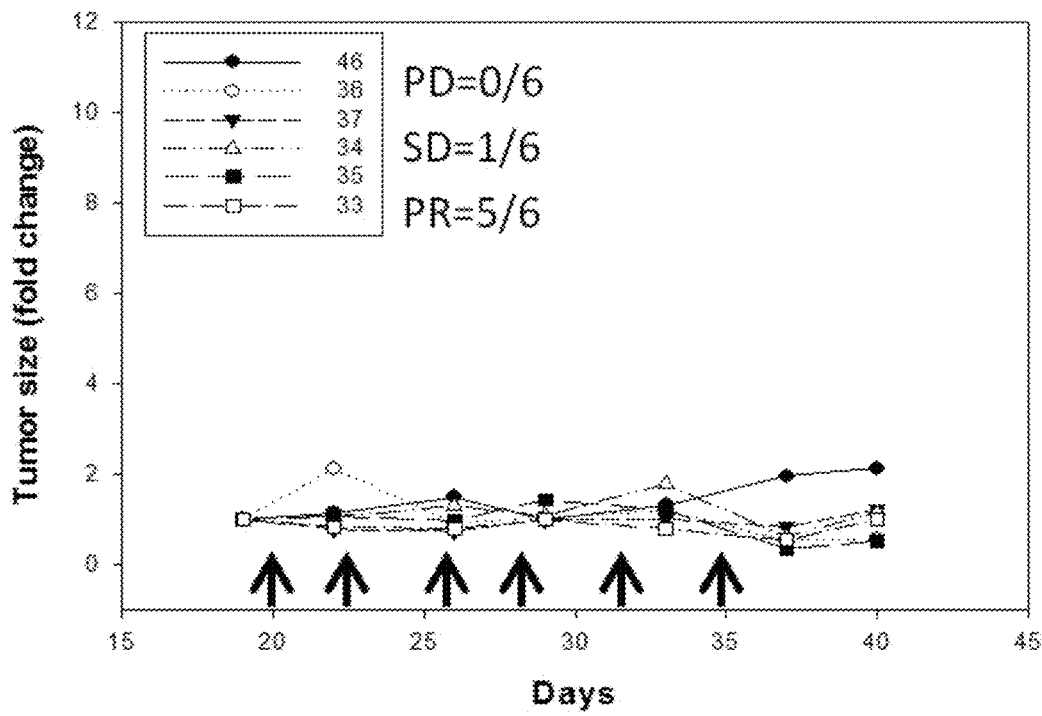
Figure 6B:
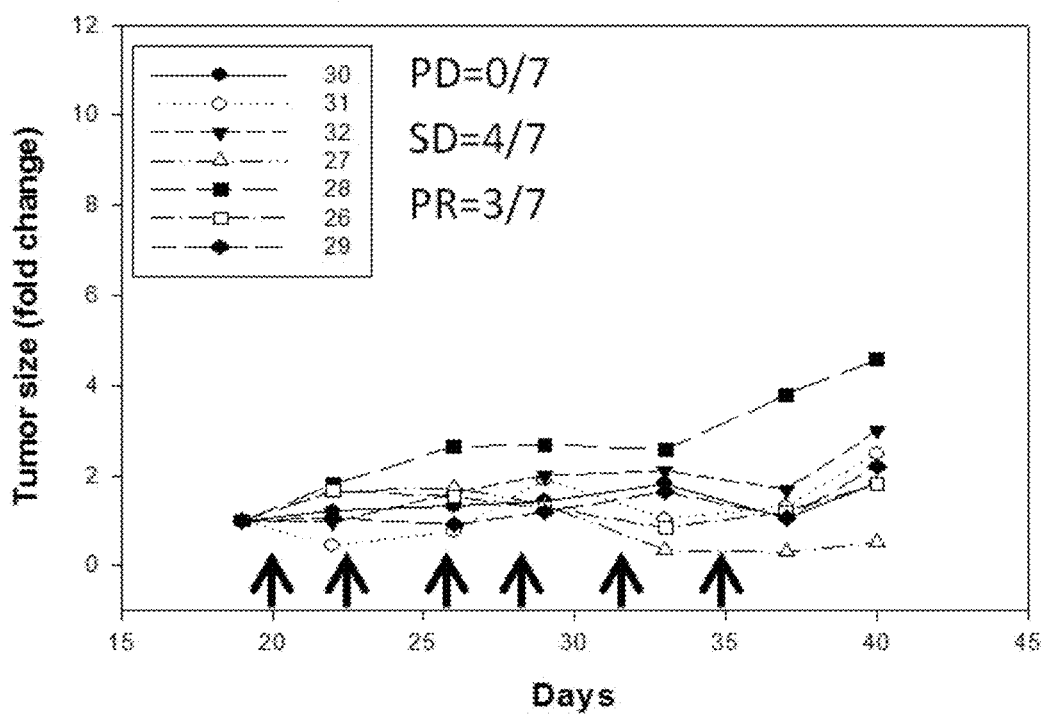
Figure 6C:
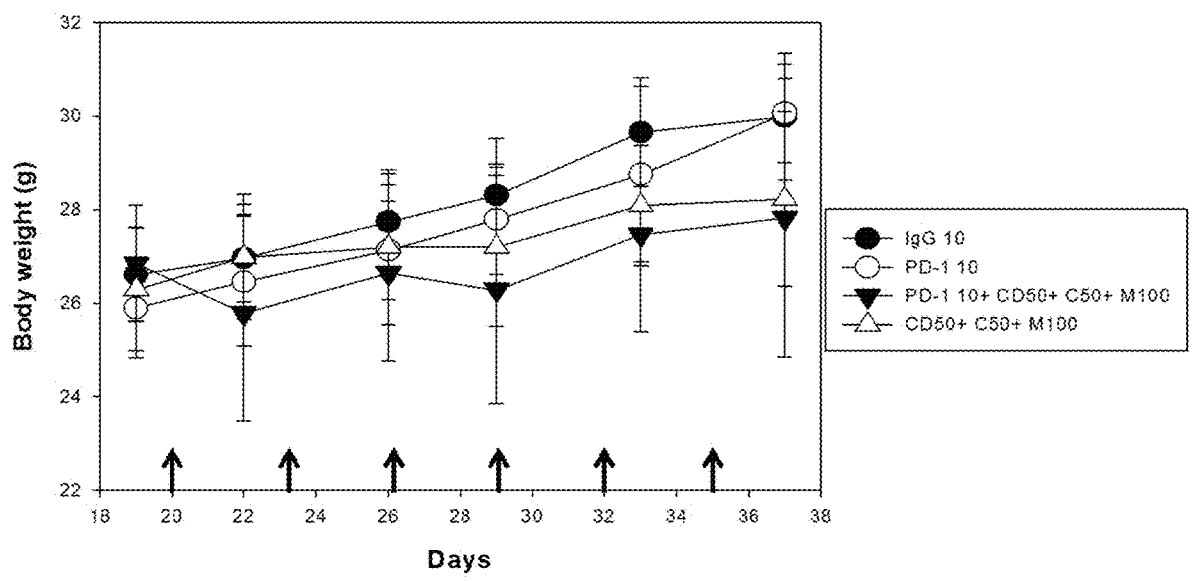
Figure 6D:
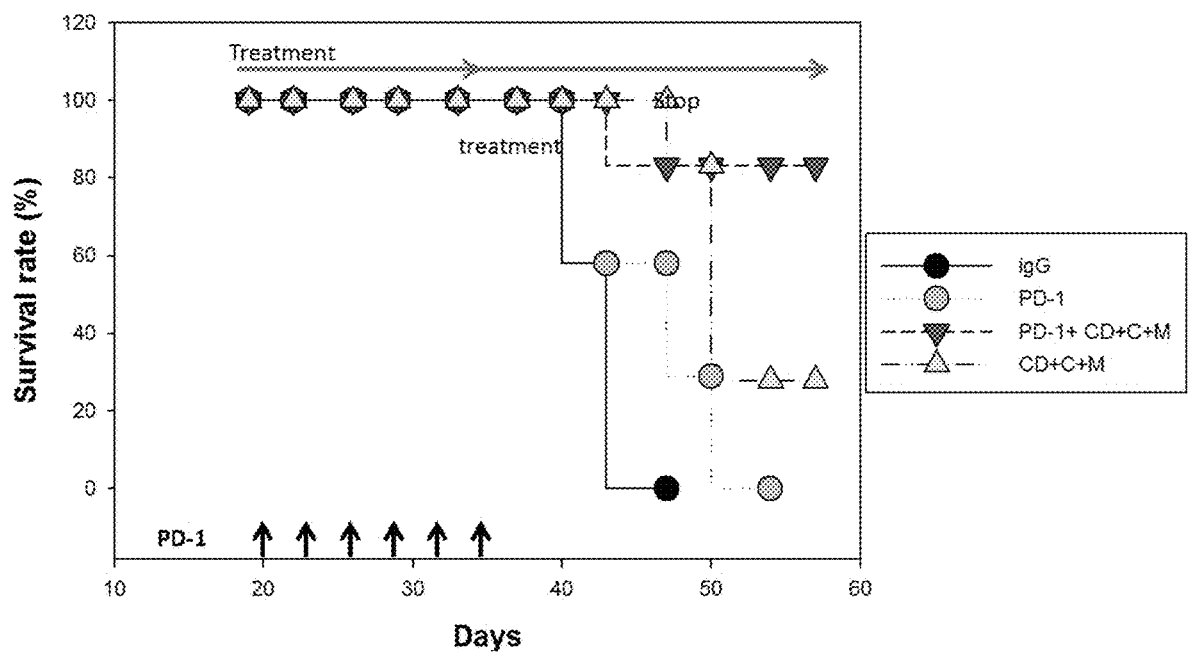

Example 6 Effects of Chidamide+Metformin+Celecoxib Combined with the Anti-PD-1 Antibody in JC-Bearing Mice The JC cell line was obtained from malignant neoplasms of the mouse mammary gland. We were interested in evaluating whether any tumor inhibition could be found in JC-bearing mice. As shown in FIG. 6, JC cells grew slower than CT26 cells in mice; therefore, the tumor size in the JC-bearing mice grew to about 300-400 $mm^3$ at day 20. Chidamide plus metformin and celecoxib significantly inhibits tumor growth in the JC-bearing mice (FIG. 6A). However, chidamide plus metformin and celecoxib combined with the anti-PD-1 antibody is even more effective in inhibiting tumor growth in the JC-bearing mice (FIG. 6A). This regimen significantly inhibits tumor growth in both CT26-bearing mice and the JC-bearing mice. We first found that chidamide combined with metformin plus celecoxib possesses a potent immune therapy activity in inhibiting tumor in normal immunity tumor bearing mice. Moreover, as shown in FIG. 6B, the anti-PD-1 antibody only has slight anti-cancer activity and SD was observed in only one mouse. Chidamide plus metformin and celecoxib regimen potently inhibits tumor growth; however, it has lower inhibitory effect than Chidamide plus metformin and celecoxib combined with anti-PD-1 antibody regimen. In the chidamide plus metformin and celecoxib group, three mice achieved PR and SD was observed in four mice. However, in the chidamide plus metformin and celecoxib combined with anti-PD-1 antibody group, five mice were PR and one mouse was SD. Given the above, chidamide plus metformin and celecoxib regimen possesses potent antitumor growth. After combining with anti-PD-1 or anti-PD-L1 antibody, the inhibition of tumor growth in CT26-bearing or JC-bearing mice models is increased (FIG. 5B and FIG. 6B). As shown in FIG. 6C, none of the mice in the treatment groups lost any body weight. As shown in FIG. 6D, chidamide combined with metformin and celecoxib significantly increases the survival rate to about 28% in comparison with the anti-PD-1 antibody group in the JC-bearing tumor mice model. The result proves that the chidamide plus metformin, and celecoxib regimen is a good combination against cancer. The regimen can control a tumor microenvironment and boost immunotherapy. Furthermore, chidamide plus metformin and celecoxib combined with the anti-PD-1 antibody is more potent to inhibit tumor growth and increases the survival rate to around 83%. After the treatment was stopped at day 35, the tumor in the CT26-bearing and JC-bearing tumor mice grew faster in the IgG control group. However, chidamide plus metformin and celecoxib, combined with an immune checkpoint inhibitor regimen, was very potent in inhibiting tumor growth and thus significantly increased survival rates (FIG. 6D).

Figure 7A:
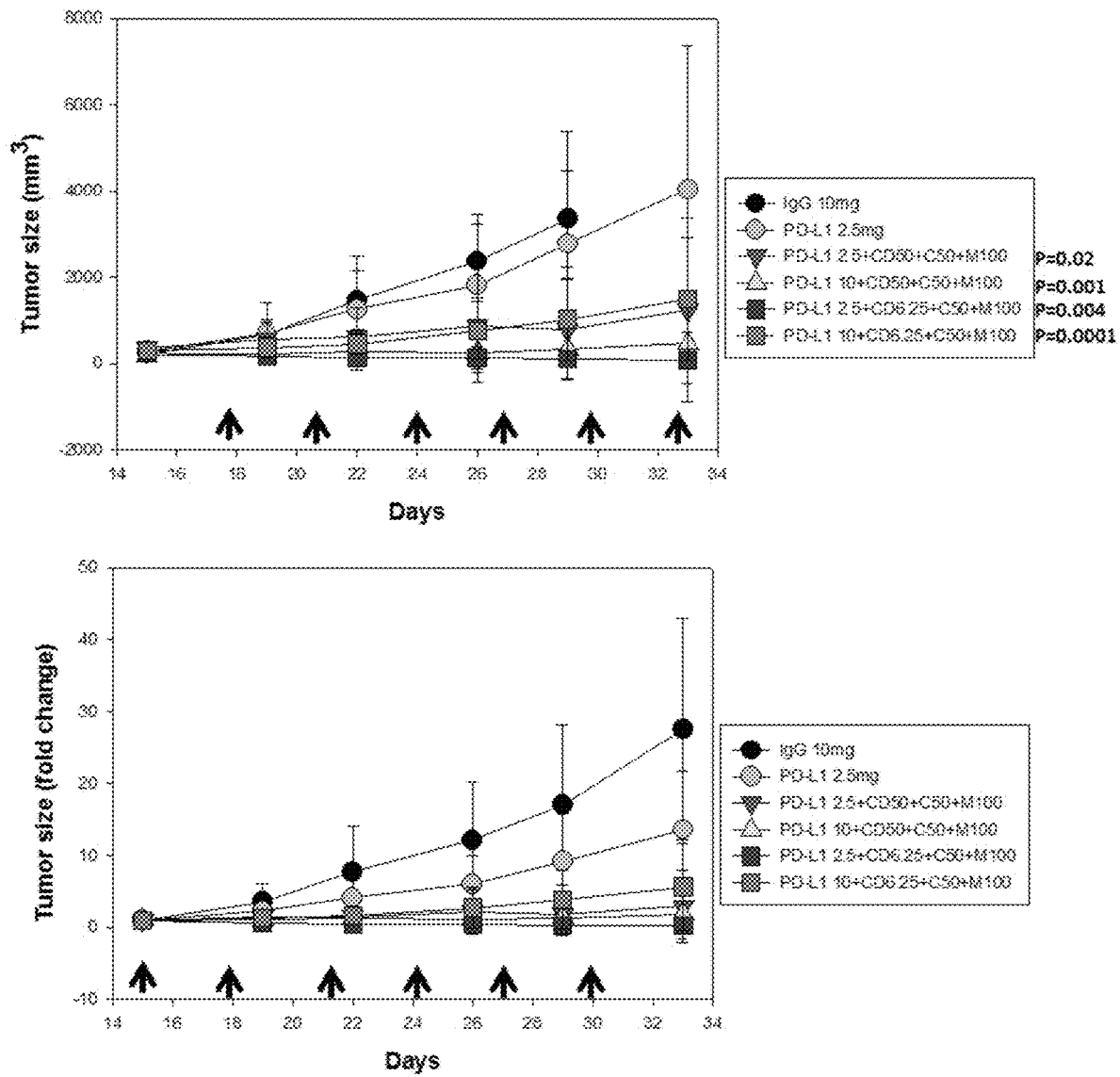
FIGS. 7 A to E show the therapeutic response of chidamide (at different doses) plus metformin and celecoxib combined with or without anti-PD-L1 antibody (at different doses) in CT26 tumor-bearing mice. BALB/c mice bearing a CT26 colon tumor were treated with various therapeutic modalities as indicated. IgG, Anti-IgG control (vehicle, 10 mg/kg); PD-L1, Anti-PD-L1 monoclonal antibody (2.5 and 10 mg/kg); CD, chidamide (6.25, 12.5, or 50 mg/kg); C, celecoxib (50 mg/kg); M, metformin (100 mg/kg). The total tumor volumes of after treatment with anti-PD-L1 antibody (2.5 or 10 mg/kg) and chidamide (6.25 or 50 mg/kg) plus celecoxib (50 mg/kg) and metformin (100 mg/kg) (A), the total tumor volumes after treatment with chidamide (6.25, 12.5 or 50 mg/kg) plus celecoxib (50 mg/kg) and metformin (100 mg/kg) in the absence of anti-PD-L1 antibody (B), individual total tumor volumes after treatment with chidamide (6.25, 12.5 or 50 mg/kg) plus celecoxib (50 mg/kg) and metformin (100 mg/kg) in the presence (2.5 or 10 mg/kg) or absence of anti-PD-L1 antibody (C), CT26 tumor-bearing mice body weight (D), and animal survival (E) were recorded. CT26 tumor bearing mice were treated as indicated and euthanized at tumor volume of 3,000 mm$^3$ after tumor implantation. Means and SDs are shown. The number of animals used in each experimental arm and P values are also indicated.*P<0.05. P-values were calculated using Student's t-test that compared tumor size at indication group with IgG group.
Figure 7B:
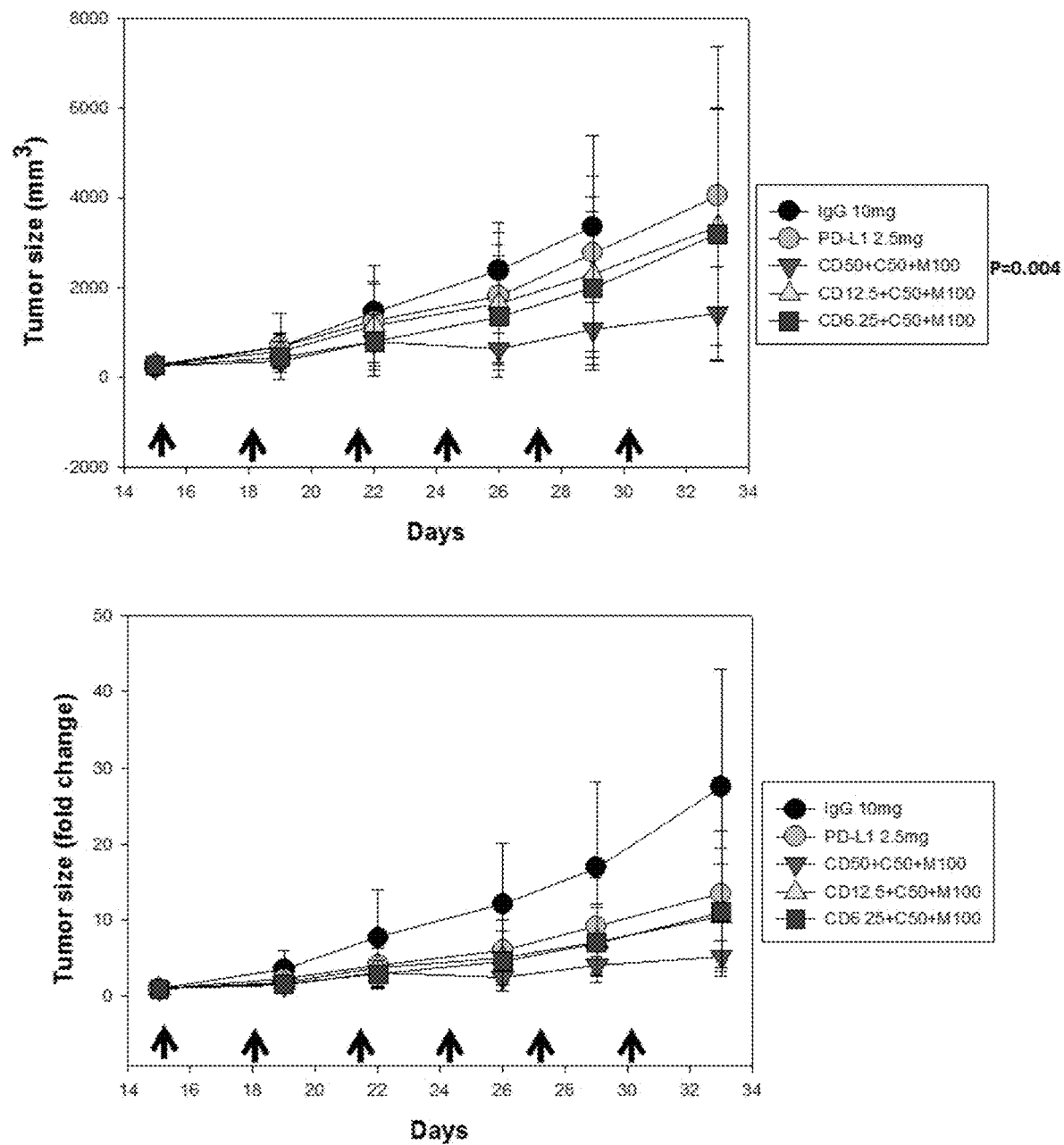
Figure 7C:
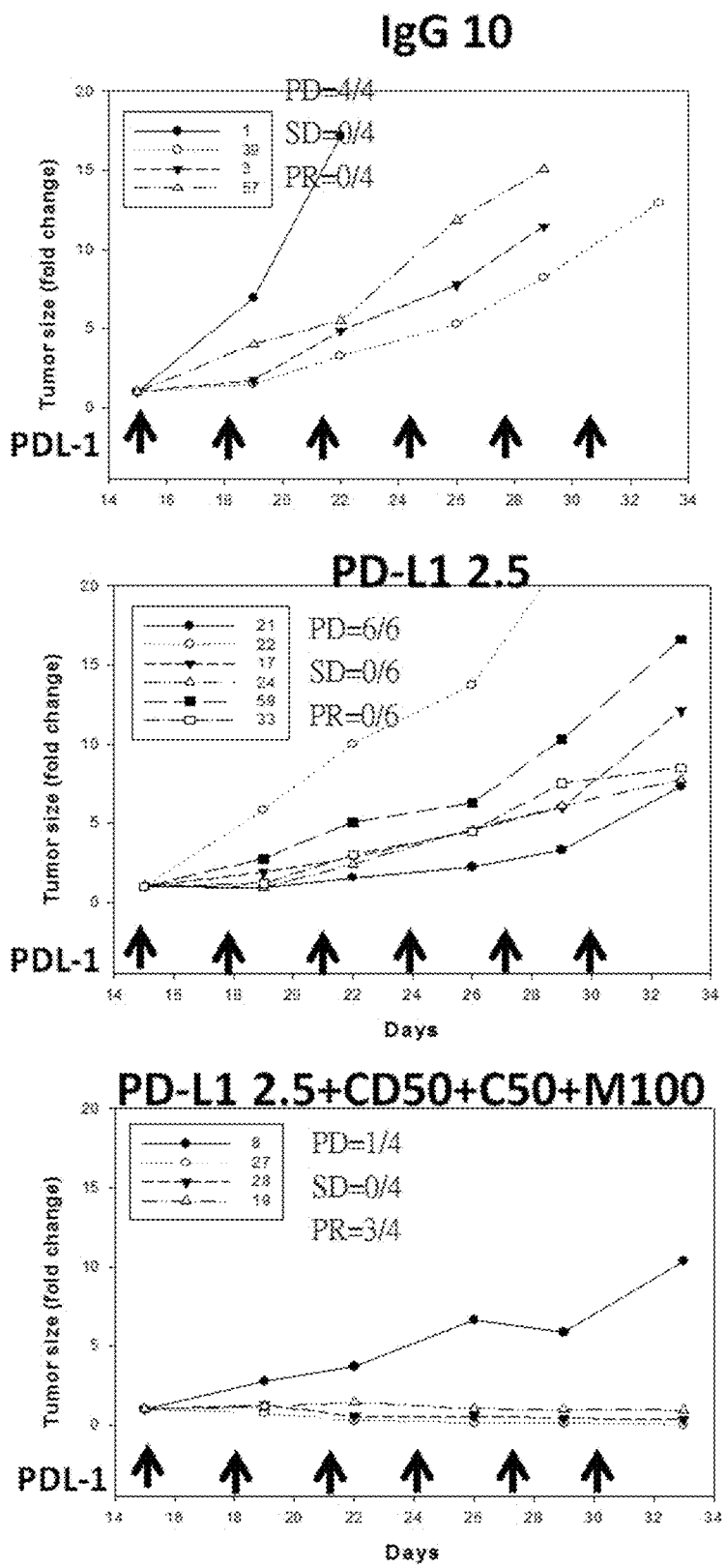
Figure 7C:
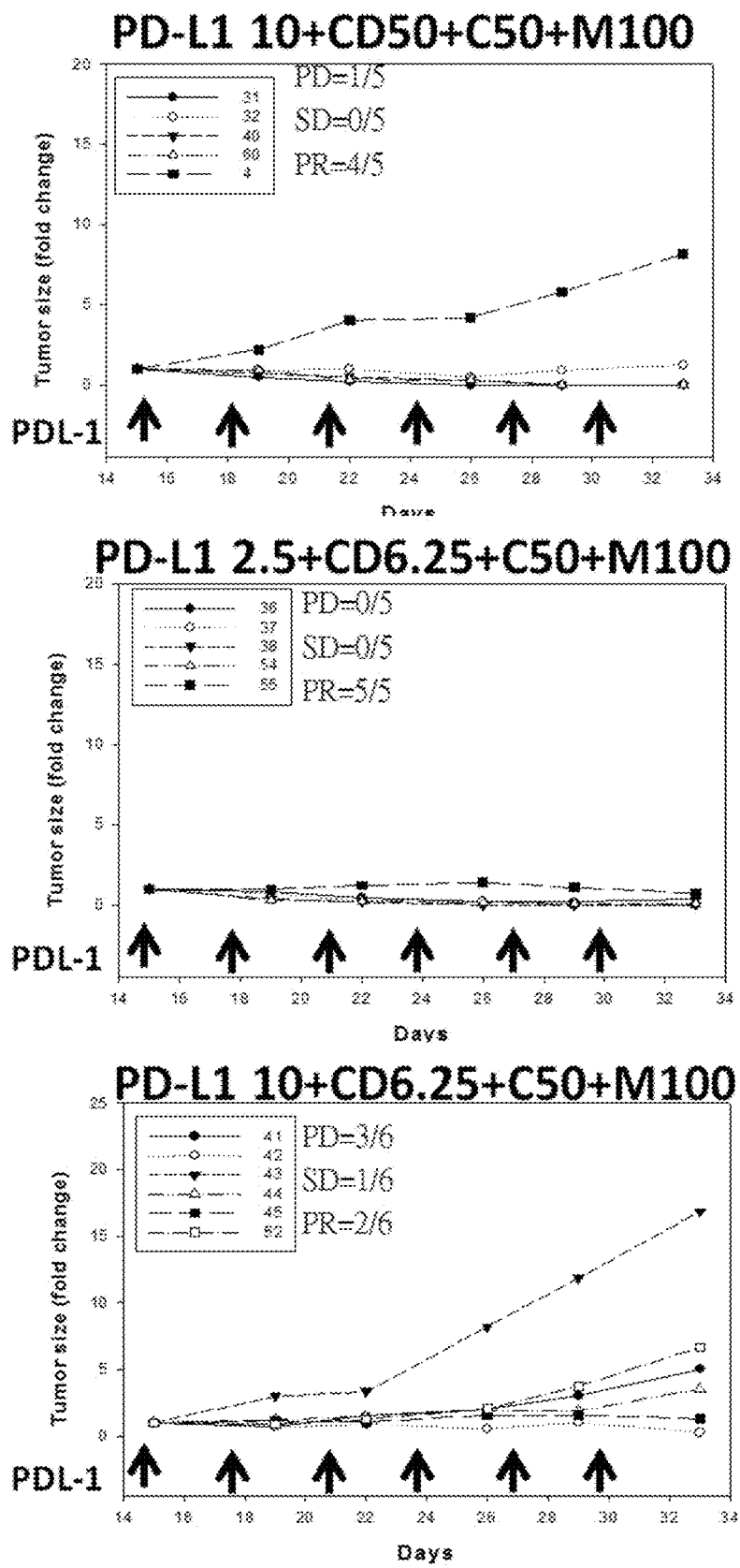
Figure 7C:
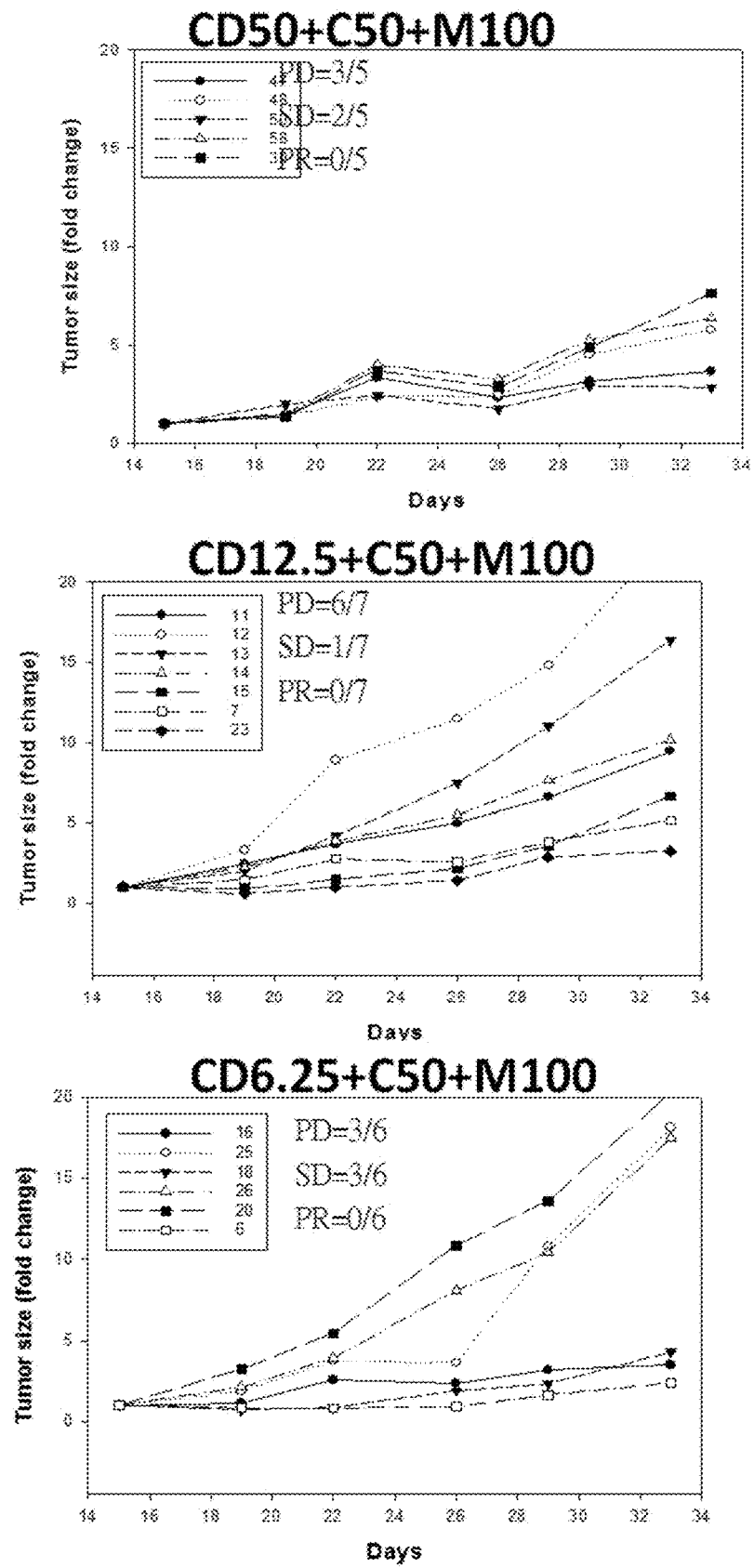
Figure 7D:
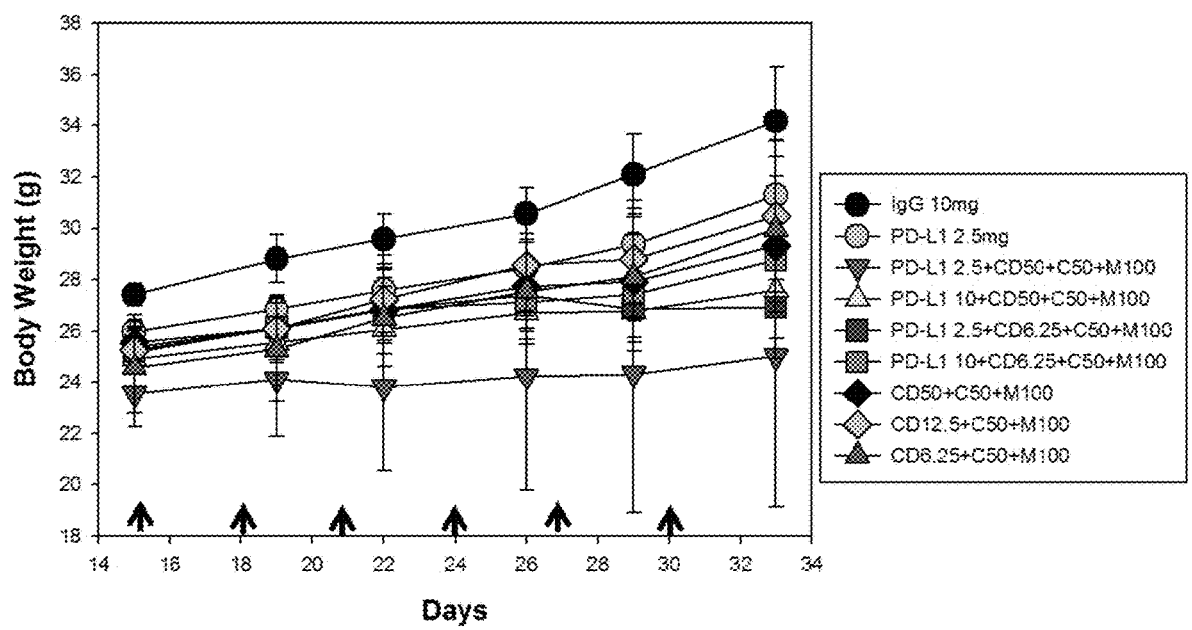
Figure 7E:
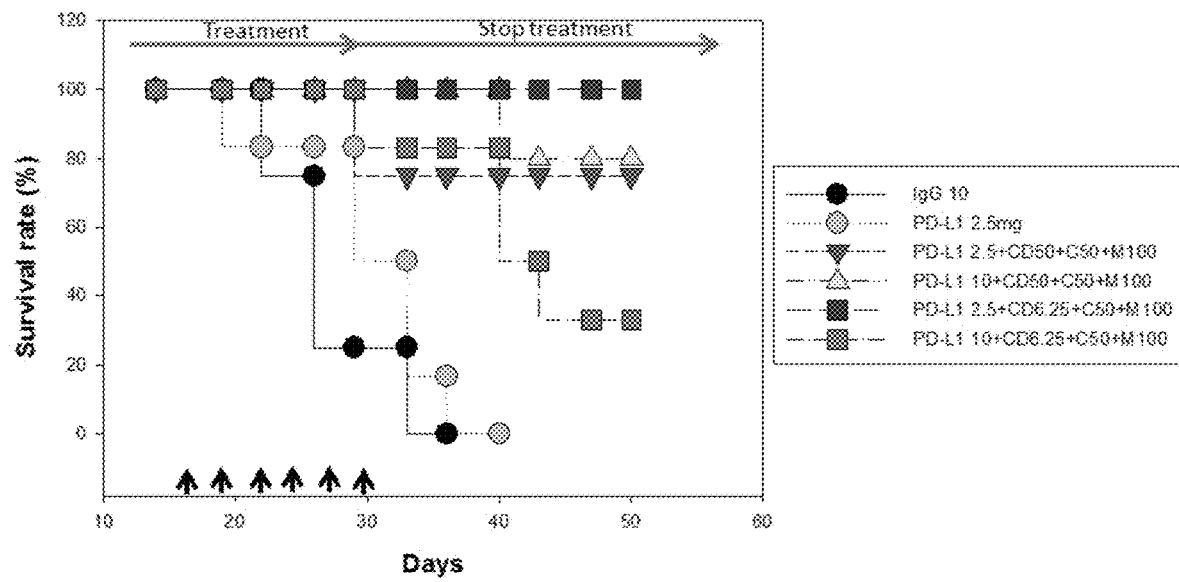
Figure 7E:
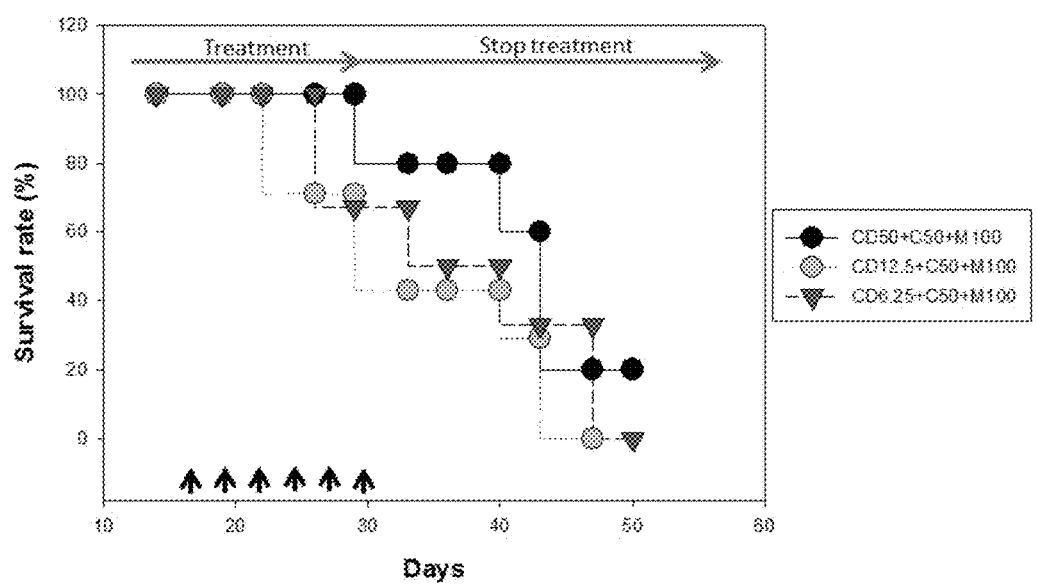

Example 7 Effects of Chidamide Plus Metformin and Celecoxib Combined with or without Anti-PD-L1 Antibody (Low Dose or High Dose) in CT26-Bearing Mice We were interested in evaluating whether reducing the dosage of an anti-PD-L1 antibody immune checkpoint inhibitor still performed tumor inhibition in CT26-bearing mice. As shown in FIG. 7, the tumor size in the CT26-bearing mice grew to about 250-300 mm$^3$ at day 15. Chidamide 50 mg/kg plus metformin 100 mg/kg and celecoxib 50 mg/kg combined with PD-L1 (2.5 or 10 mg/kg) significantly inhibits tumor growth in the CT26-bearing mice (FIG. 7A). There is no significant difference in the inhibition of tumor growth in the CT26-bearing mice between 2.5 mg/kg and 10 mg/kg anti-PD-L1 antibody groups. On the other hand, chidamide at a low dosage of 6.25 mg/kg or at a high dosage of 50 mg/kg plus metformin 100 mg/kg and celecoxib 50 mg/kg combined with anti-PD-L1 antibody (2.5 or 10 mg/kg) significantly inhibits tumor growth in the CT26-bearing mice (FIG. 7A). Chidamide groups at two dosages of 6.25 and 50 mg/kg showed no statistically significant difference in inhibition of tumor growth in the CT26-bearing mice, regardless of the presence of low or high dosage of anti-PD-L1 antibody (2.5 or 10 mg/kg). However, chidamide at various doses of 6.25, 12.5, and 50 mg/kg plus metformin 100 mg/kg and celecoxib 50 mg/kg in the absence of anti-PD-L1 antibody also markedly possess inhibitory activity of tumor growth as shown in FIG. 7B. The result demonstrated that chidamide 50 mg/kg plus metformin 100 mg/kg and celecoxib 50 mg/kg group significantly inhibits tumor growth in the CT26-bearing mice as compared to the IgG vehicle group (FIG. 7B). This result also demonstrated that chidamide at various doses combined with celecoxib 50 mg/kg plus metformin 100 mg/kg possessed unique immunomodulating activities, which could markedly influence the tumor microenvironment to reactivate cytotoxic T-lymphocytes to attack tumor cells and finally cause the inhibition of tumor growth (FIG. 7B). Furthermore, the results of all the mice treated with different therapeutic modalities are shown in FIG. 7C. It was demonstrated that treatment with 2.5 mg/kg anti-PD-L1 antibody was not potent enough to reactivate cytotoxic T-lymphocytes to kill tumor cells. For chidamide plus celecoxib and metformin groups, the results demonstrated that high dose (50 mg/kg) of chidamide was needed to reactivate cytotoxic T-lymphocytes to kill tumor cells. Treatment with high dose (10 mg/kg) or low dose (2.5 mg/kg) of anti-PD-L1 antibody combined with chidamide plus celecoxib and metformin significantly inhibited tumor growth. The treatment with anti-PD-L1 antibody (2.5 mg/kg) combined with chidamide 50 mg/kg plus celecoxib 50 mg/kg and metformin 100 mg/kg was shown to have the most potent anti-cancer activity in FIG. 7C. There is no significant difference in anti-cancer activity between low (2.5 mg/kg) and high (10 mg/kg) dose of anti-PD-L1 antibody treatment. These results suggested that in combination with chidamide plus celecoxib and metformin plus anti-PD-L1 antibody is required for potent anti-tumor ability in CT26-bearing mice model. As shown in FIG. 7D, none of the mice in the treatment groups lost any body weight. The survival rate results were indicated in FIG. 7E. First, treatment with chidamide 50 mg/kg combined with metformin 100 mg/kg and celecoxib 50 mg/kg significantly increases the survival rate to about 20% in comparison with treatment with anti-PD-L1 antibody alone. The result proves that chidamide plus metformin and celecoxib regimen is a good combination and possesses immunomodulating activity. The regimen can control tumor microenvironment and boost therapeutic efficacy. Second, treatment with chidamide 50 mg/kg plus metformin 100 mg/kg and celecoxib 50 mg/kg combined with anti-PD-L1 antibody 2.5 mg/kg is more potent to inhibit tumor growth and increases the survival rate to around 75%. A similar result was also shown in treatment with chidamide 50 mg/kg plus metformin 100 mg/kg and celecoxib 50 mg/kg combined with anti-PD-L1 antibody 10 mg/kg (the survival rate around 80%). Third, chidamide 6.25 mg/kg plus metformin 100 mg/kg and celecoxib 50 mg/kg combined with the anti-PD-L1 10 mg/kg antibody markedly inhibits tumor growth and increases the survival rate to around 40%. But, Chidamide 6.25 mg/kg plus metformin 100 mg/kg and celecoxib 50 mg/kg combined with the anti-PD-L1 2.5 mg/kg antibody is more potent to inhibit tumor growth and increases the survival rate to around 100%. After the treatment was stopped at day 30, the tumor in the CT26-bearing tumor mice grew faster in the IgG control group. However, chidamide 50 mg/kg plus metformin 100 mg/kg and celecoxib 50 mg/kg, combined with anti-PD-L1 Ab (2.5 or 10 mg/kg) regimens, were very potent in inhibiting tumor growth and thus significantly increased survival rate as compared to chidamide 50 mg/kg combined with celecoxib 50 mg/kg plus metformin 100 mg/kg regimen as shown in FIG. 7E.

Figure 8A:
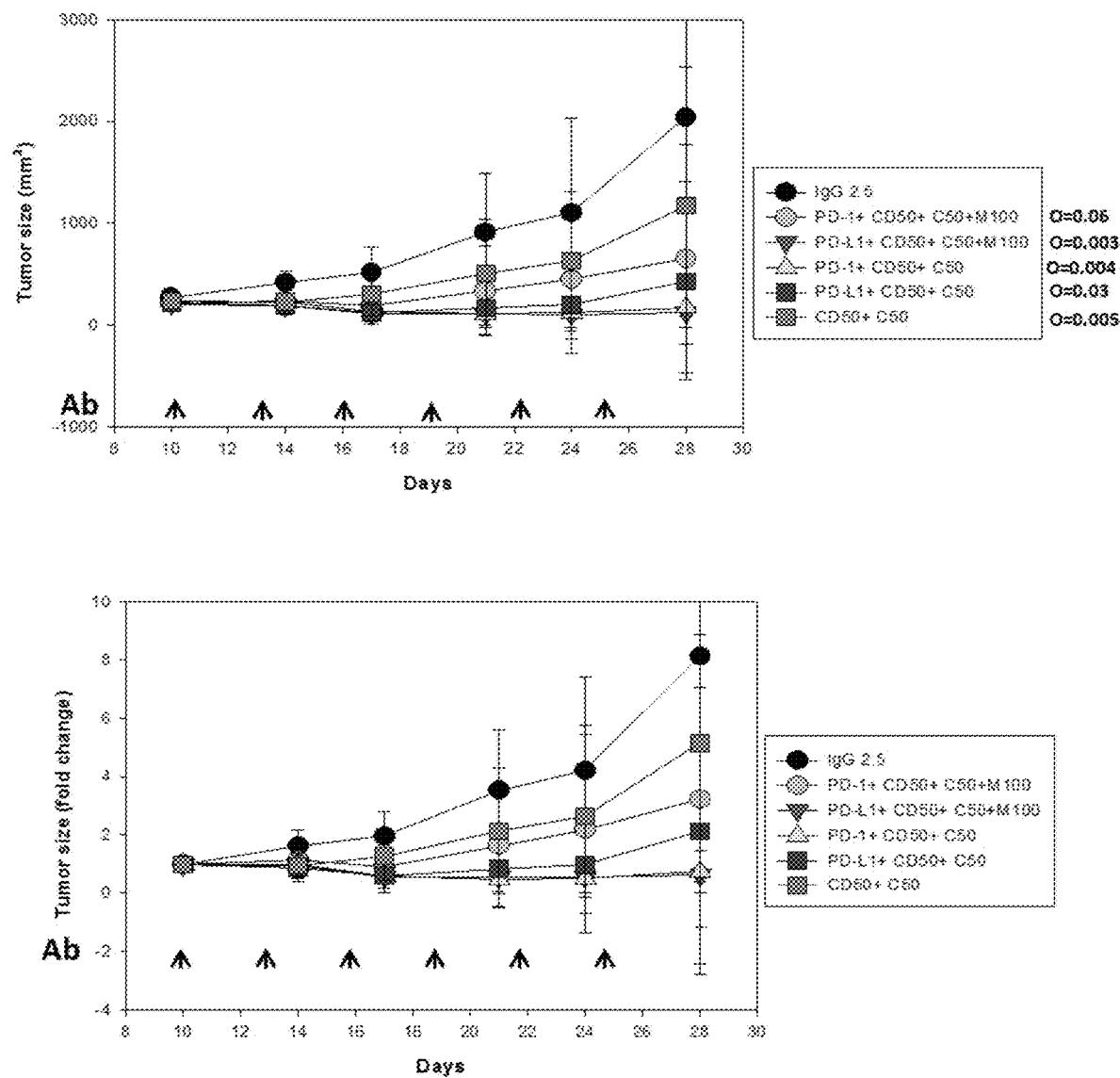
FIGS. 8 A to E show the therapeutic response of anti-PD-1 or anti-PD-L1 antibody combined with chidamide plus celecoxib with or without metformin in CT26 tumor-bearing mice. BALB/c mice bearing a CT26 colon tumor were treated with various therapeutic modalities as indicated. IgG, Anti-IgG control (vehicle, 2.5 mg/kg); PD-1, Anti-PD-1 monoclonal antibody (2.5 mg/kg); PD-L1, Anti-PD-L1 monoclonal antibody (2.5 mg/kg); CD, chidamide (50 mg/kg); C, celecoxib (50 mg/kg); M, metformin (100 mg/kg). The total tumor volumes after treatment with chidamide (50 mg/kg) plus celecoxib (50 mg/kg) with or without metformin (100 mg/kg) in the presence or absence of anti-PD-1/anti-PD-L1 antibody (A), the total tumor volumes after treatment with anti-PD-1 or anti-PD-L1 antibody combined with chidamide (50 mg/kg) plus celecoxib (50 mg/kg) and metformin (100 mg/kg) compared to those of anti-PD-1 or anti-PD-L1control groups (B), individual tumor volumes after treatment with various therapeutic modalities as indicated (C), CT26 tumor-bearing-mice body weight (D), and animal survival (E) were recorded. CT26 tumor bearing mice were treated as indicated and euthanized at tumor volume of 3,000 mm$^3$ after tumor implantation. Means and SDs are shown. The number of animals used in each experimental arm and P values are also indicated.*P<0.05. P-values were calculated using Student's t-test that compared tumor size at indication group with IgG group.
Figure 8B:
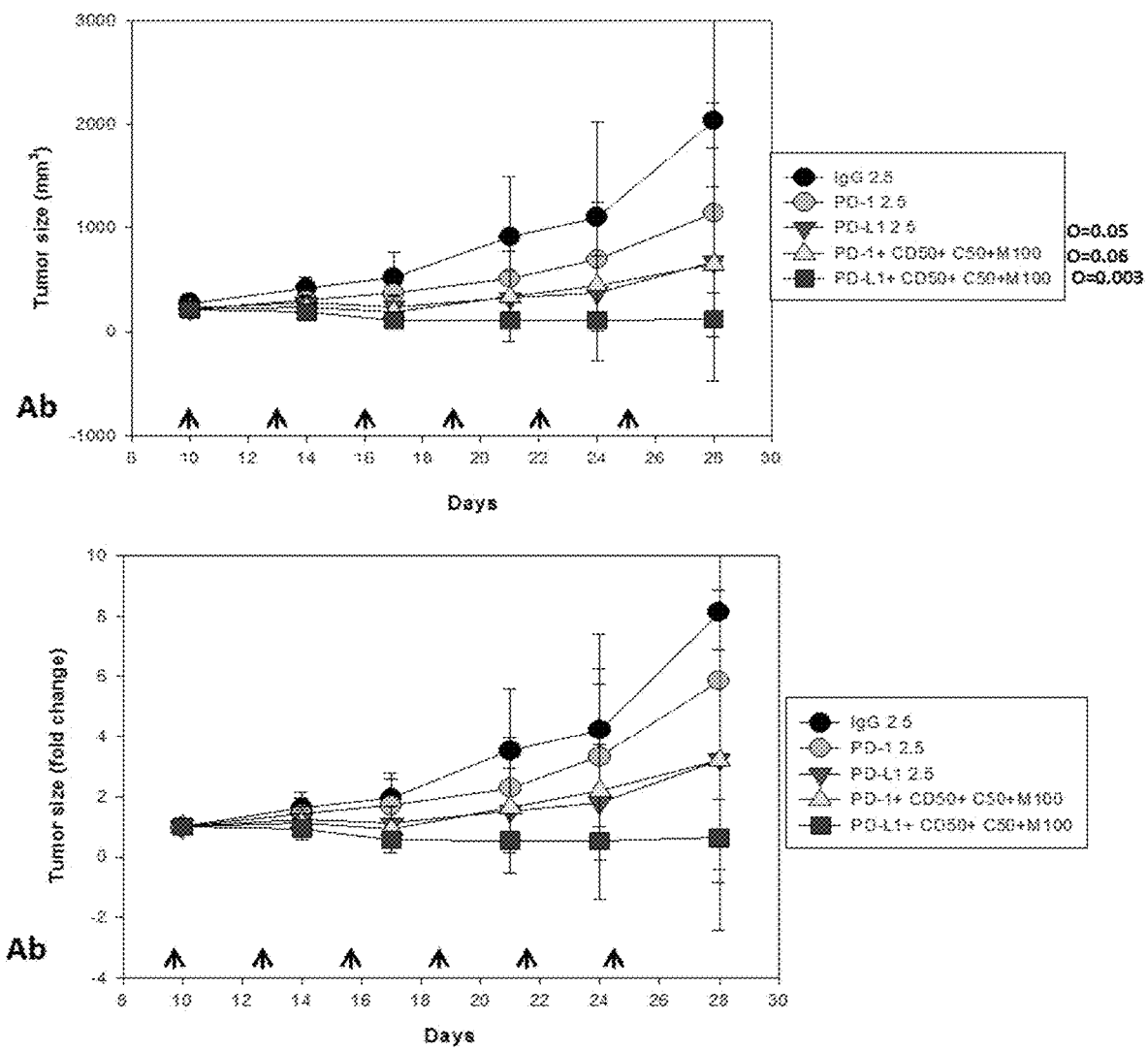
Figure 8C:
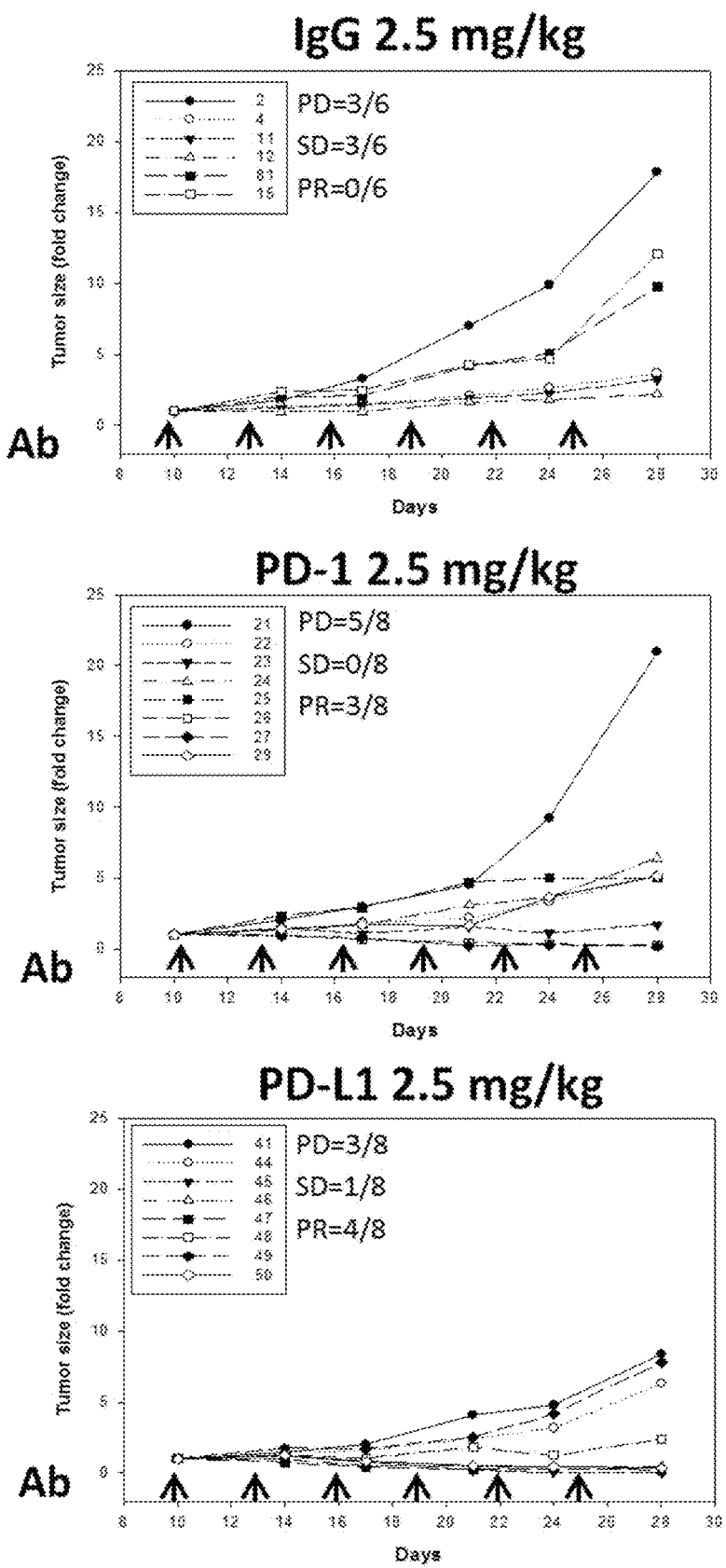
Figure 8C:
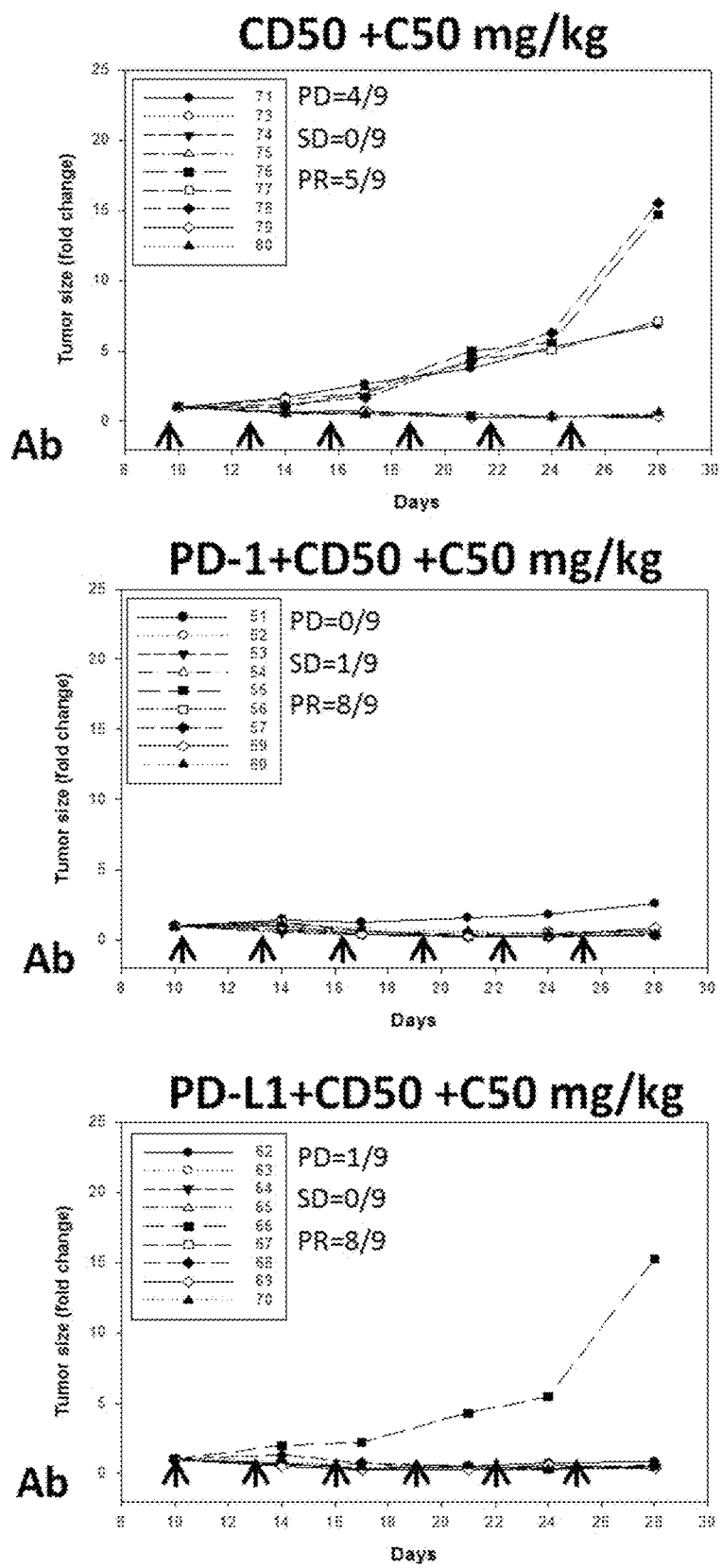
Figure 8D:
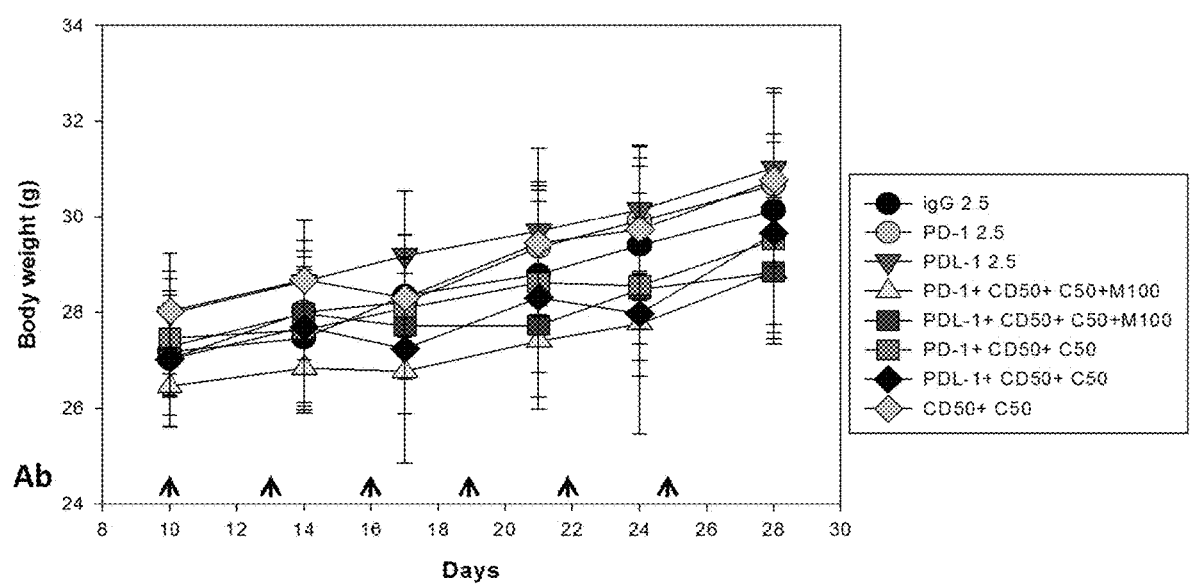
Figure 8E:
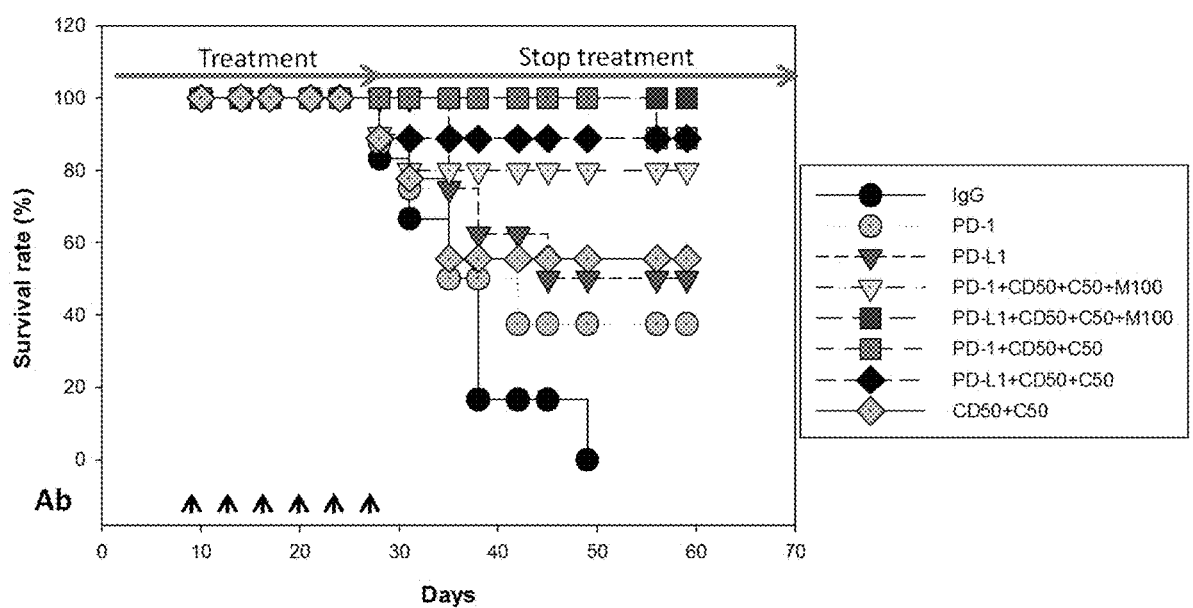

Example 8 Head to Head Comparison of the Effects of Anti-PD-1 and Anti-PD-L1 Ab in Combination with Chidamide Plus Celecoxib with or without Metformin in CT26-Bearing Mice Next, we were interested in evaluating the therapeutic effects of anti-PD-1 or anti-PD-L1 antibody in combination with chidamide plus celecoxib combined with or without metformin in CT26-bearing mice. As shown in FIG. 8, the tumor size in the CT26-bearing mice grew to about 200-250 mm$^3$ at day 10. First, combination of chidamide 50 mg/kg plus celecoxib 50 mg/kg without metformin significantly inhibited tumor growth in the CT26-bearing mice in comparison with the IgG group (FIG. 8A). Second, chidamide 50 mg/kg plus celecoxib 50 mg/kg combined with the anti-PD-1 antibody 2.5 mg/kg is even more effective in inhibiting tumor growth in the CT26-bearing mice (FIG. 8A). Third, a similar result was also found in chidamide 50 mg/kg plus celecoxib 50 mg/kg combined with the anti-PD-L1 antibody 2.5 mg/kg treatment. FIGS. 8A and 8B show that chidamide 50 mg/kg combined with celecoxib 50 mg/kg was enough to influence the tumor microenvironment and reactivate cytotoxic T-lymphocytes to kill the tumor. On the other hand, head to head comparison of the anti-cancer effects of low dose (2.5 mg/kg) of anti-PD-1 and anti-PD-L1 antibody in combination with chidamide 50 mg/kg plus celecoxib 50 mg/kg showed potency of tumor inhibition in CT26-bearing mice as shown in FIGS. 8A and B. These results from the head to head study suggested that immune checkpoint inhibitor anti-PD-1 or anti-PD-L1 antibody is required in combination treatment with chidamide plus celecoxib for potent anti-tumor ability in CT26-bearing mice model. This finding also demonstrated that the dosage of anti-PD-1 or anti-PD-L1 antibody can be reduced to ¼ (2.5 mg/kg) of recommended dose 10 mg/kg, when combined with chidamide 50 mg/kg plus celecoxib 50 mg/kg for potent reactivation of cytotoxic T-lymphocytes in the tumor microenvironment to inhibit tumor growth as shown in FIGS. 8A and B. The study has proven that the regimen of anti-PD-1 or anti-PD-L1 antibody combined with chidamide plus celecoxib was enough for the execution of potent anti-tumor activities. From these results it can be concluded that metformin may play a minor role in the regulation of immunity in the tumor microenvironment. The suitable regimen is chidamide plus celecoxib combined with an immune checkpoint inhibitor such as anti-PD-1 or anti-PD-L1 antibody. The anti-cancer effects of various therapeutic modalities in all of the mice are shown in FIG. 8C. The treatment with anti-PD-1 antibody alone only had slight anti-cancer activity and only three mice achieved PR (response rate 37.5%). Chidamide plus celecoxib regimen showed better anti-tumor activity, and five mice achieved PR (response rate 55.5%); however, it showed lower inhibitory effect than chidamide 50 mg/kg plus celecoxib 50 mg/kg with or without metformin 100 mg/kg combined with anti-PD-1 antibody regimen. On the chidamide plus celecoxib combined with anti-PD-1 antibody group, eight mice achieved PR (response rate 88%). In the anti-PD-L1 antibody group it showed slight anti-cancer activity and only four mice achieved PR (response rate 50%). In chidamide 50 mg/kg plus metformin 100 mg/kg and celecoxib 50 mg/kg combined with anti-PD-L1 antibody 2.5 mg/kg group, nine mice achieved PR (response rate 100%). In the chidamide 50 mg/kg plus celecoxib 50 mg/kg combined with anti-PD-L1 antibody 2.5 mg/kg group, eight mice were achieved PR (response rate 88%). Given the above, chidamide plus celecoxib regimen also possesses potent anti-tumor effect. When chidamide plus celecoxib was combined with anti-PD-1 or anti-PD-L1 antibody, the inhibition of tumor growth in CT26-bearing mice models was significantly increased (FIG. 8C). As shown in FIG. 8D, none of the mice in the treatment groups lost any body weight. As shown in FIG. 8E, chidamide combined with celecoxib group significantly increased the survival rate to about 55.5% in comparison with the anti-IgG group in the CT26-bearing tumor mice model. And the survival rate was better than that of anti-PD-1 (37.5%) or anti-PD-L1 (50%) group. The result proved that chidamide plus celecoxib regimen is a moderate combination against cancer. This regimen can control and regulate the tumor microenvironment and boost immunotherapy to some extent. Furthermore, chidamide plus metformin and celecoxib combined with the anti-PD-1 antibody was more potent to inhibit tumor growth and increased the survival rate to around 80%. A similar result was shown that chidamide plus celecoxib combined with the anti-PD-1 antibody group was potent to inhibit tumor growth and increased the survival rate to around 88%. Chidamide plus metformin and celecoxib combined with the anti-PD-L1 antibody group was more potent to inhibit tumor growth and increased the survival rate to around 100%. A similar result was shown that chidamide plus celecoxib combined with the anti-PD-L1 antibody group was potent to inhibit tumor growth and increased the survival rate to around 88%. After the treatment was stopped at day 26, the tumor in the CT26-bearing tumor mice grew faster in the IgG control group. However, chidamide plus celecoxib combined with or without metformin in the presence of an immune checkpoint inhibitor regimen was very potent in inhibiting tumor growth and thus significantly increased survival rate (FIG. 8E). From this study it was demonstrated that metformin may play a minor role to influence the tumor microenvironment and boost immunotherapy. This study also proved that chidamide plus celecoxib combined with immune checkpoint inhibitor was enough to boost anti-cancer immune response. On the other hand, the head to head comparison between anti-PD-1 and anti-PD-L1 antibody when combined with chidamide plus celecoxib has demonstrated that the anti-cancer activity of combination regimen with anti-PD-L1 antibody is better than that of combination regimen with anti-PD-1 antibody.

Figure 9A:
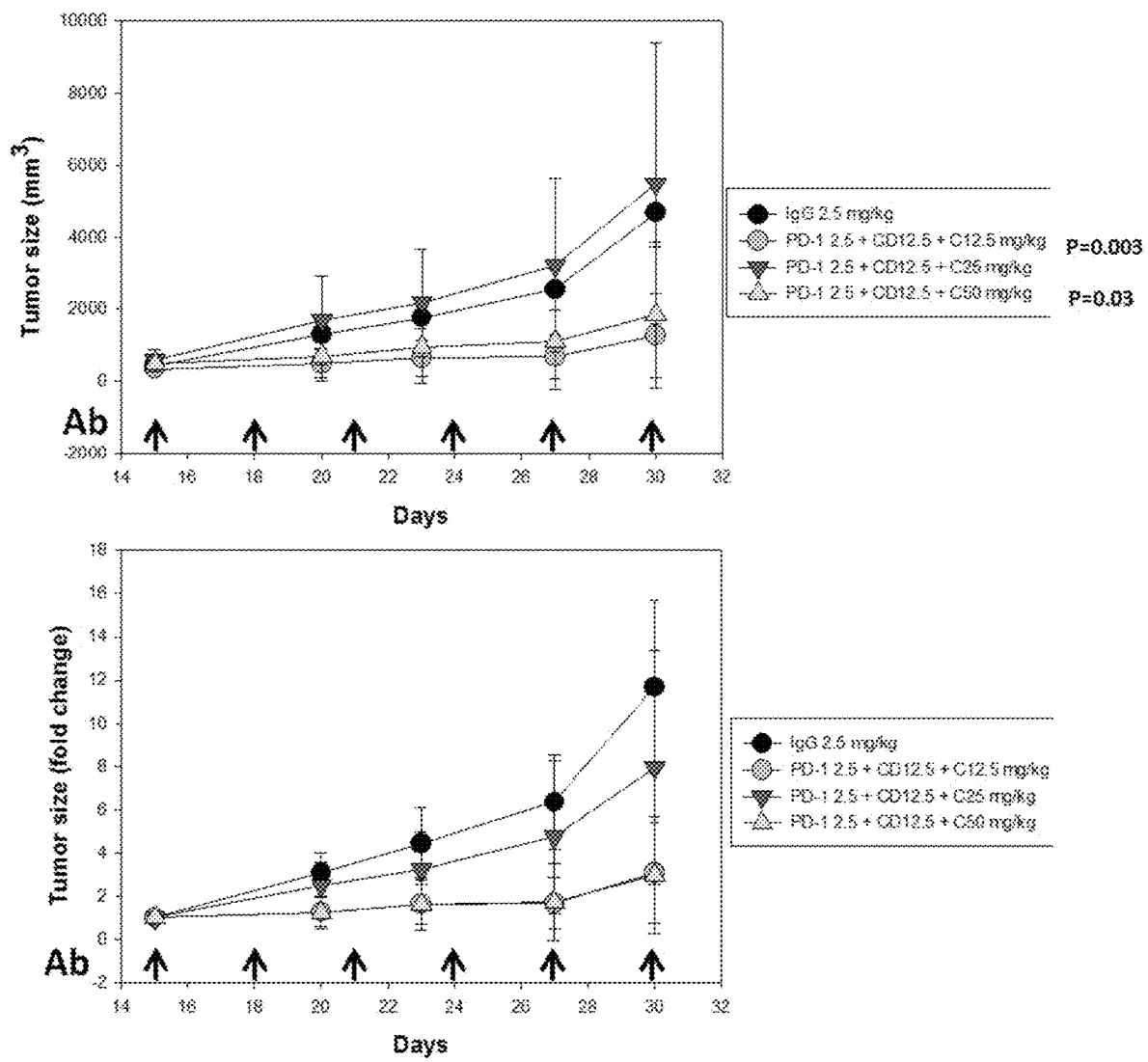
Figure 9B:
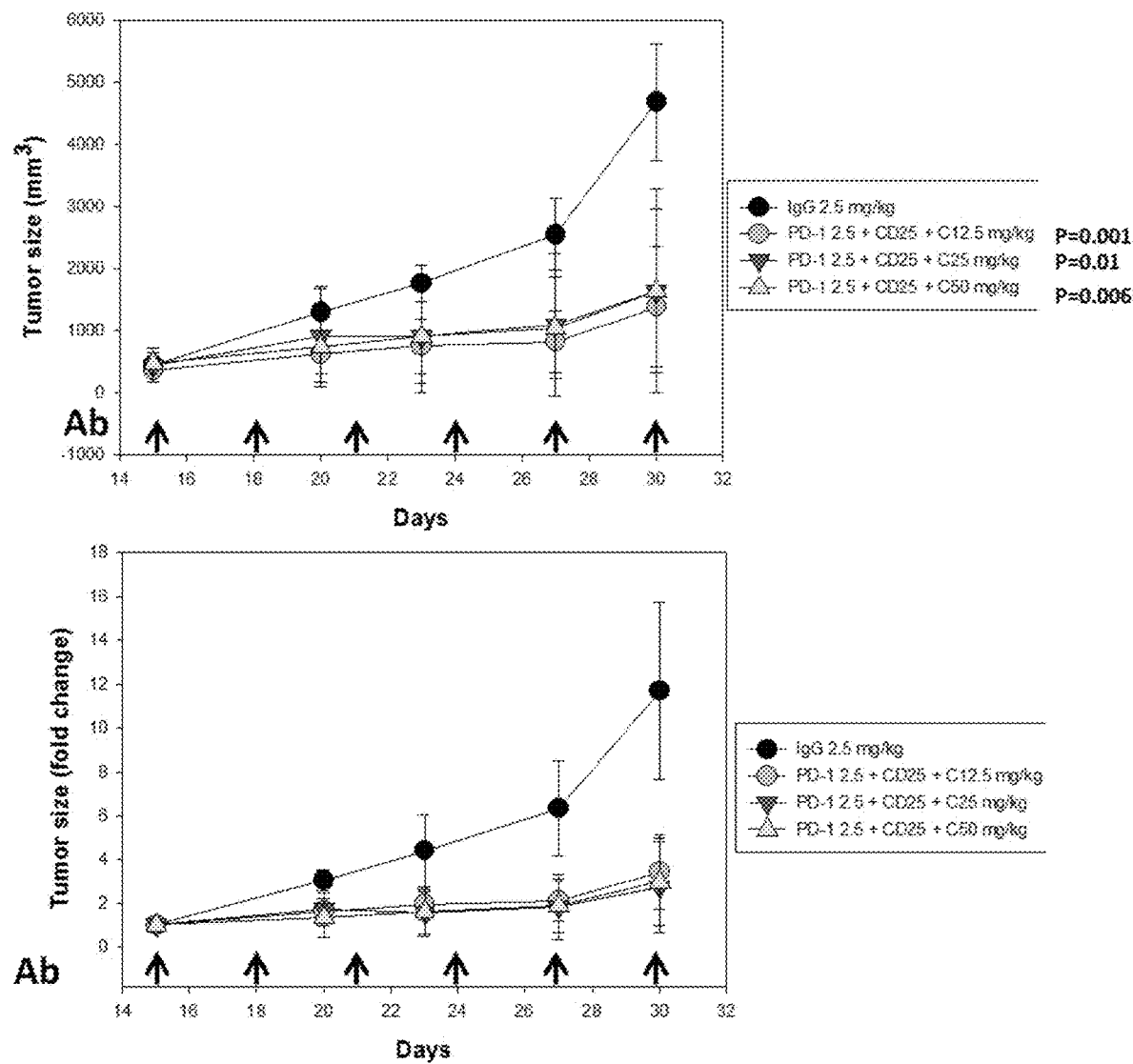
Figure 9C:
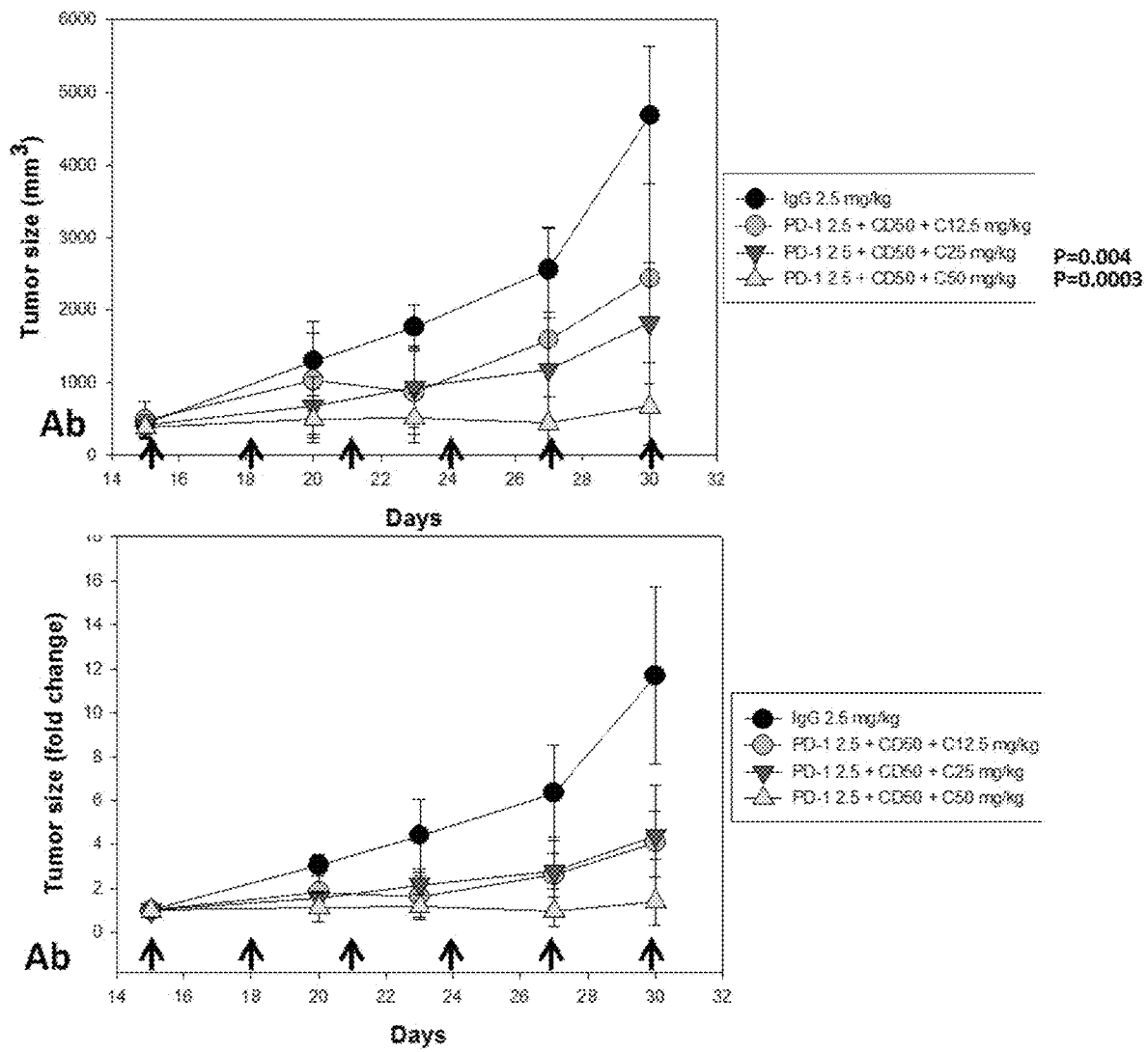
Figure 9D:
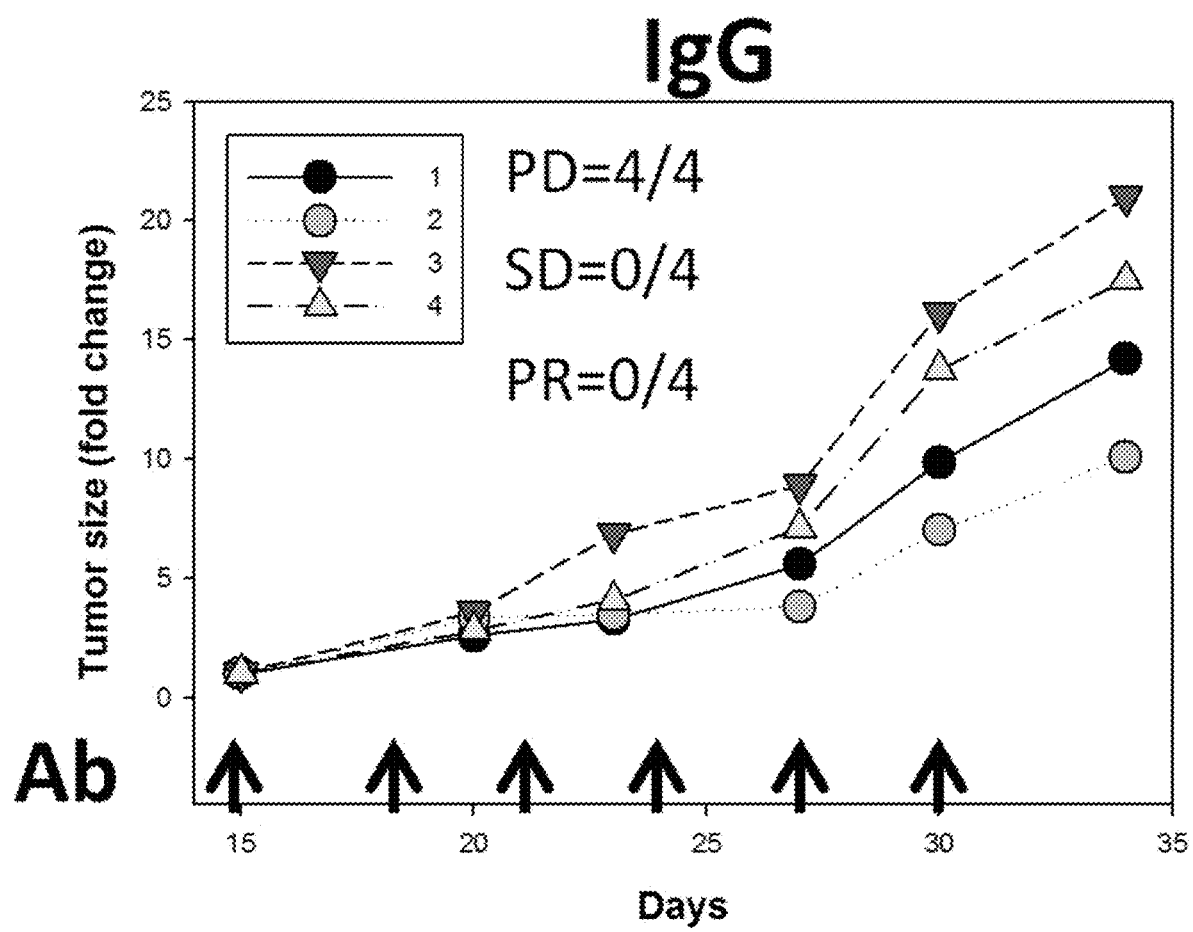
Figure 9D:
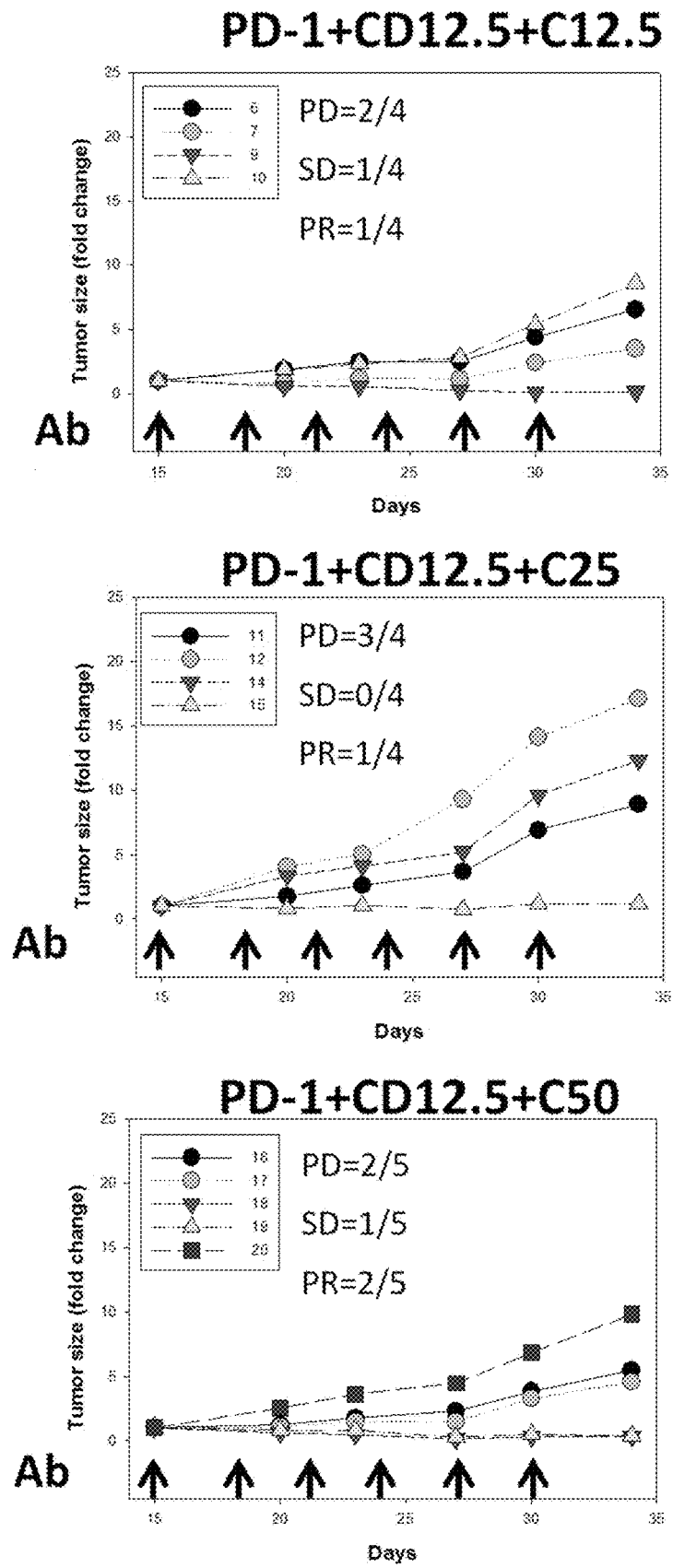
Figure 9D:
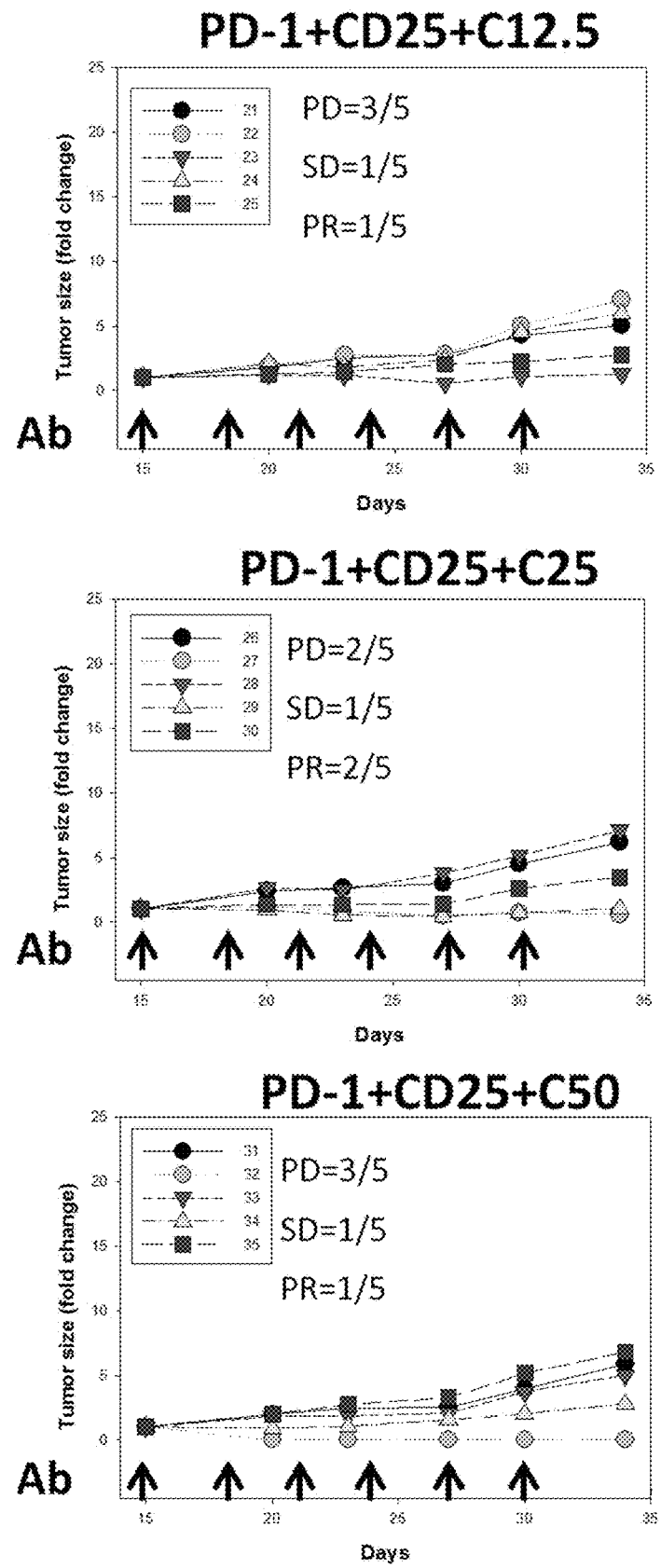
Figure 9D:
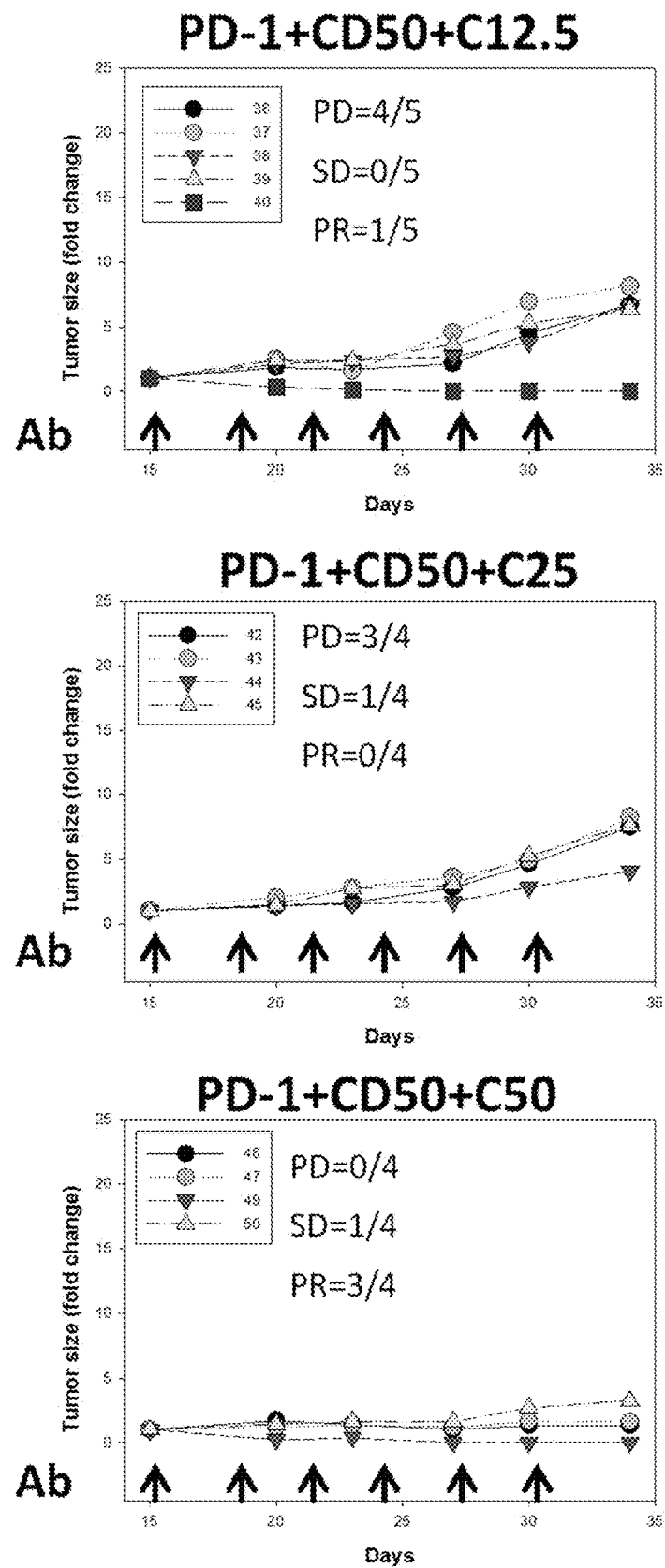
Figure 9E:
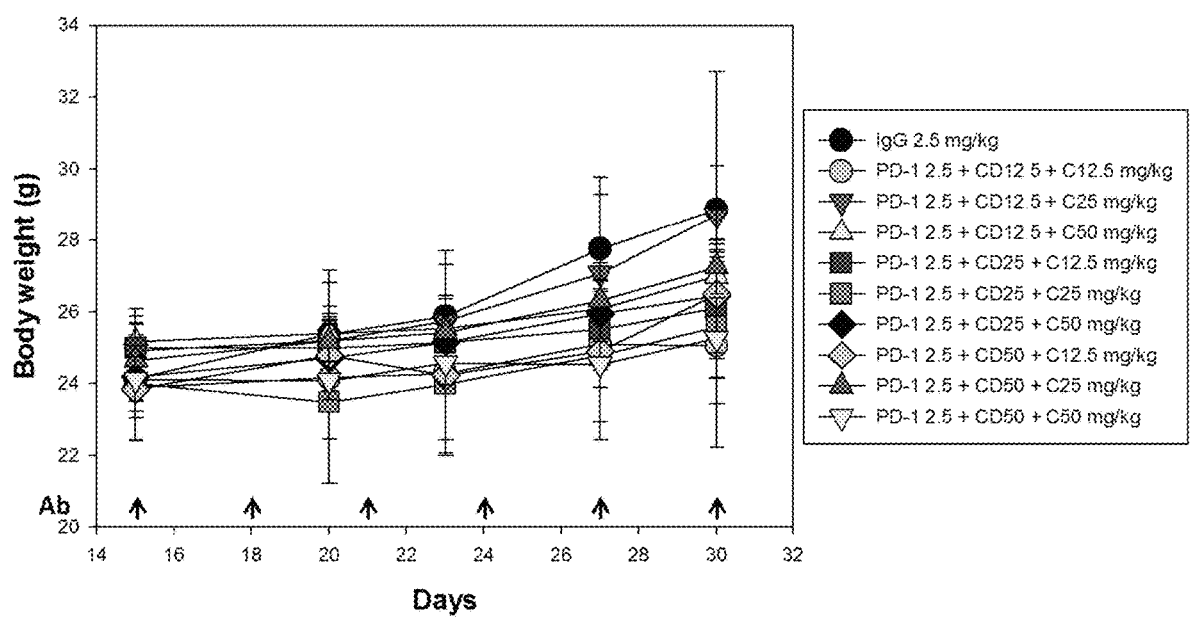
Figure 9F:
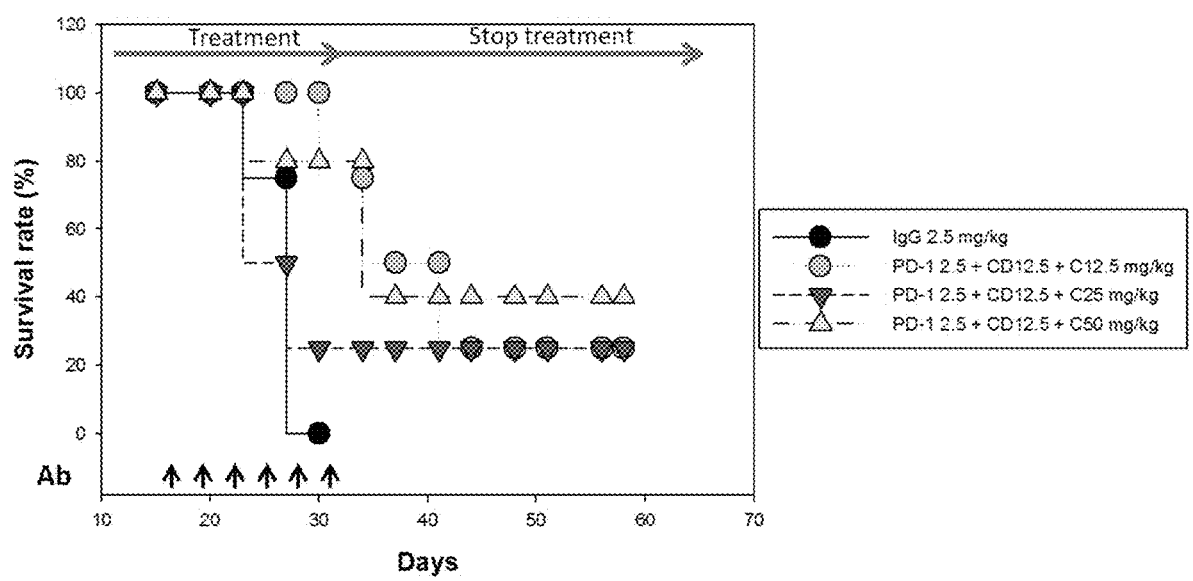
Figure 9G:
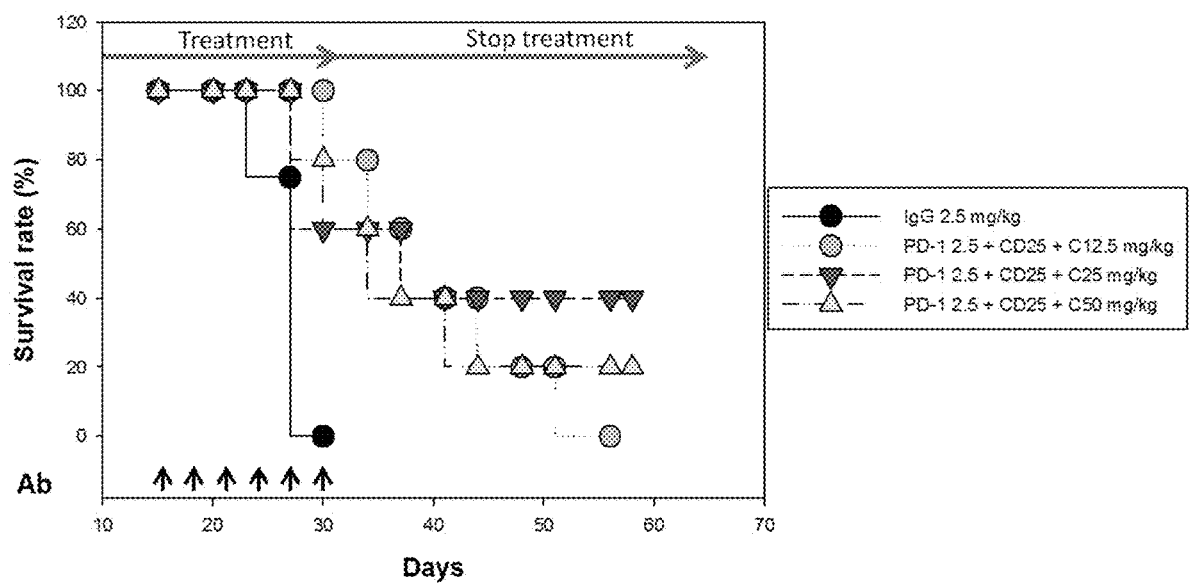
Figure 9H:
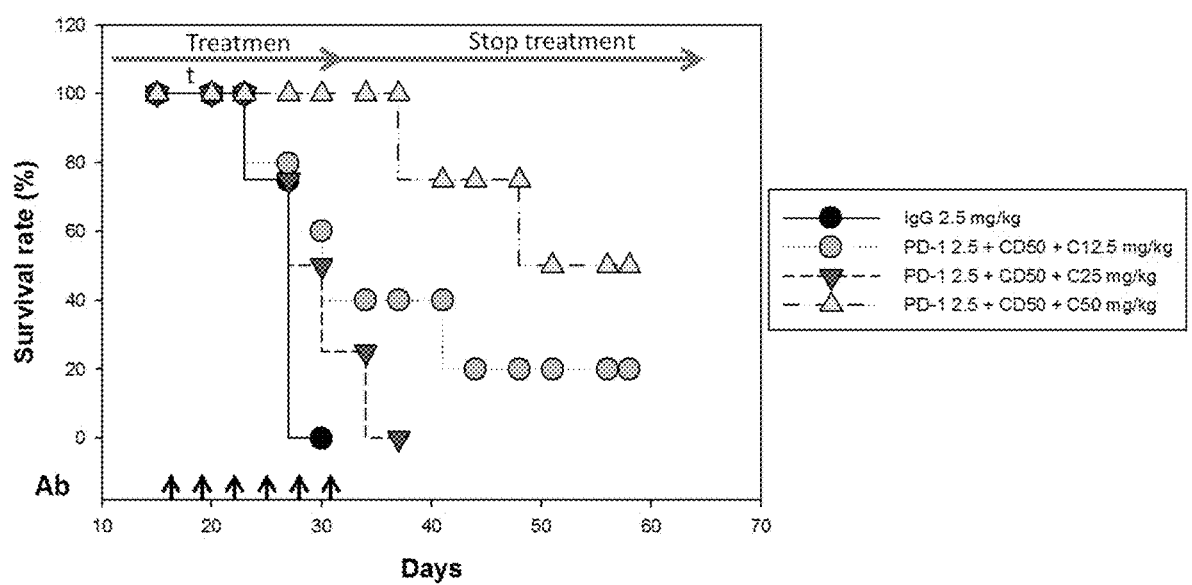

Example 9 to Confirm the Optimal Treatment Dose of Chidamide Plus Celecoxib Combined with Anti-PD-1 Antibody in CT26-Bearing Mice We were interested in evaluating which dosage ratio of chidamide and celecoxib combined with anti-PD-1 antibody is optimal for tumor inhibition in CT26-bearing mice. As shown in FIG. 9, the tumor size in the CT26-bearing mice grew to about 400-500 mm$^3$ at day 15. Combination of chidamide (12.5 mg/kg) plus celecoxib (12.5, 25, or 50 mg/kg) with anti-PD-1 antibody (2.5 mg/kg) significantly inhibited tumor growth in the CT26-bearing mice (FIG. 9A). Only the treatment groups with celecoxib at 25 mg/kg possessed weaker anti-cancer activity. Next, treatment groups with chidamide (25 mg/kg) plus celecoxib (12.5, 25, or 50 mg/kg) with anti-PD-1 antibody (2.5 mg/kg) showed significant inhibition of tumor growth in the CT26-bearing mice (FIG. 9B). Combination of chidamide (50 mg/kg) plus celecoxib (12.5, 25, or 50 mg/kg) with anti-PD-1 antibody (2.5 mg/kg) showed significant inhibition of tumor growth in the CT26-bearing mice (FIG. 9C). The data has proved again that chidamide 50 mg/kg plus celecoxib50 mg/kg combined with the anti-PD-1 antibody is even more effective in inhibiting tumor growth in the CT26-bearing mice (FIG. 9C). These results suggested that chidamide 50 mg/kg plus celecoxib 50 mg/kg combined with immune checkpoint inhibitor anti-PD-1 antibody performed strong anti-tumor ability in CT26-bearing mice model. On the other hand, these results also demonstrated that chidamide/celecoxib dosage ratio was important. The anti-cancer effects of various therapeutic modalities in all of the mice are shown in FIG. 9D. The treatment with chidamide 12.5 mg/kg plus various doses of celecoxib (12.5, 25, or 50 mg/kg) combined with anti-PD-1 antibody only showed slight anti-cancer activity and only one or two mice achieved PR (response rate 25-40%). The treatment with chidamide 25 mg/kg plus various doses of celecoxib (12.5, 25, or 50 mg/kg) combined with anti-PD-1 antibody only showed slight anti-cancer activity and only one or two mice achieved PR (response rate 20-40%). The treatment with chidamide 50 mg/kg plus celecoxib 50 mg/kg combined with anti-PD-1 antibody showed potent antitumor activities and three mice achieved PR (response rate 75%). As shown in FIG. 9E, none of the mice in the treatment groups lost any body weight. As shown in FIG. 9F, lower chidamide dosage (12.5 mg/kg) plus celecoxib at dosage of 50 mg/kg combined with anti-PD-1 antibody increased the survival rate to about 40% in comparison with the anti-IgG antibody control group in the CT26-bearing tumor mice model. The result demonstrated that chidamide 12.5 mg/kg plus high dosage of celecoxib (50 mg/kg) regimen had better anti-cancer effect. Furthermore, as shown in FIG. 9G, intermediate dosage of chidamide (25 mg/kg) plus celecoxib at dosage from 12.5 to 50 mg/kg combined with anti-PD-1 antibody had no improvement in the survival rate. Finally, as shown in FIG. 9H, high dosage of chidamide (50 mg/kg) plus high dosage of celecoxib (50 mg/kg) combined with anti-PD-1 antibody showed potent inhibition of tumor growth and increased the survival rate to around 50% at day 58. After the treatment was stopped at days 30, the tumor in the CT26-bearing tumor mice grew faster in the IgG control group. In this study, the treatment was started when the tumor size reached about 400-500 mm$^3$. This would result in lower response rate and survival rate in all treatment groups. However, chidamide 50 mg/kg plus celecoxib 50 mg/kg combined with anti-PD-1 Ab regimen still was very potent in inhibiting tumor growth and thus significantly increased survival rate (FIGS. 9F-H).

Figure 10A:
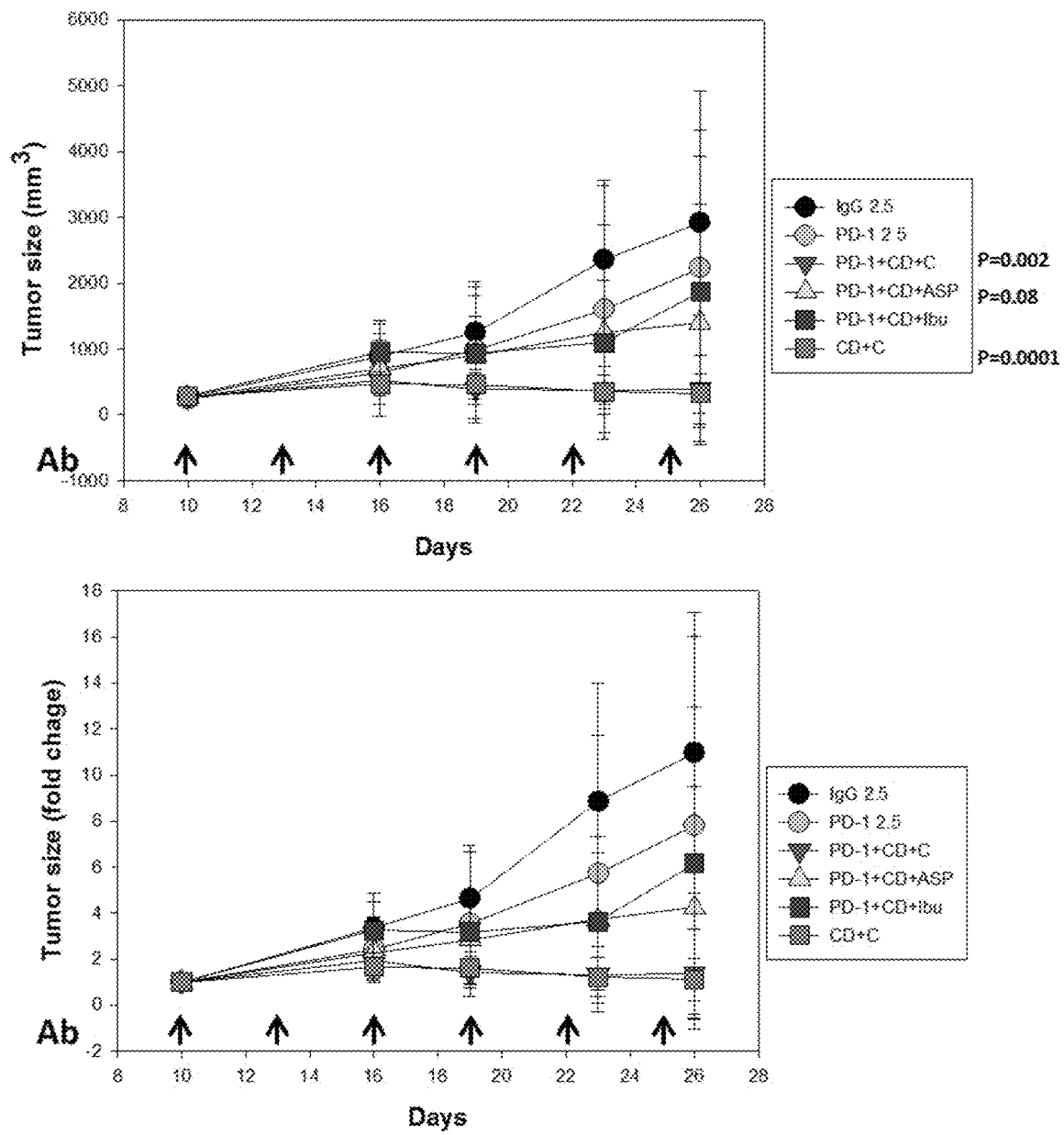
Figure 10B:
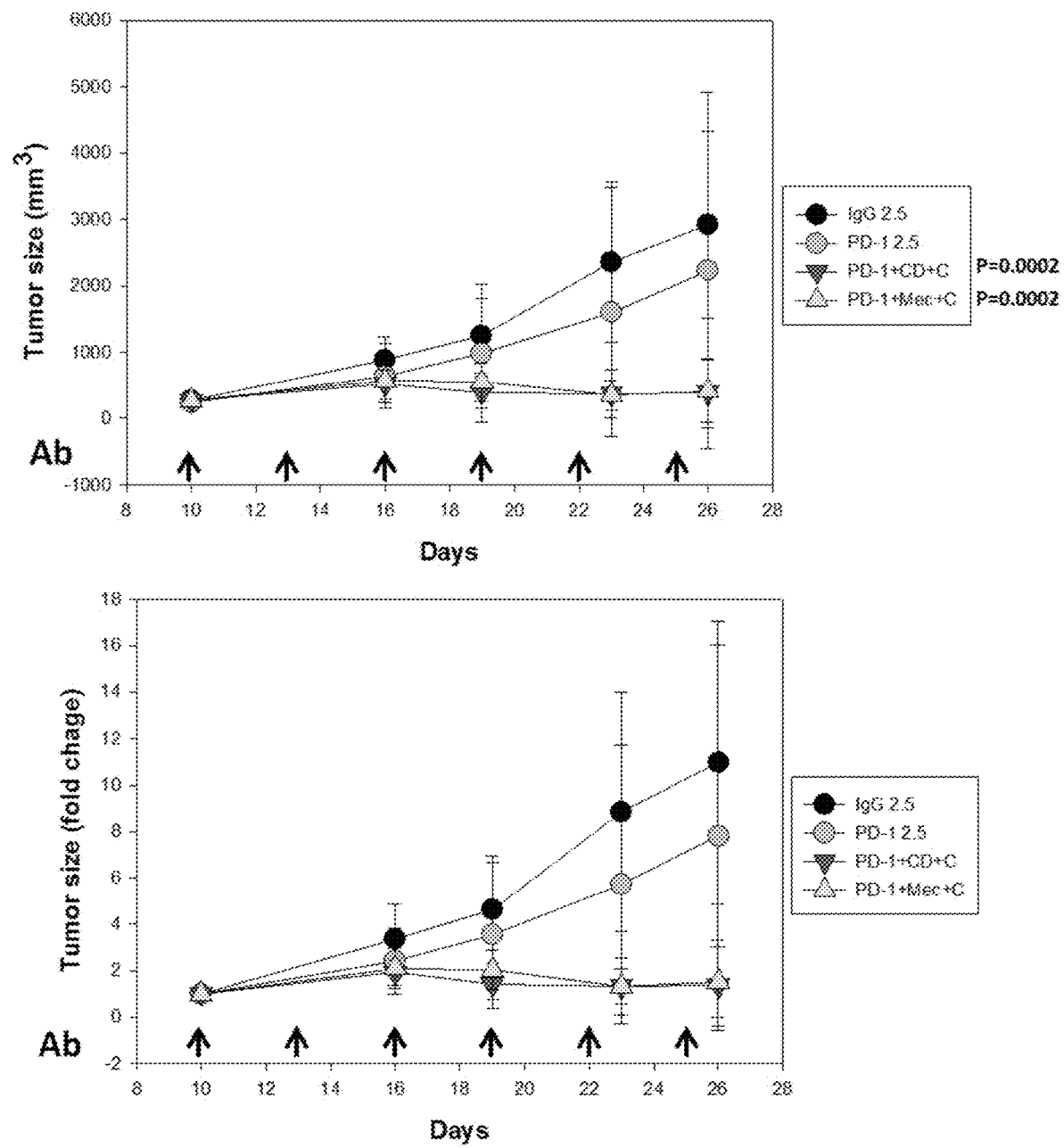
Figure 10C:
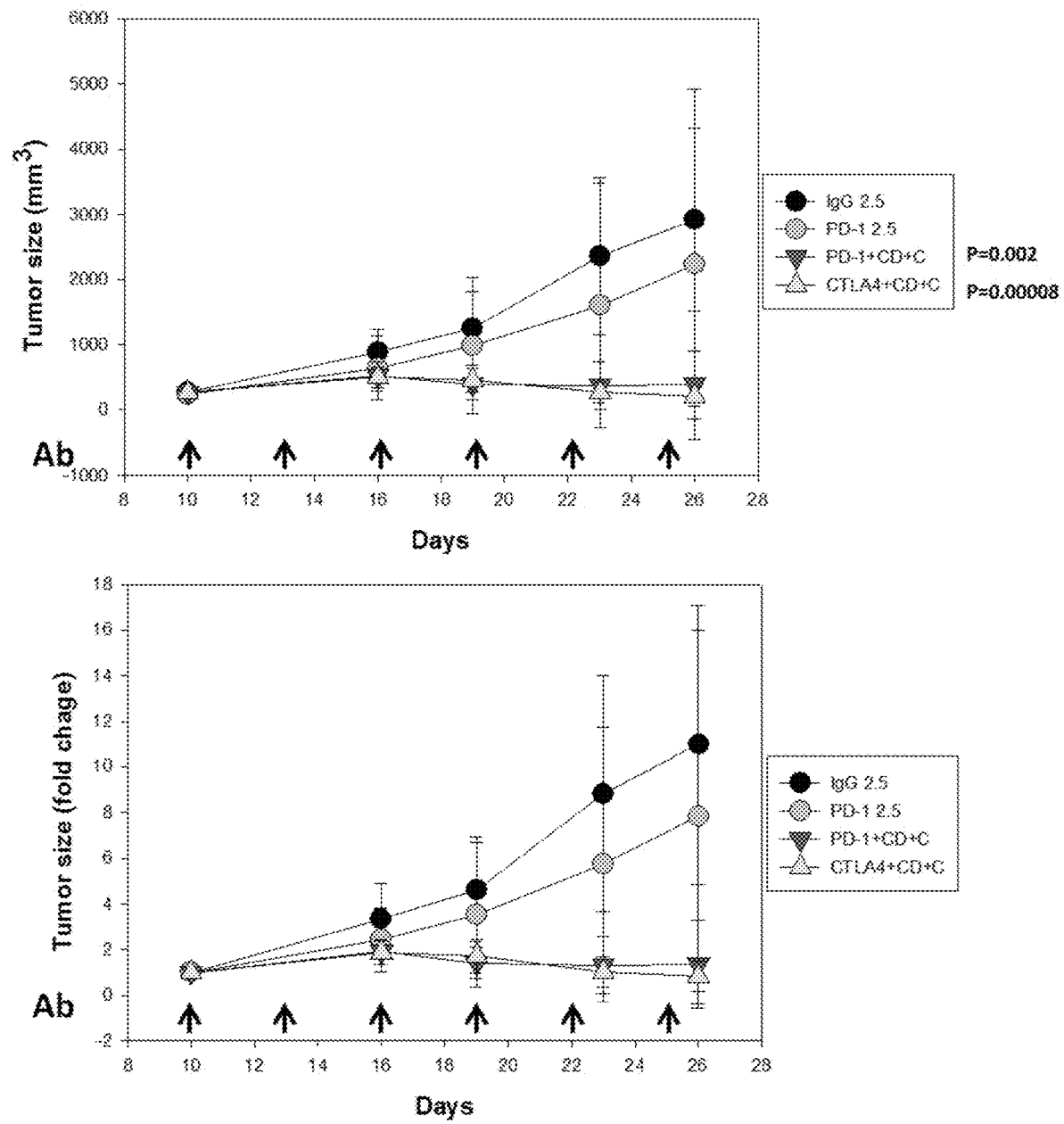
Figure 10D:
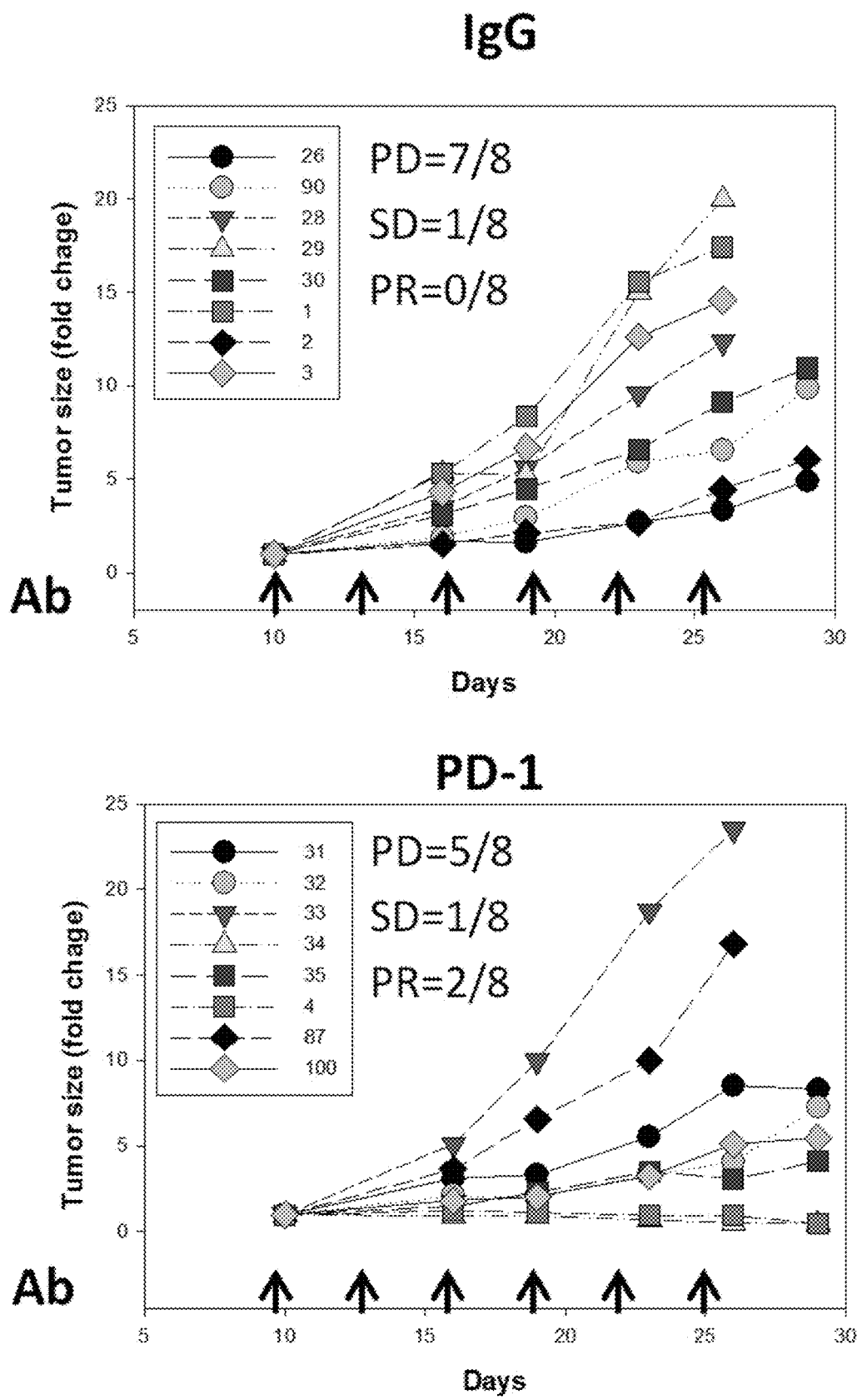
Figure 10D:
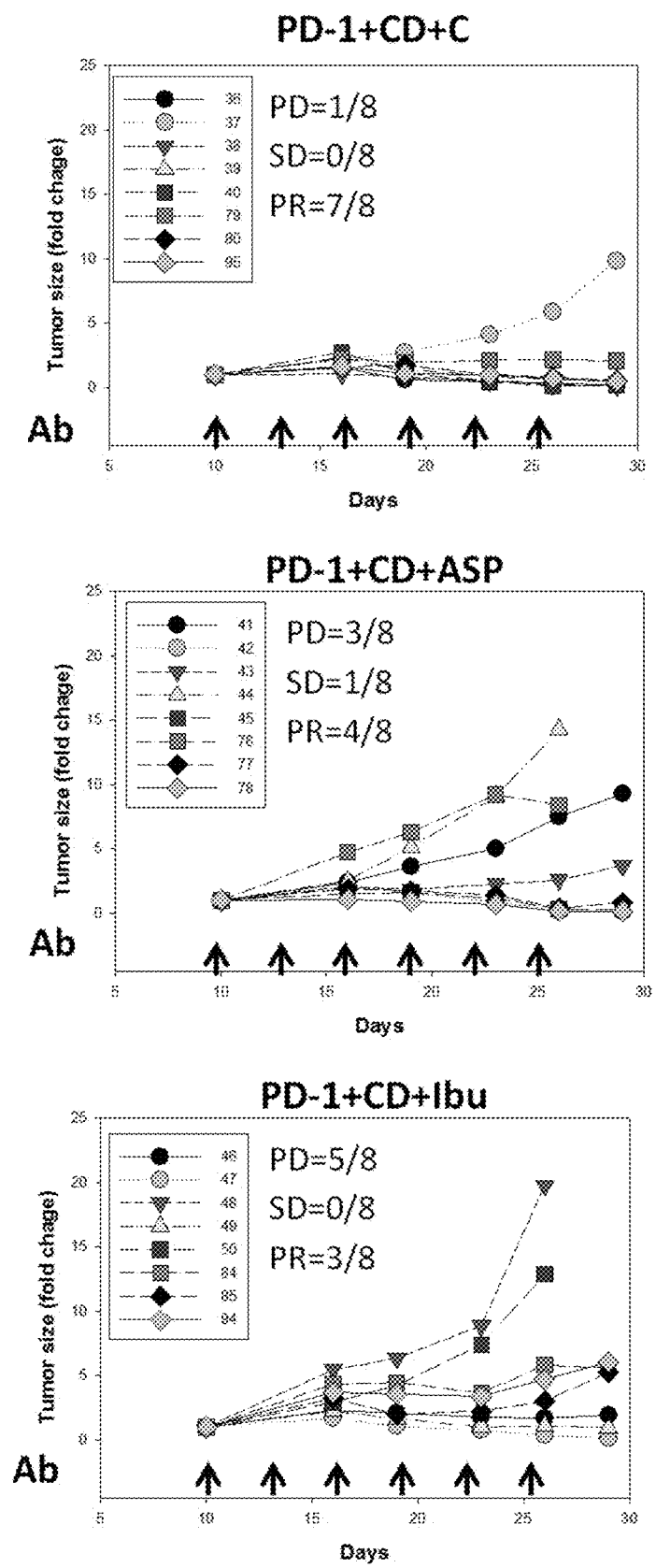
Figure 10D:
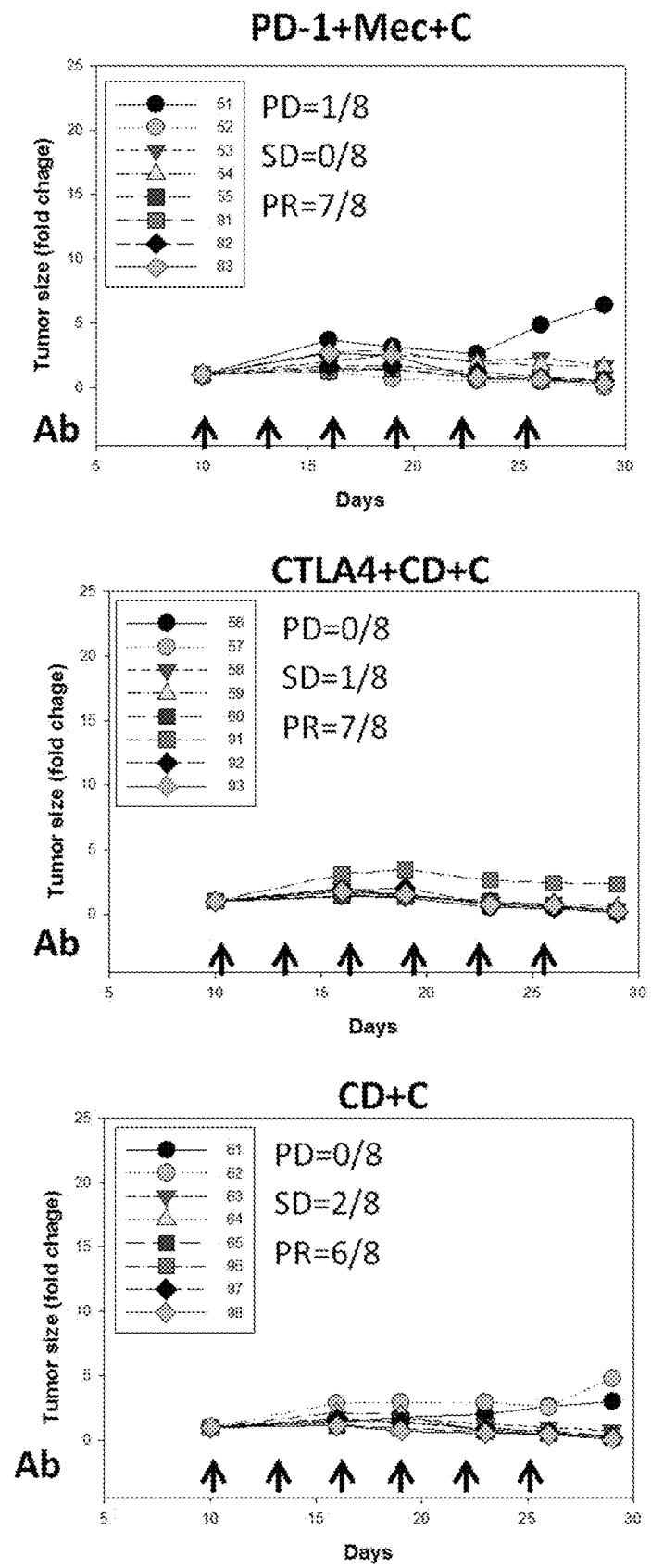
Figure 10E:
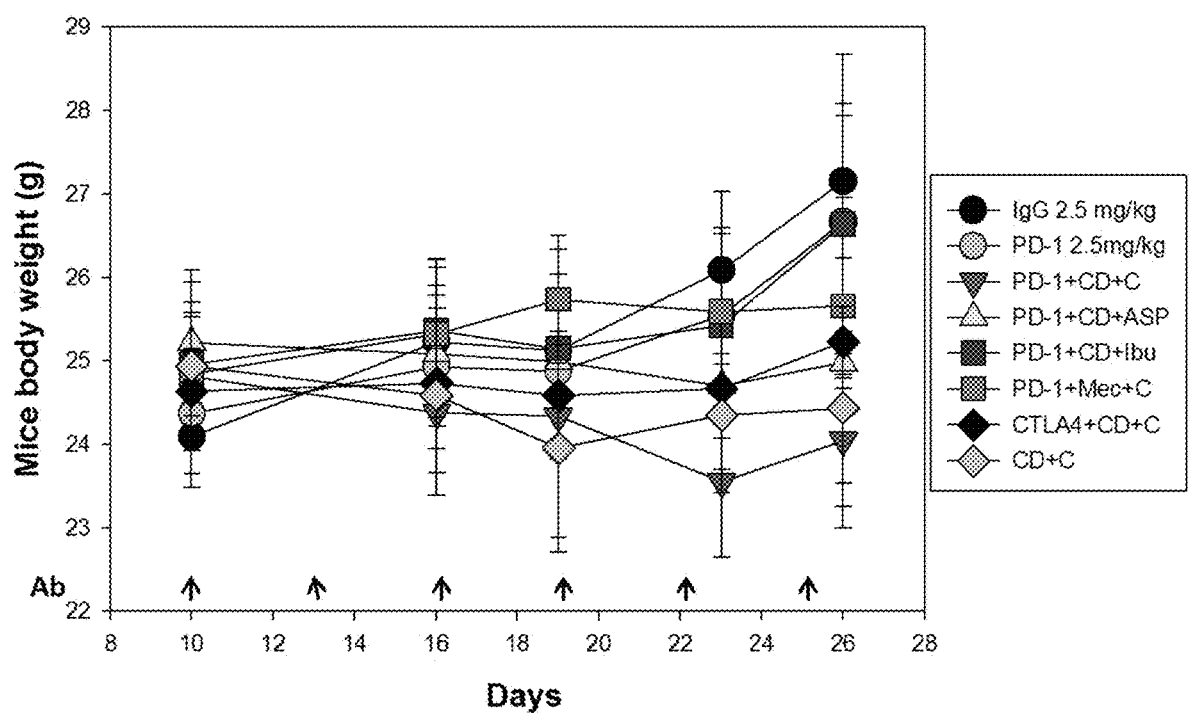
Figure 10F:
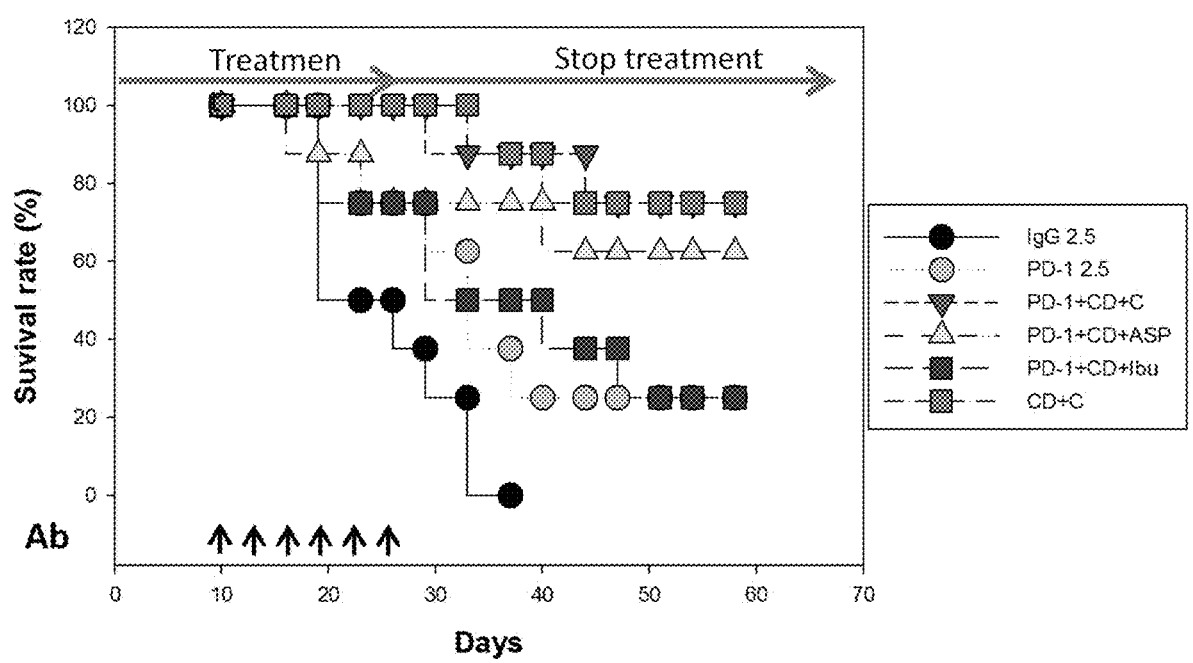
Figure 10G:
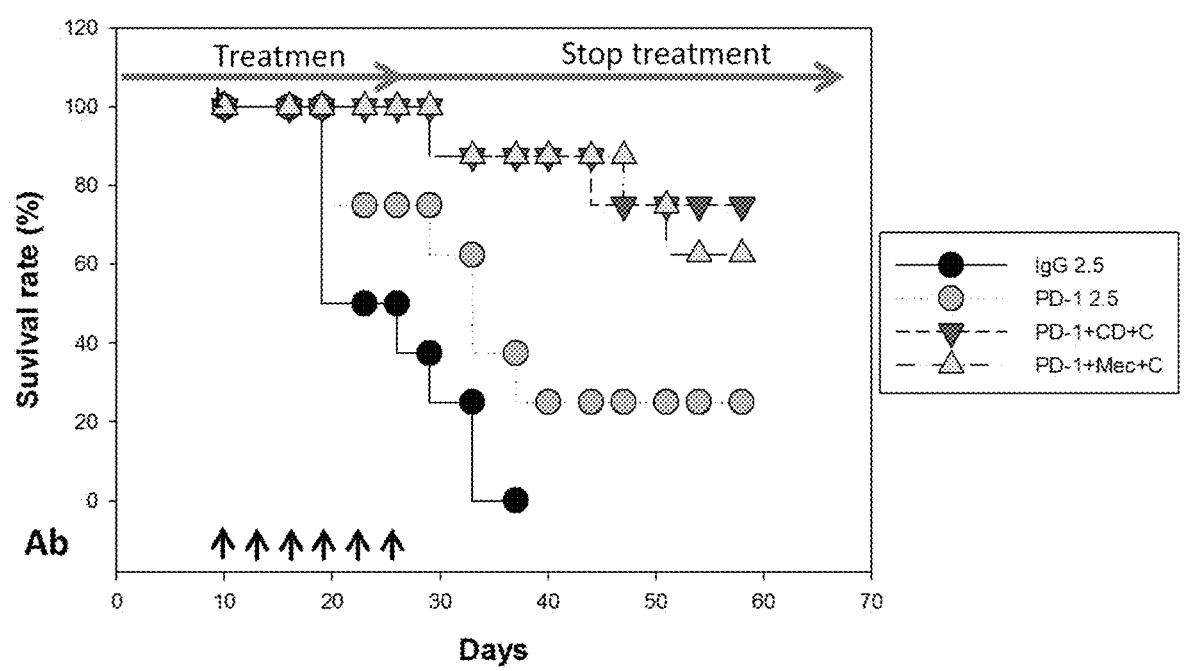
Figure 10H:
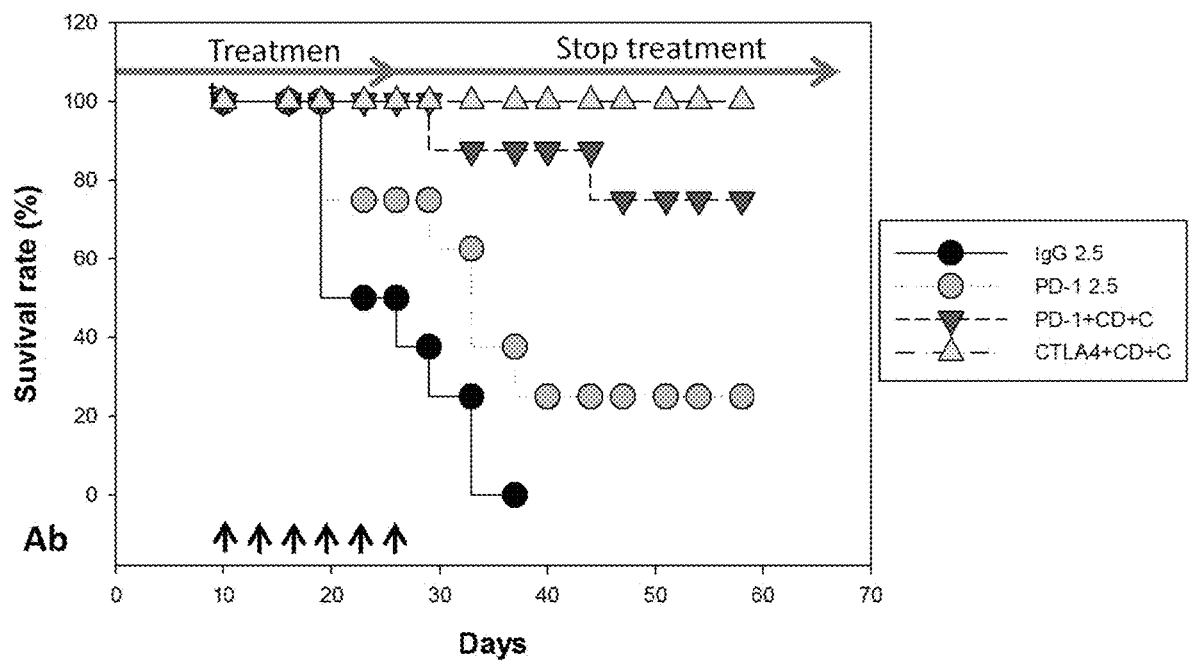

Example 10 to Clarify the Anti-Cancer Mechanisms of HDAC Inhibitors Plus COX-2 Inhibitors Combined with Anti-PD-1 or Anti-CTLA-4 Antibody in CT26-Bearing Mice Next, we were interested in evaluating whether other HDAC inhibitors and COX-2 inhibitors, in the presence of an immune checkpoint inhibitor antibody, would still perform tumor inhibition in CT26-bearing mice. As shown in FIG. 10, the tumor size in the CT26-bearing mice grew to about 250-300 mm$^3$ at day 10. First, the different COX-2 inhibitors plus chidamide combined with anti-PD-1 Ab in the CT26-bearing mice were performed. Combination of chidamide plus celecoxib (selective COX-2 inhibitor, 50 mg/kg), aspirin (non-selective COX-2 inhibitor, 50 mg/kg), or ibuprofen (non-selective COX-2 inhibitor, 50 mg/kg), in the presence of an anti-PD-1 antibody, showed significant inhibition of tumor growth in the CT26-bearing mice (FIG. 10A). However, chidamide 50 mg/kg plus celecoxib 50 mg/kg combined with or without the anti-PD-1 Ab 2.5 mg/kg is even more effective in inhibiting tumor growth in the CT26-bearing mice as compared to other groups (FIG. 10A). Surprisingly, chidamide 50 mg/kg combined with celecoxib 50 mg/kg group very significantly inhibited tumor growth as shown in FIG. 10A. According to the COX-2 inhibitors at the same dosage, the anti-cancer activity (from more to less) was as follows: celecoxib >aspirin >ibuprofen. Next, we evaluated different HDAC inhibitors such as chidamide, entinostat, and mocetinostat, in combination with celecoxib and anti-PD-1 antibody. Entinostat plus celecoxib combined with anti-PD-1 antibody regimen has been shown to have potent anti-cancer activity as shown in FIG. 3B. In this study, we evaluated mocetinostat (class I HDAC inhibitor, 30 mg/kg) plus celecoxib 50 mg/kg combined with anti-PD-1 antibody 2.5 mg/kg for its potency of anti-cancer activity. There was no significant difference between chidamide plus celecoxib and mocetinostat plus celecoxib, in combination with anti-PD-1 antibody (FIG. 10B). Furthermore, we also clarified that combination with immune checkpoint inhibitor anti-CTLA-4 antibody performed tumor inhibition in CT26-bearing mice. The results showed chidamide plus celecoxib combined with anti-PD-1 or anti-CTLA-4 antibody significantly inhibited tumor growth in the CT26-bearing mice (FIG. 10C). There was no significant difference between treatment with anti-PD-1 and anti-CTLA-4 antibody, in combination with chidamide and celecoxib. These results suggested that HDAC inhibitors plus COX-2 inhibitors combined with immune checkpoint inhibitors performed strong anti-tumor ability in CT26-bearing mice model. The therapeutic responses of all the mice treated with various therapeutic modalities were shown in FIG. 10D. The group treated with anti-PD-1 antibody (2.5 mg/kg) only had slight anti-cancer activity and only two mice achieved PR (response rate 25%). Treatment with chidamide 50 mg/kg plus celecoxib 50 mg/kg regimen showed potent tumor growth inhibition and six mice achieved PR (response rate 75%); however, it was less potent than chidamide plus celecoxib combined with anti-PD-1 antibody regimen, where seven mice achieved PR (response rate 88%). On the other hand, we evaluated the combination with aspirin 50 mg/kg and ibuprofen 50 mg/kg for their potency of anti-cancer activity. Treatment with chidamide plus aspirin or ibuprofen combined with anti-PD-1 antibody showed less anti-cancer activity in comparison with that of celecoxib-containing treatment and only four and three mice achieved PR (response rate 50%, 38%, respectively). It seems clear that celecoxib was more potent to inhibit tumor growth than aspirin and ibuprofen. Next, the comparison of chidamide and mocetinostat in the anti-cancer activity was determined. In the group treated with mocetinostat 30 mg/kg or chidamide 50 mg/kg plus celecoxib 50 mg/kg combined with anti-PD-1 antibody 2.5 mg/kg, seven mice achieved PR (response rate 88%). This result demonstrated that chidamide, entinostat, and mocetinostat possessed similar anti-cancer activity. These compounds were classified as class I HDAC inhibitor. Next, we were interested in whether anti-CTLA-4 antibody possessed similar activity like other immune checkpoint inhibitors such as anti-PD-1 or anti-PD-L1 antibody. In the group treated with chidamide 50 mg/kg plus celecoxib 50 mg/kg combined with anti-CTLA-4 2.5 mg/kg or anti-PD-1 antibody 2.5 mg/kg, seven mice achieved PR (response rate 88%). Given the above, HDAC inhibitors (chidamide, entinostat, mocetinostat) plus celecoxib regimen possesses potent antitumor growth activity. And further combined with anti-PD-1 or anti-CTLA-4 antibody, the inhibition of tumor growth in CT26-bearing mice models was increased (FIG. 10D). As shown in FIG. 10E, none of the mice in the treatment groups lost any body weight. As shown in FIG. 10F, chidamide plus celecoxib combined with or without anti-PD-1 antibody possessed potent anti-cancer activity and significantly increased the survival rate to about 75% in comparison with the anti-PD-1 antibody control group (about 20%) in the CT26-bearing tumor mice model. The result proved that HDAC inhibitors plus COX-2 inhibitors regimen, especially in combination with immune checkpoint inhibitors, is a good combination against cancer. The regimen can control tumor microenvironment and boost immunotherapy. This result also demonstrated that regimens containing aspirin or ibuprofen possessed anti-cancer activity and increased the survival rate but showed weaker activity than regimen containing celecoxib as shown in FIG. 10F. Furthermore, as shown in FIG. 10G, chidamide plus celecoxib combined with the anti-PD-1 antibody was more potent than regimen containing mocetinostat for tumor growth inhibition and increased the survival rate (75% vs 62.5%). Finally, as shown in FIG. 10H, chidamide plus celecoxib combined with the anti-CTLA-4 antibody was more potent to inhibit tumor growth and increased the survival rate to around 100%. This result demonstrated that combination regimen with anti-CTLA-4 antibody was more powerful than that with anti-PD-1 antibody (survival rate 75%) to increase the survival rate in the CT26-bearing tumor mice model. After the treatment was stopped at days 26, the tumor in the CT26-bearing tumor mice grew faster in the IgG control group. However, the potent inhibition of tumor growth and increased survival rate can be achieved by combination regimens as follows: chidamide plus aspirin, ibuprofen or celecoxib, or further combined with an immune checkpoint inhibitor; mocetinostat plus celecoxib combined with immune checkpoint inhibitor regimen; anti-CTLA-4 antibody combined with chidamide plus celecoxib (FIG. 10F-H). Taken together, immune checkpoint inhibitors including anti-PD-1, anti-PD-L1, and anti-CTLA-4 antibody, in combination with chidamide plus celecoxib regimens, can efficiently influence the number or activity of major components in the tumor microenvironment such as Treg (regulatory T cells), MDSCs (myeloid-derived suppressor cells), TAM (tumor-associated macrophage), NK (natural killer T cells), and CTL (cytotoxic T-lymphocytes). Finally, these regimens were efficient to boost immunotherapy. These results further proved our proposal that an HDAC inhibitor (especially class I HDAC inhibitor) plus COX-2 inhibitors (especially selective COX-2 inhibitors) efficiently boosts anti-cancer activity of immune checkpoint inhibitors in response rate and survival rate.

Figure 11A:
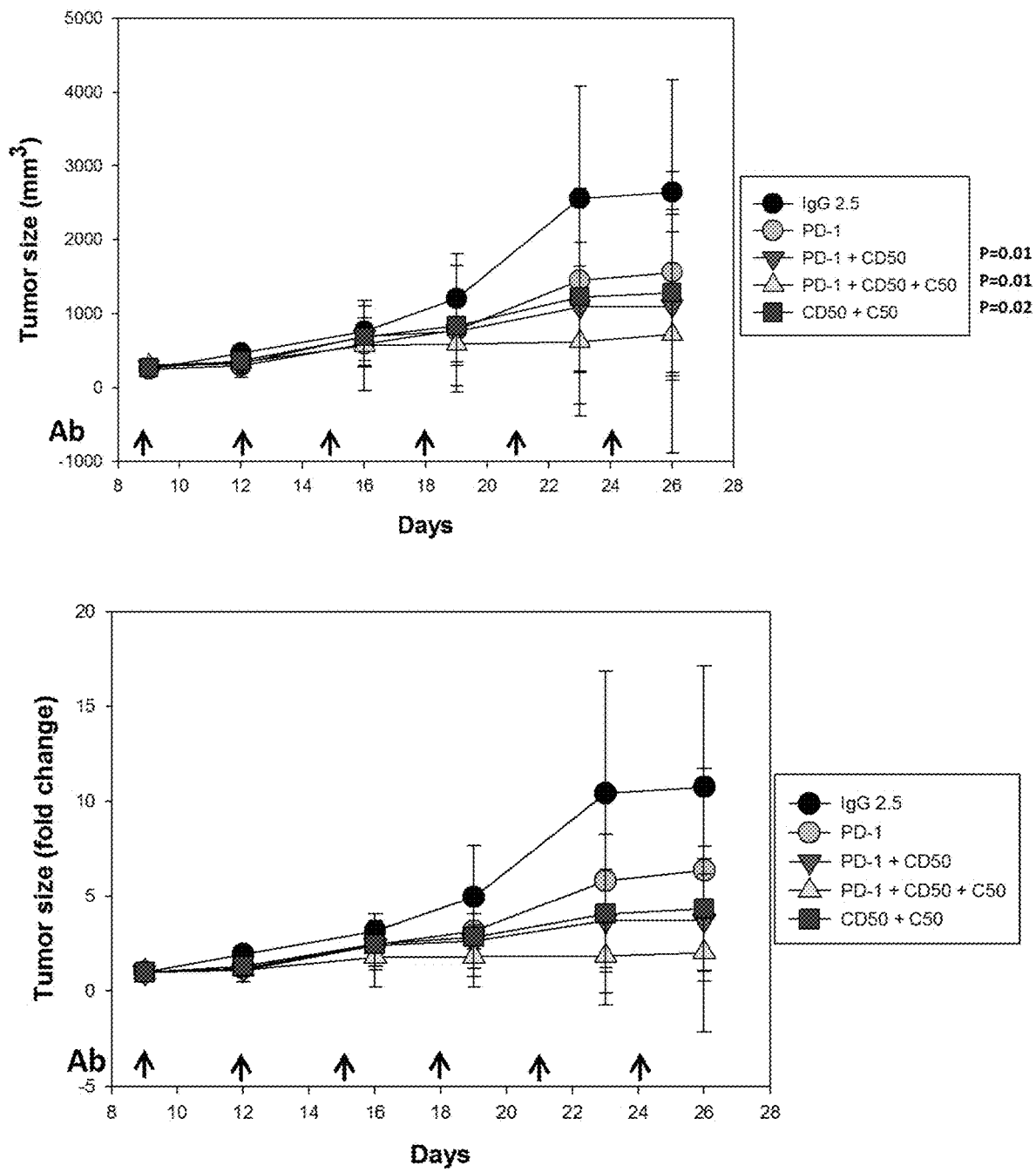
Figure 11B:
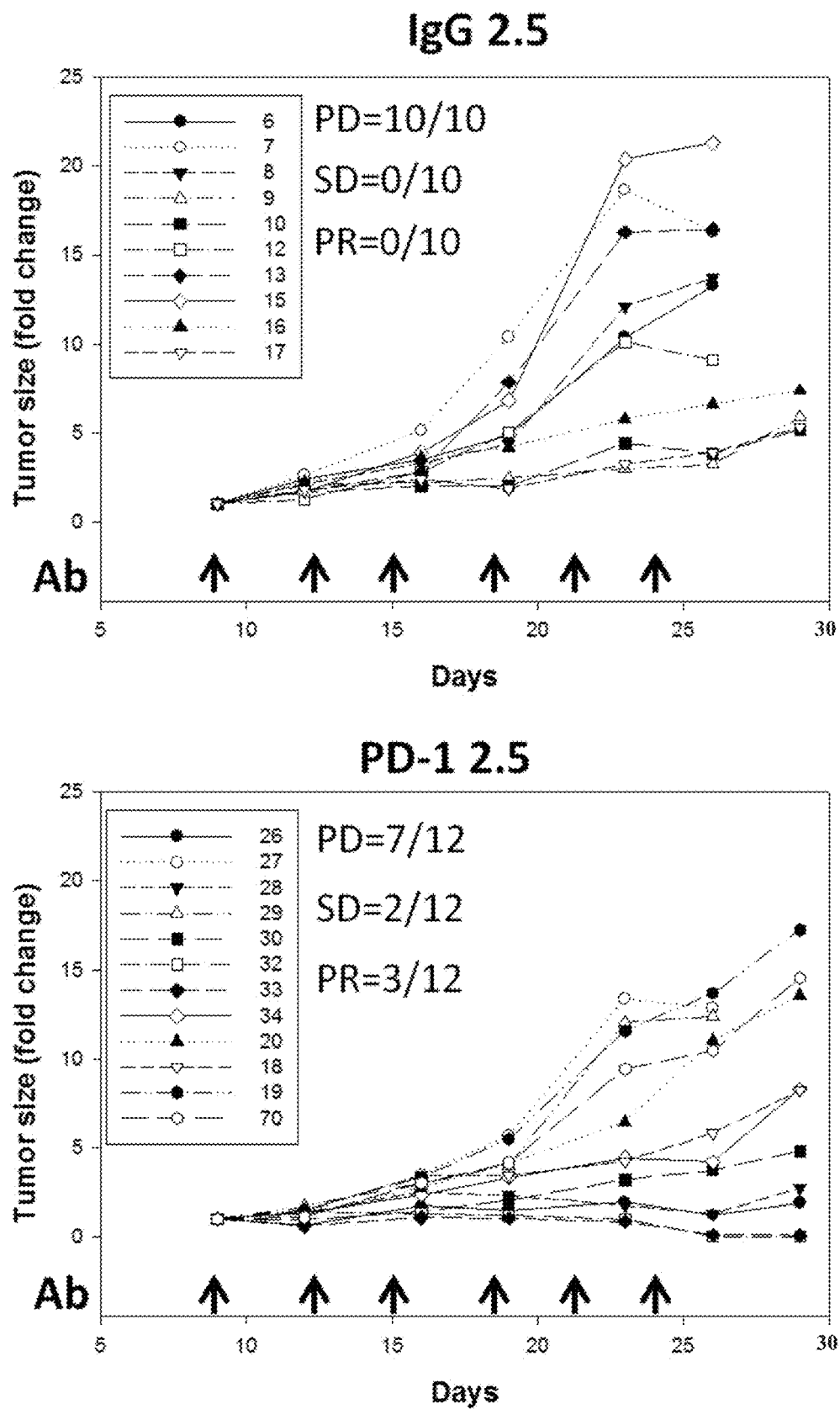
Figure 11B:
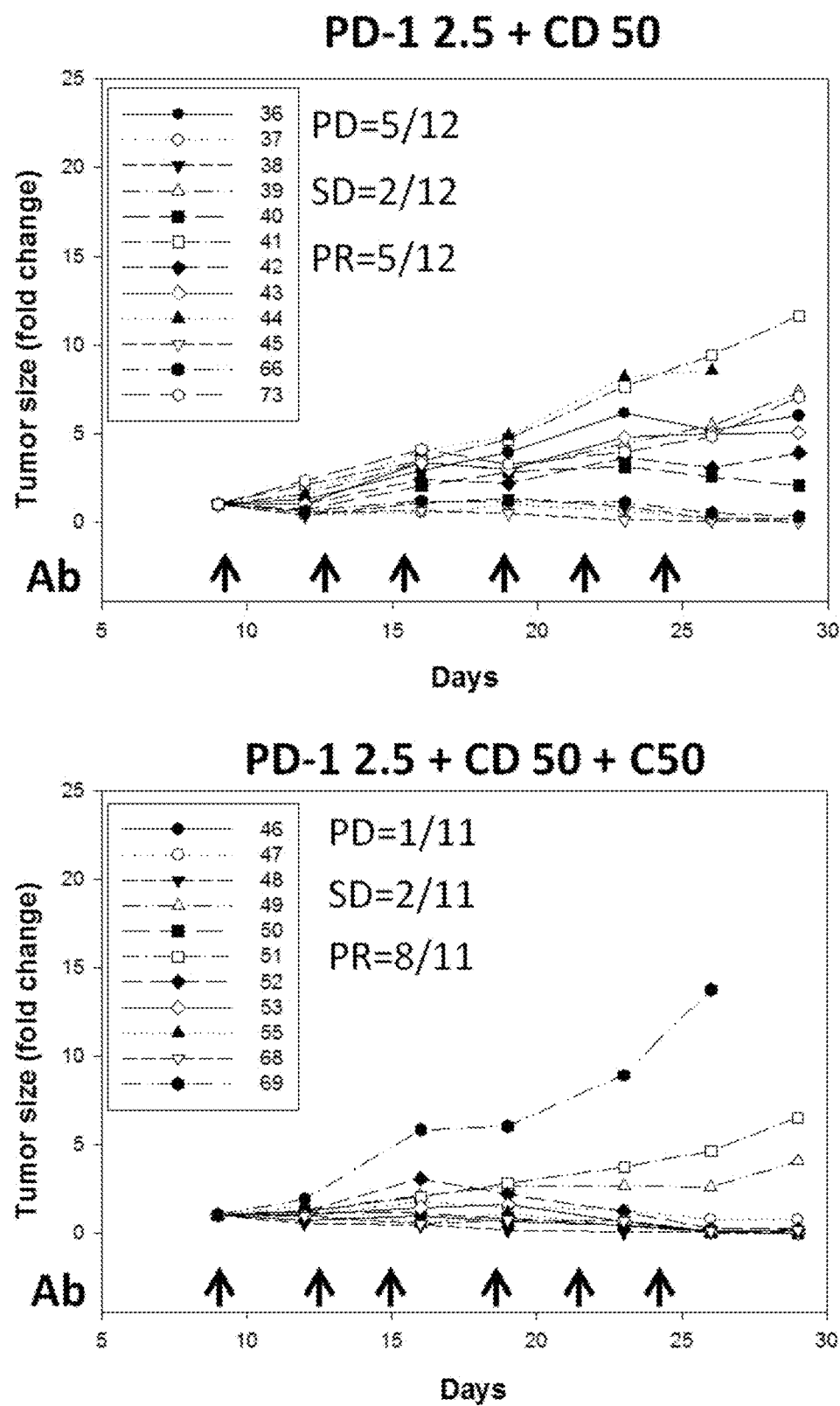
Figure 11B:
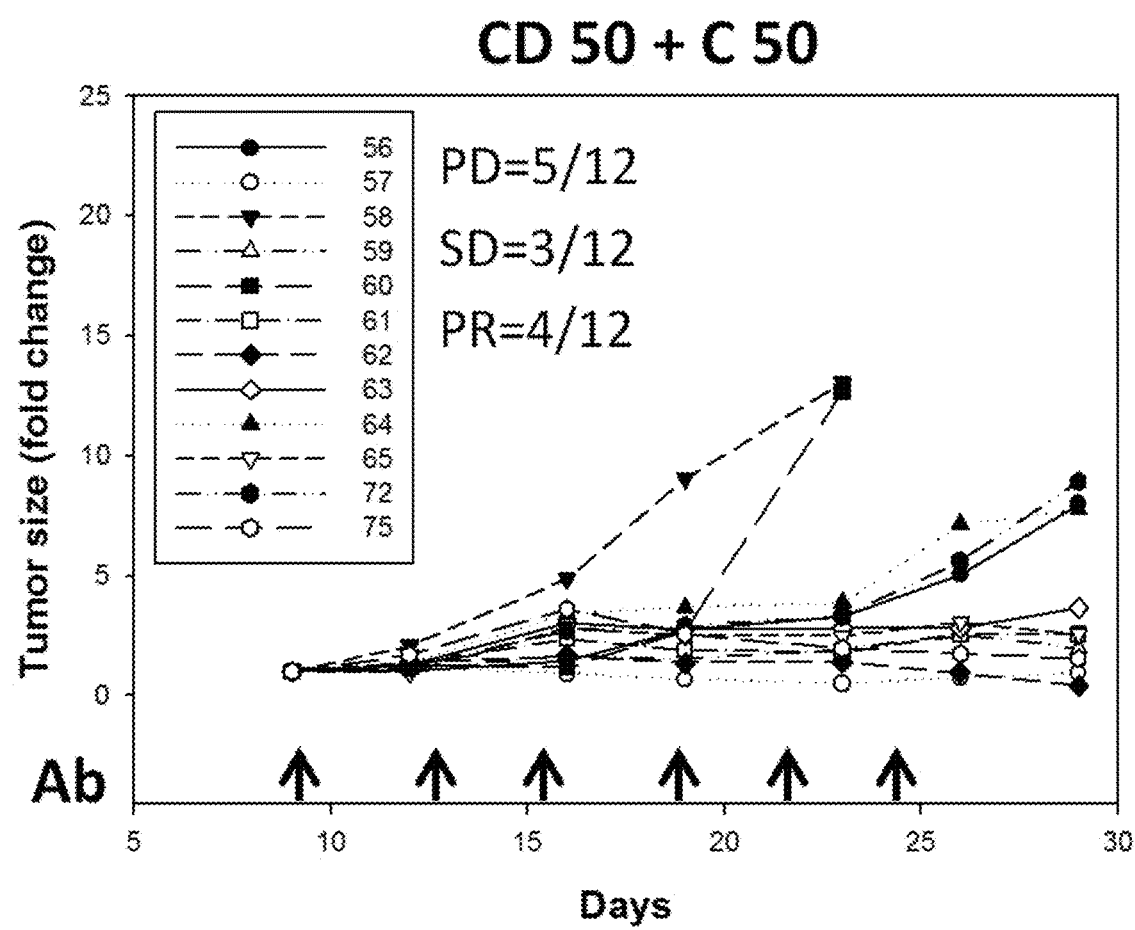
Figure 11C:
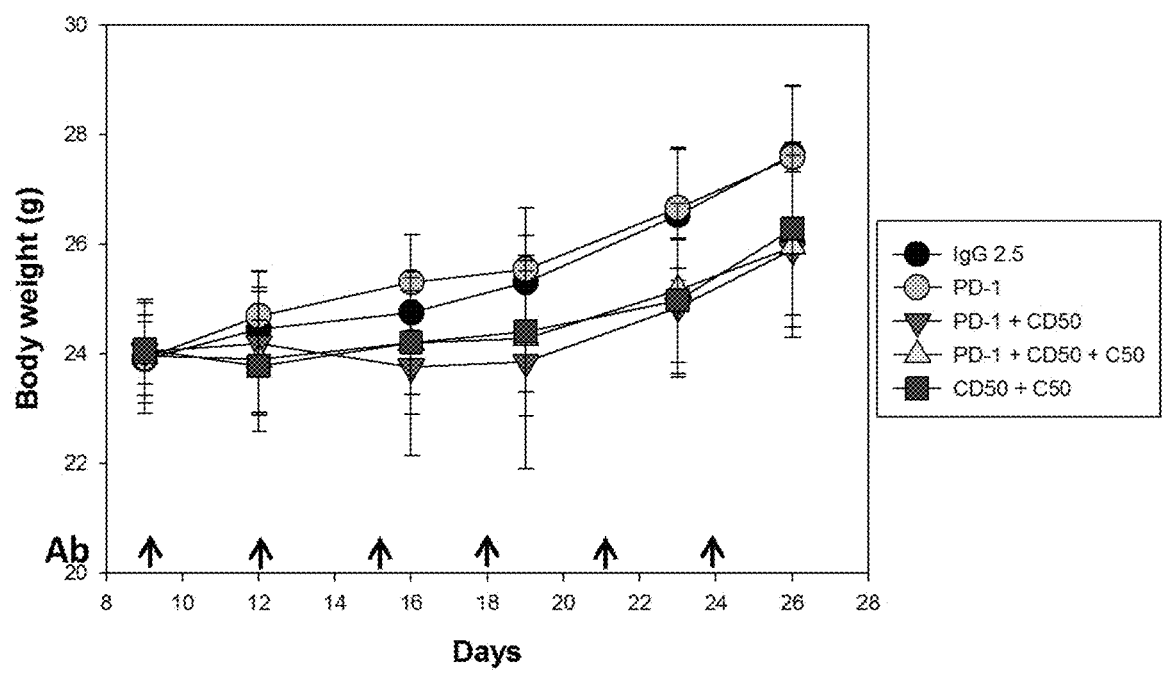
Figure 11D:
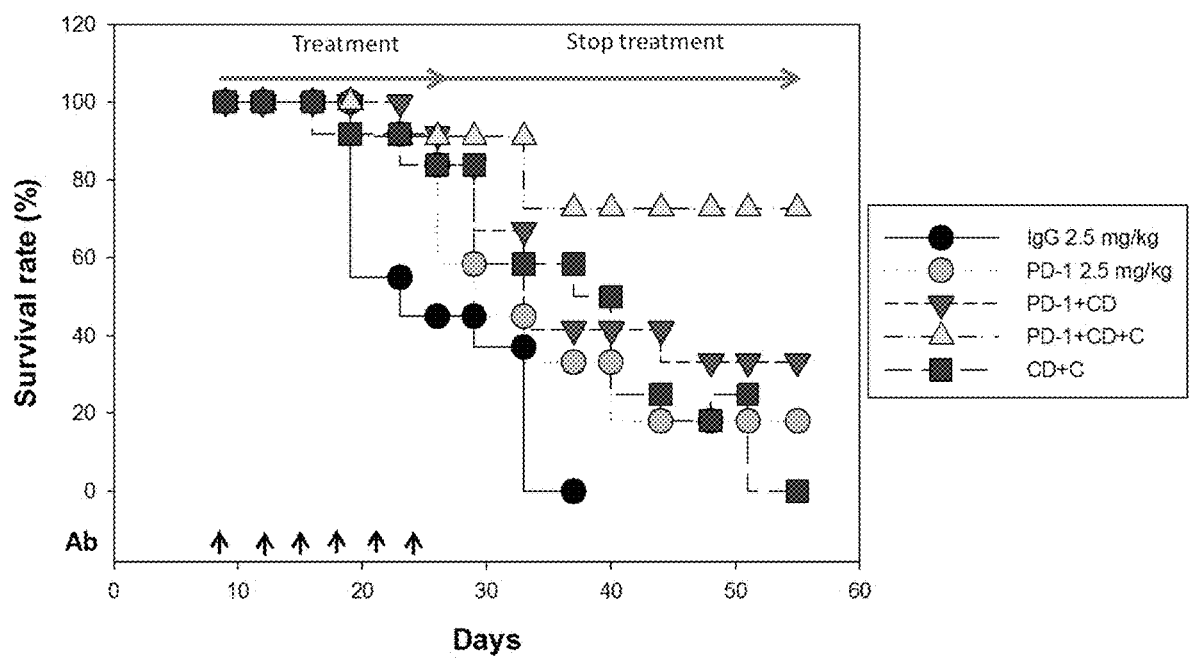

Example 11 to Confirm the Best Combination Regimen—Chidamide with Celecoxib Combined with Anti-PD-1 Antibody in CT26-Bearing Mice We evaluated the anti-cancer effect with more number of mice in each treatment group to confirm that chidamide and celecoxib combined with immune checkpoint inhibitor anti-PD-1 antibody regimen performed potent tumor inhibition in CT26-bearing mice. As shown in FIG. 11, the tumor size in the CT26-bearing mice grew to about 250-300 $mm^3$ at day 9. Combination chidamide plus celecoxib and anti-PD-1 antibody significantly inhibited tumor growth in the CT26-bearing mice (FIG. 11A). Combination chidamide 50 mg/kg plus anti-PD-1 antibody 2.5 mg/kg also significantly inhibited tumor growth in the CT26-bearing mice (FIG. 11A). A similar result was also indicated in combination chidamide 50 mg/kg plus celecoxib 50 mg/kg (FIG. 11A). However, chidamide 50 mg/kg plus celecoxib 50 mg/kg combined with the anti-PD-1 antibody 2.5 mg/kg is even more effective in inhibiting tumor growth in the CT26-bearing mice as compared to the other groups (FIG. 11A). These results suggested that chidamide plus celecoxib combined with immune checkpoint inhibitor performed strong anti-tumor ability in CT26-bearing mice model. The anti-cancer effects of various therapeutic modalities in all of the mice were shown in FIG. 11B. The anti-PD-1 antibody group only had slight anti-cancer activity and only three mouse achieved PR (response rate 25%). Combination chidamide plus celecoxib showed slight anti-cancer activity and only four mice achieved PR (response rate 33%). Combination chidamide plus anti-PD-1 antibody also showed improved anti-cancer activity and five mouse achieved PR (response rate 41%). Combination chidamide plus celecoxib and anti-PD-1 antibody showed the best anti-cancer activity and eight mice achieved PR (response rate 72%). As shown in FIG. 11C, none of the mice in the treatment groups lost any body weight. As shown in FIG. 11D, chidamide 50 mg/kg combined with anti-PD-1 antibody 2.5 mg/kg or anti-PD-1 Ab 2.5 mg/kg alone increased the survival rate to about 33% and 16%, respectively. However, Chidamide 50 mg/kg plus celecoxib 50 mg/kg combined with anti-PD-1 Ab 2.5 mg/kg regimen was again proven as powerful combinations for efficiently inhibiting tumor growth and increasing the survival rate to about 72% in the CT26-bearing tumor mice model. The regimen of chidamide combined with celecoxib in the absence of anti-PD-1 antibody did not improve survival rate compared to anti-IgG control regimen. The regimens in the absence of celecoxib only showed slight increase of survival rate. Taken together, these data demonstrated that chidamide plus celecoxib, combined with an immune checkpoint inhibitor, was a very potent and effective combination in inhibiting tumor growth and thus significantly increased survival rate in immunotherapy (FIG. 11D). This combination regimen may play an important role in improvement of T cell memory through synergistic mechanisms in the tumor microenvironment.

Figure 12A:
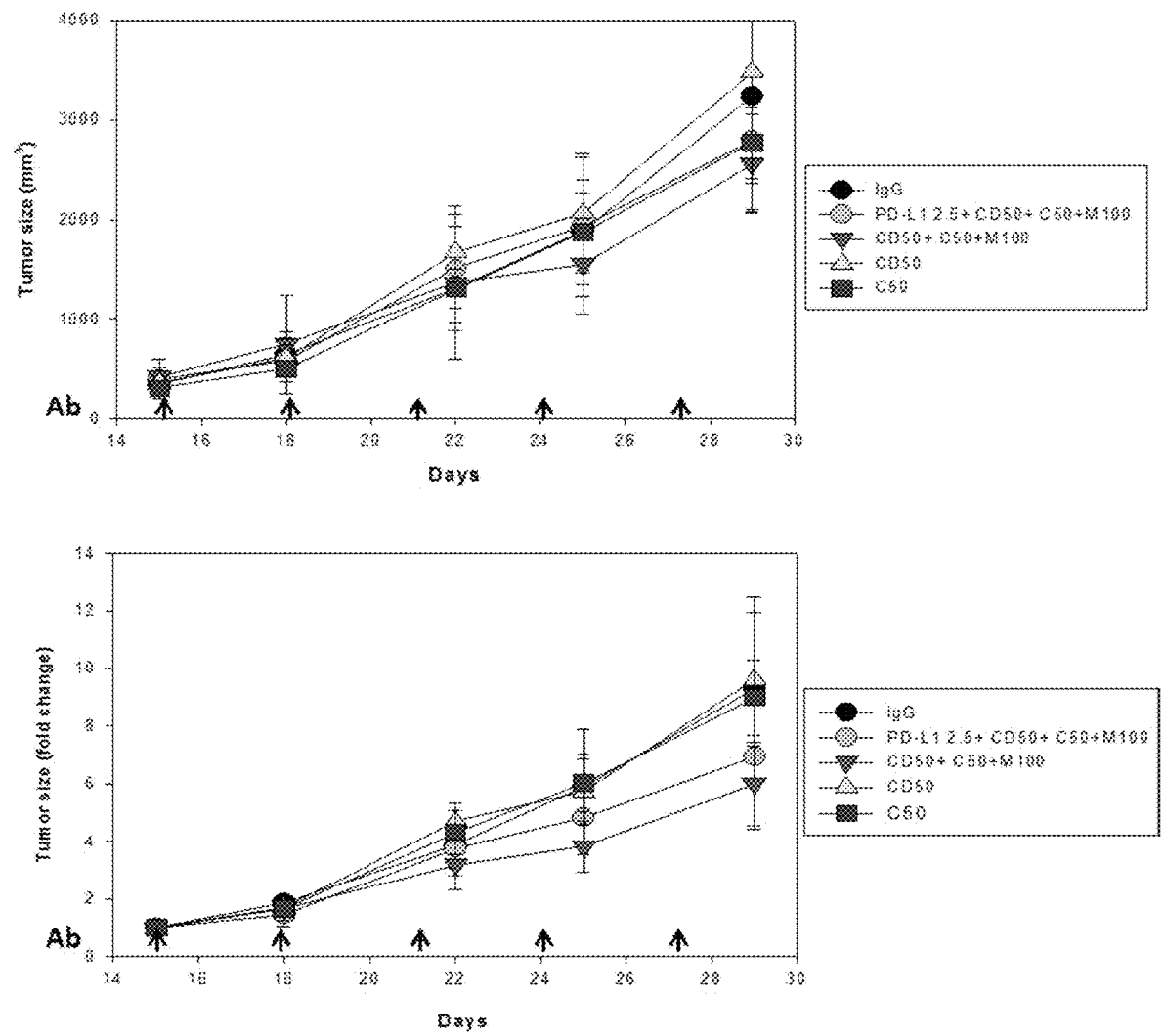
Figure 12B:
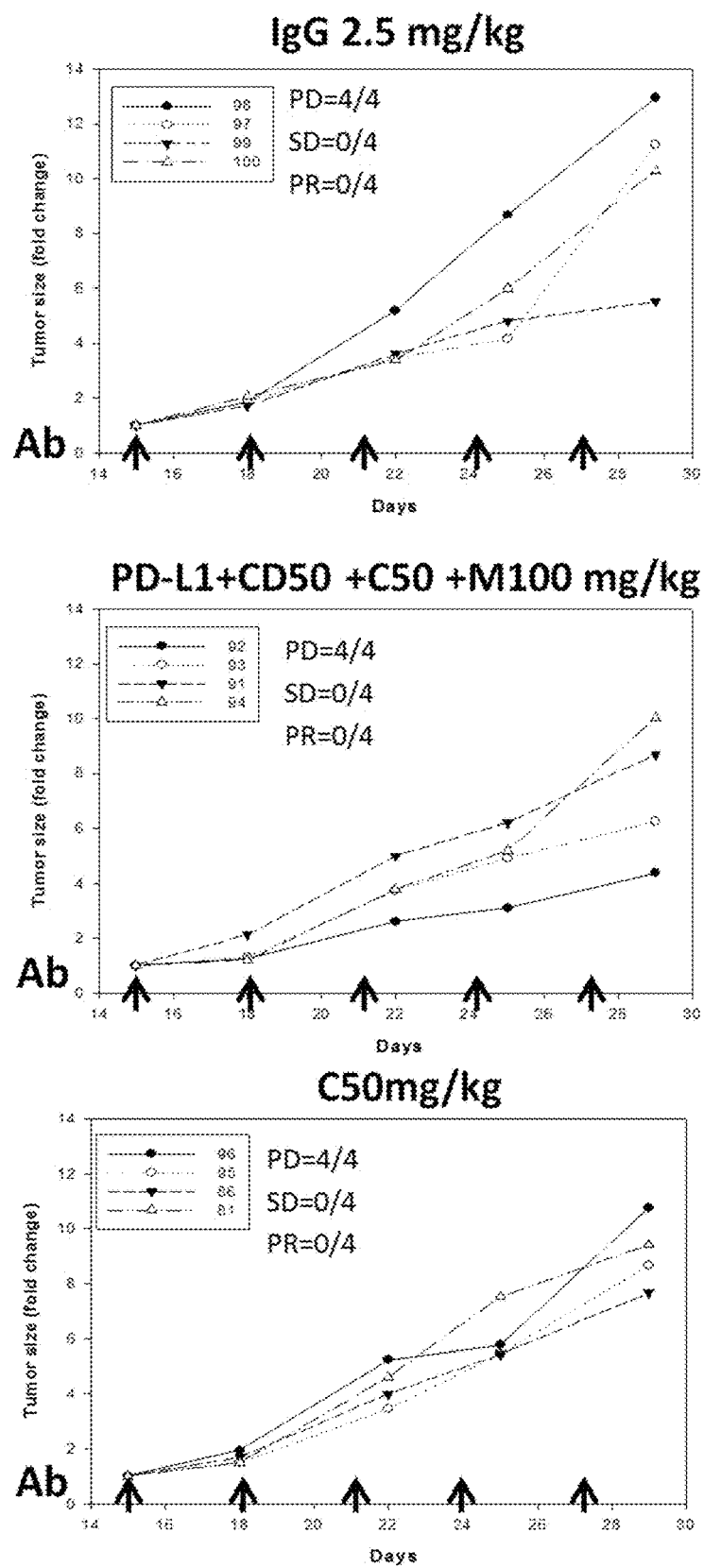
Figure 12B:
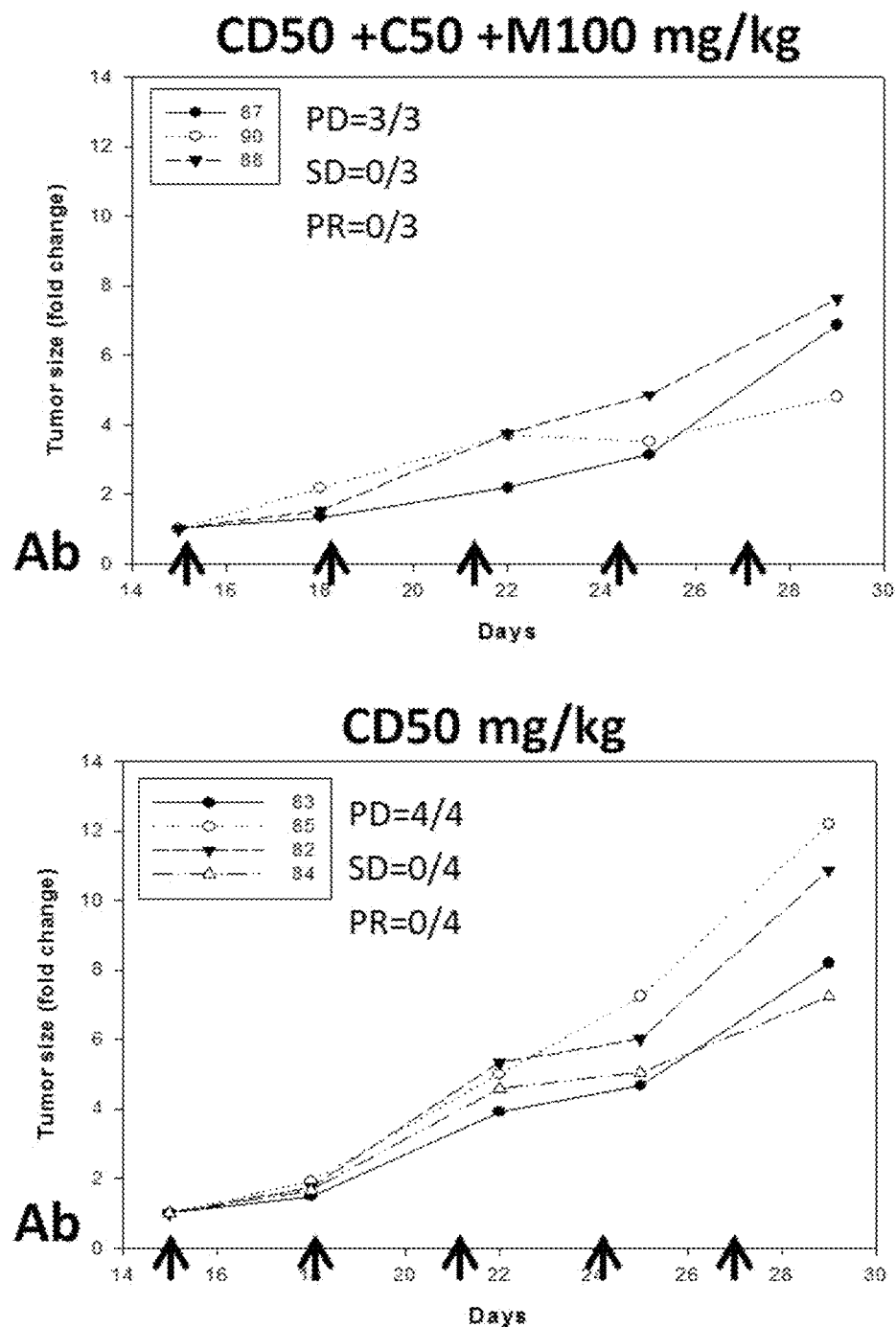
Figure 12C:
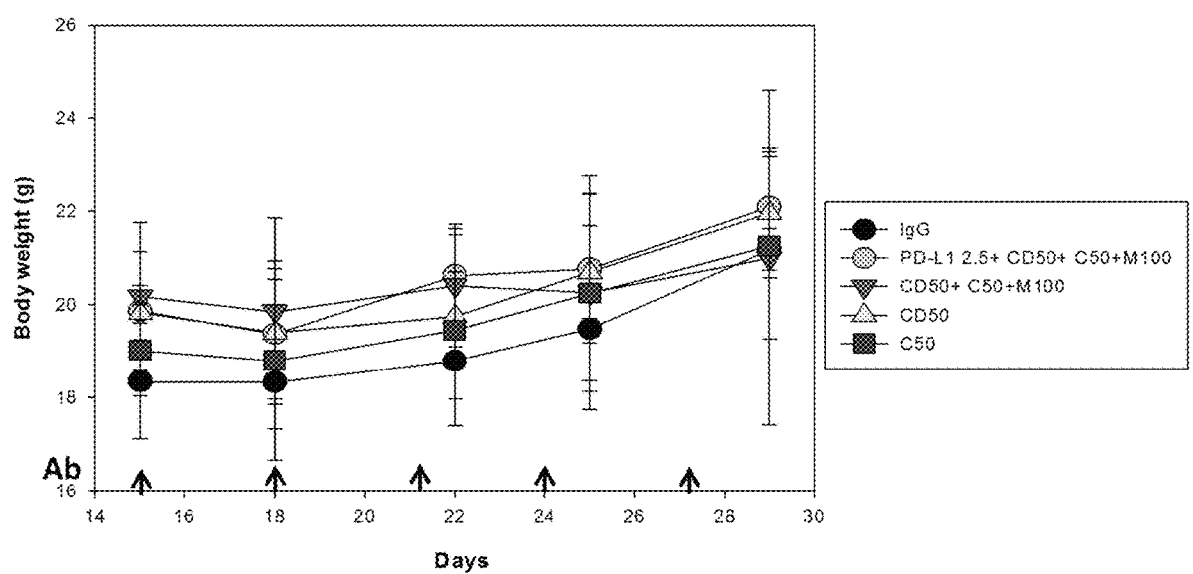
Figure 12D:
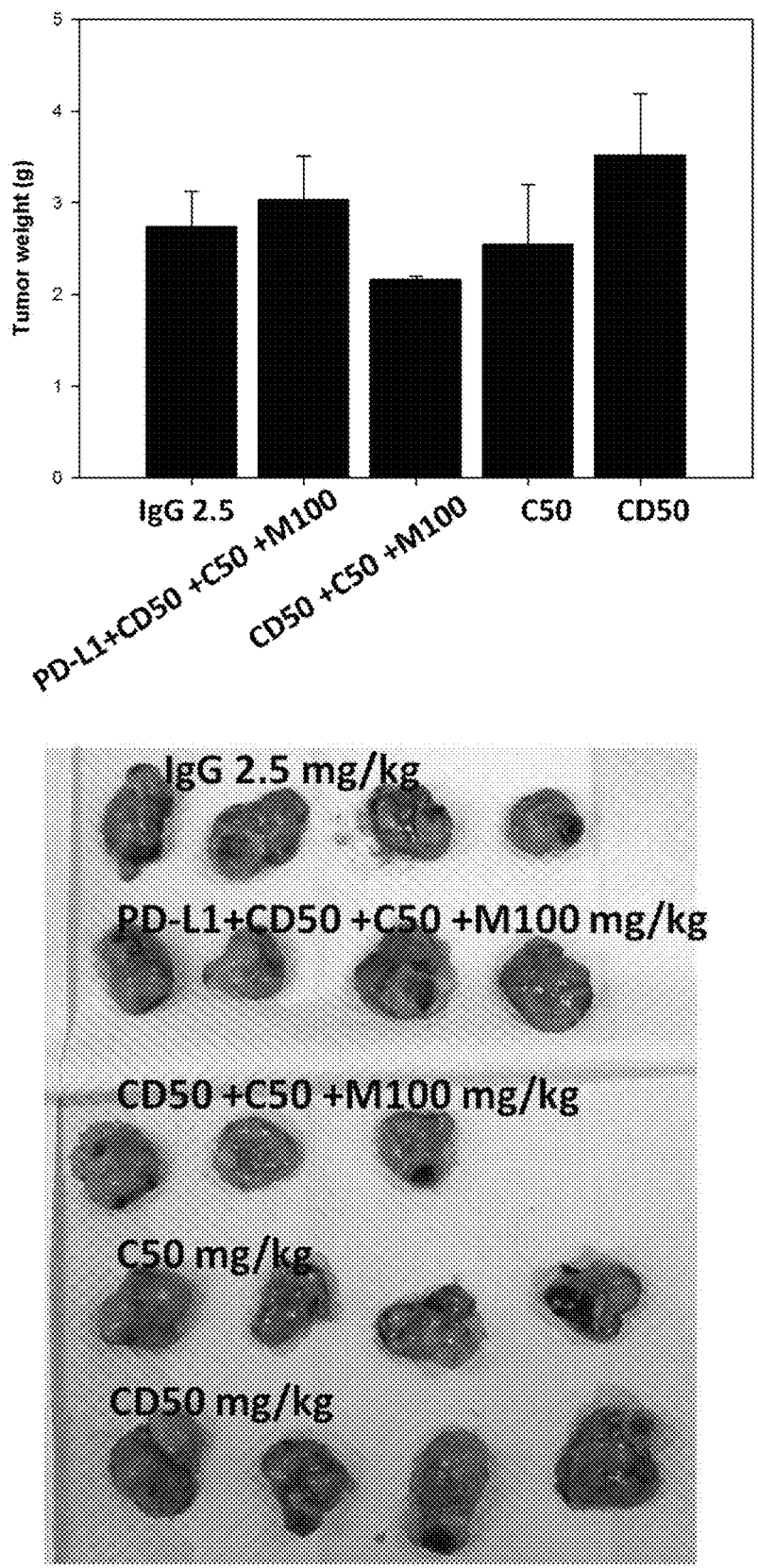
Figure 12E:
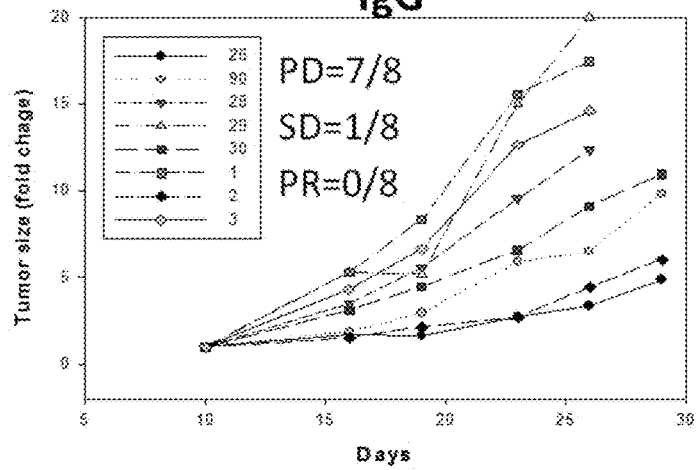
Figure 12E:
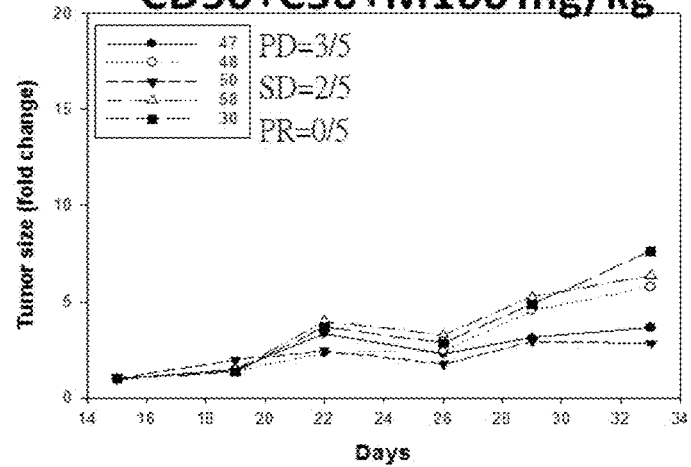
Figure 12E:
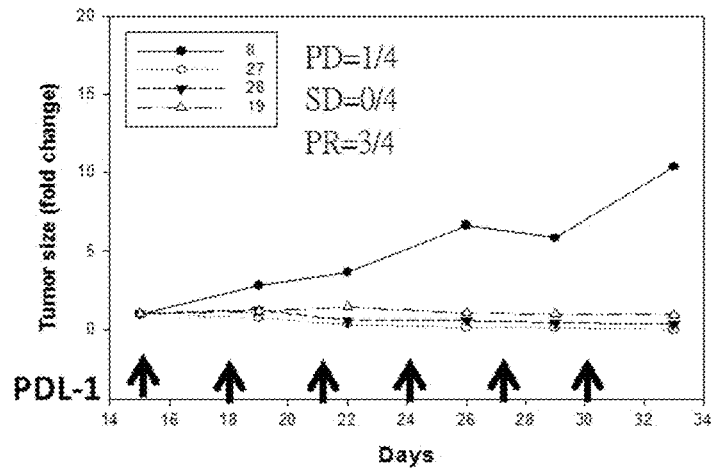
Figure 12E:
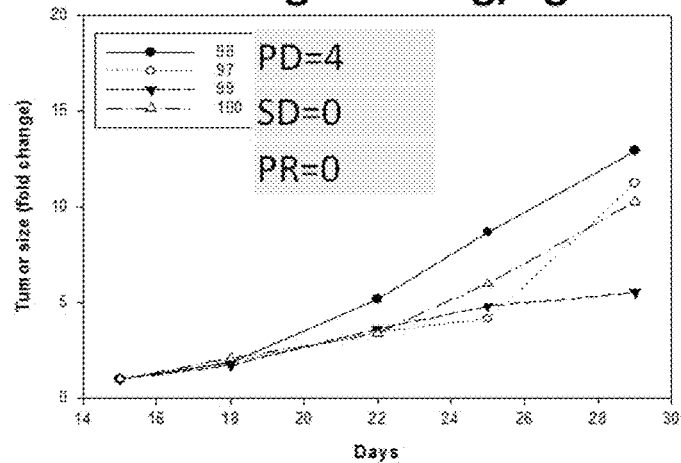
Figure 12E:
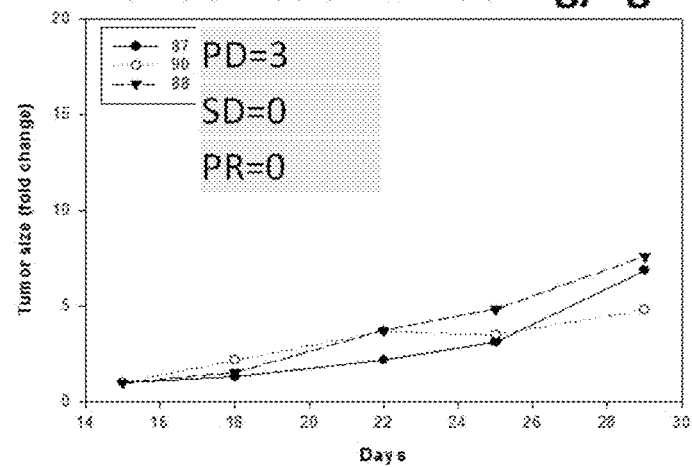
Figure 12E:
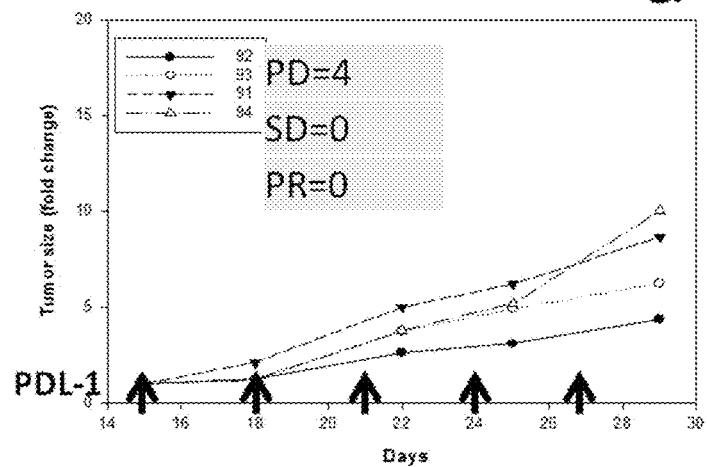

Example 12 to Clarify the Anti-Cancer Mechanisms of Chidamide Plus Metformin and Celecoxib Combined with Anti-PD-L1 Antibody by Using CT26-Bearing Nude Mice We were interested in evaluating whether chidamide plus metformin and celecoxib combined with anti-PD-L1 antibody performed tumor inhibition by activating cytotoxic T-lymphocytes in CT26-bearing mice (immunity normal status). So, we used an immunodeficient athymic nude mice (cytotoxic T-lymphocyte deficiency) animal model to test the theory. The nude mice were laboratory mice from a strain with genetic mutation that causes defective development of the thymus. It will cause significant decrease of T cells and lack of cell-mediated immunity. As shown in FIG. 12, the tumor size in the CT26-bearing nude mice grew to about 350-400 $mm^3$ at day 15. Several treatment groups were evaluated in anti-cancer effect. None of the groups efficiently inhibited tumor growth in the CT26-bearing nude mice model as shown in FIG. 12A. Chidamide 50 mg/kg plus metformin 100 mg/kg and celecoxib 50 mg/kg combined with or without anti-PD-L1 antibody 2.5 mg/kg regimens slightly possessed anti-cancer activity as compared to the other regimens. However, as shown in previous data, the same treatment regimens showed anti-cancer activity in CT26-bearing mice with normal immunity (wild type mice). These results suggested that normal immunity is required for strong anti-tumor ability of combination treatment with immune checkpoint inhibitor plus chidamide and celecoxib in the presence or absence of metformin in CT26-bearing mice model. The anti-cancer effects of various therapeutic modalities in all the mice were shown in FIG. 12B. None of the treatment groups showed PR response. These results demonstrated that all regimens could not perform significant anti-cancer activity in immune-defective nude mice. Chidamide plus celecoxib and metformin combined with or without anti-PD-L1 antibody regimens showed slight anti-cancer activity as compared to the other groups. As shown in FIG. 12C, none of the mice in the treatment groups lost any body weight. The tumor weight in the CT26-bearing nude mice grew to about 2.7-3.3 g at day 29 as shown in FIG. 12D. Only combination chidamide 50 mg/kg plus metformin 100 mg/kg and celecoxib 50 mg/kg showed slight inhibition of tumor growth based on the tumor weight, but no significant inhibition when based on the tumor size as shown in FIG. 12D. According to the results of this study compared with wild type BALB/c mice data (FIGS. 1-11), it was suggested that the anti-tumor activity of combination chidamide plus metformin and celecoxib combined with anti-PD-L1 or anti-PD-1 antibody required normal immunity (FIG. 12E). Therefore, these results support our proposal that combination therapy containing chidamide plus metformin and celecoxib combined with anti-PD-1/anti-PD-L1 has a synergistic anti-tumor effect to reactivate cytotoxic T-lymphocytes to kill cancer cells.

Taken together, these data demonstrated that chidamide plus celecoxib is a very important combination, efficiently controls the tumor microenvironment and possesses immunomodulating activity. When it was combined with immune checkpoint inhibitor such as anti-PD-1, anti-PD-L1 or anti-CTLA-4 antibody, it was more efficient in boosting anticancer activity and extending the survival in immunity-sufficient normal animal model. We can predict that chidamide plus celecoxib combined with immune checkpoint inhibitor will be significant in boosting the efficacy in immunotherapy for cancer patients.

Figure 13A:
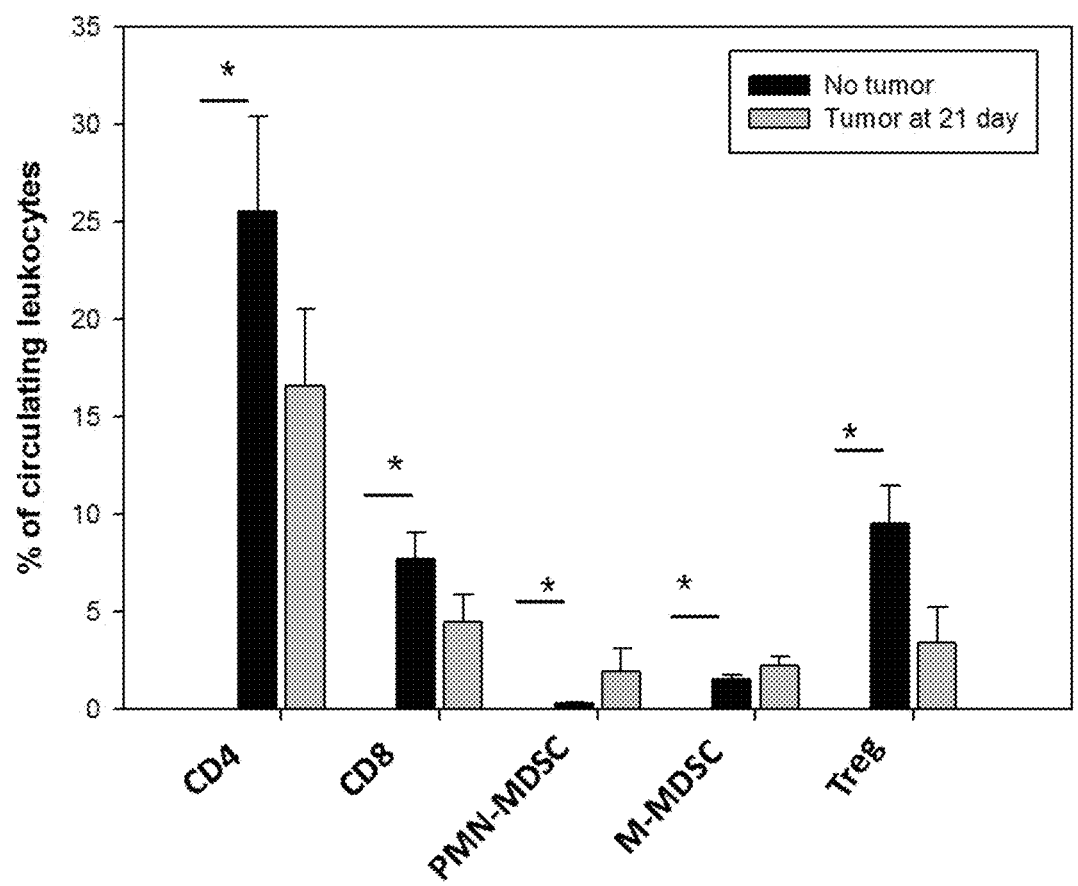
Figure 13B:
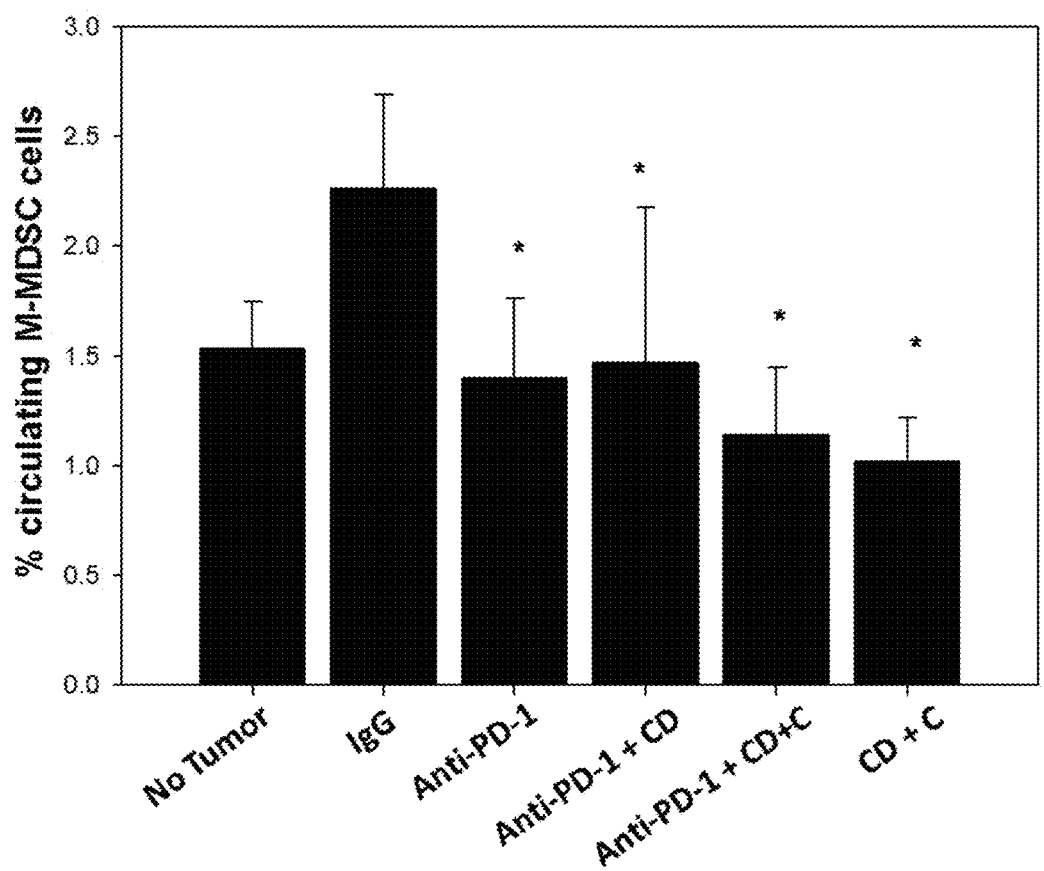
Figure 13C:
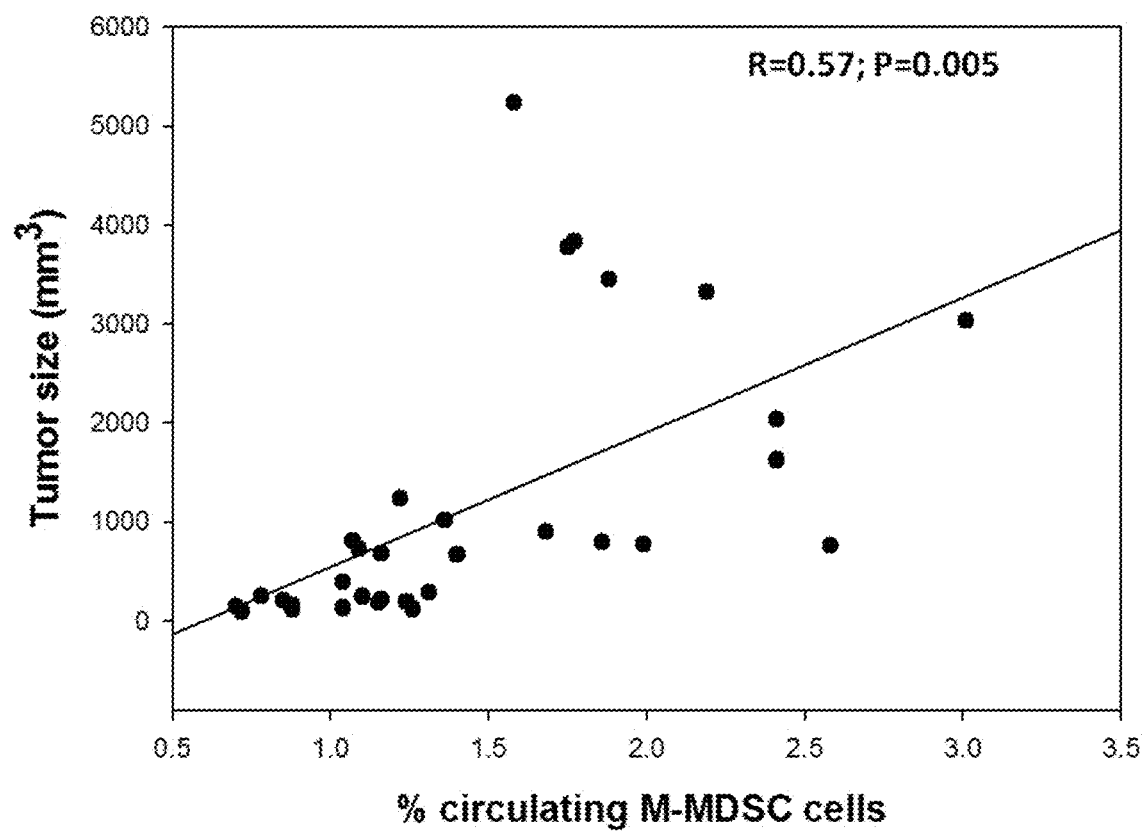
Figure 13D:
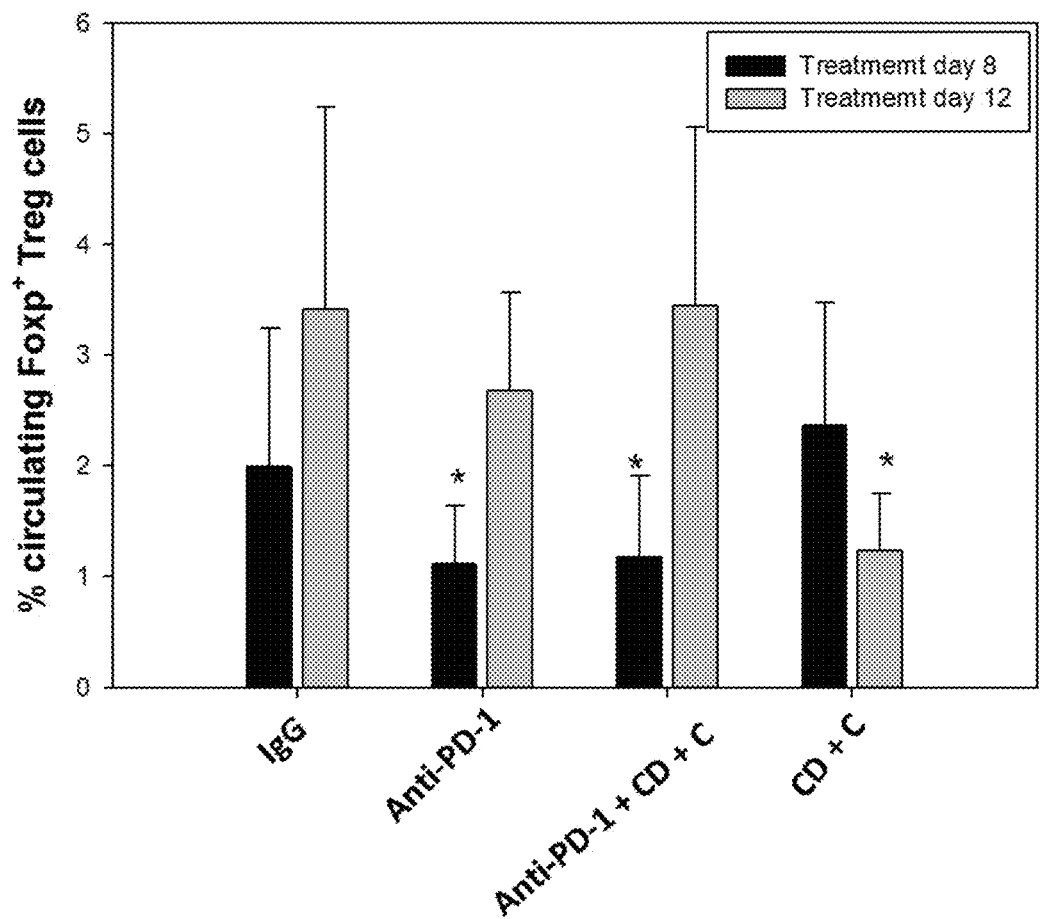
Figure 13E:
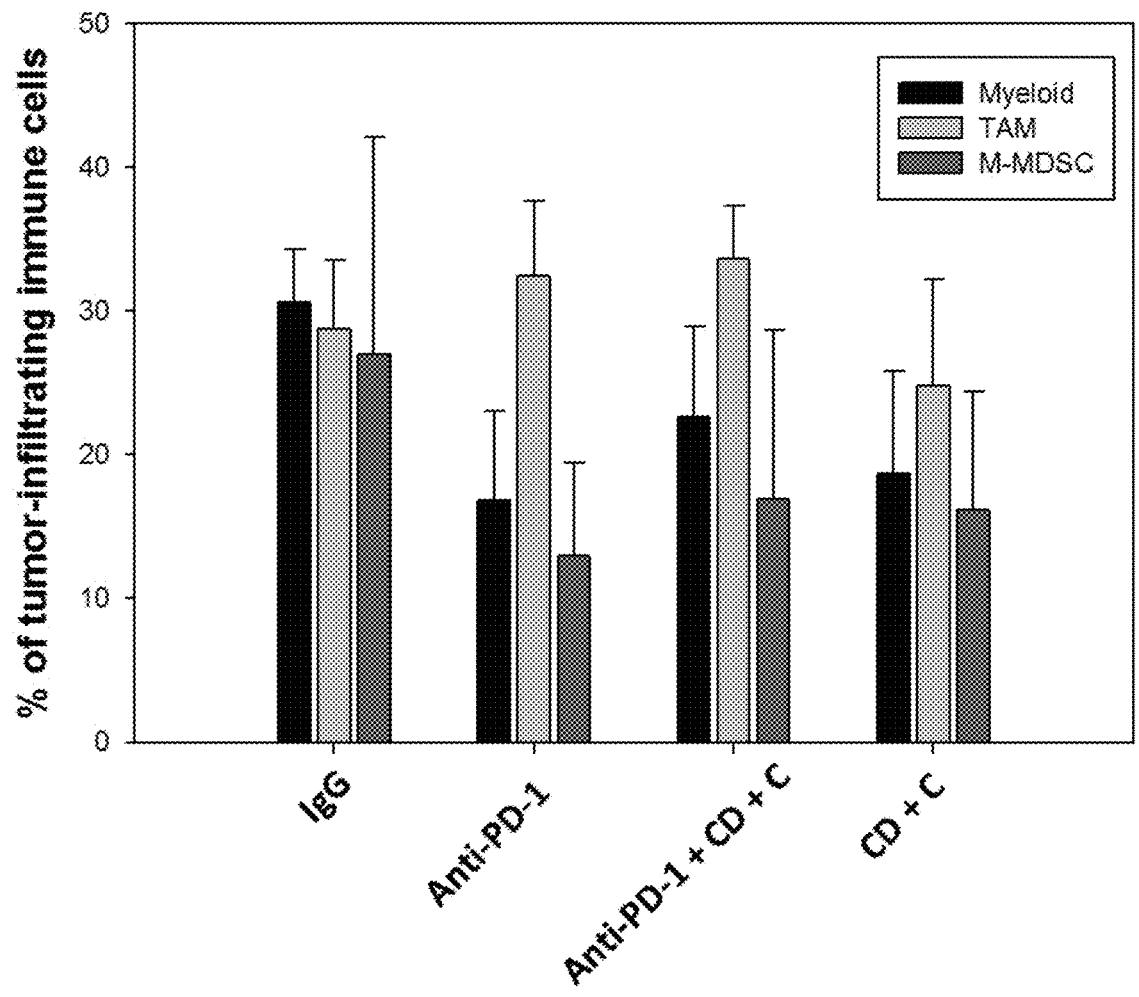
Figure 13F:
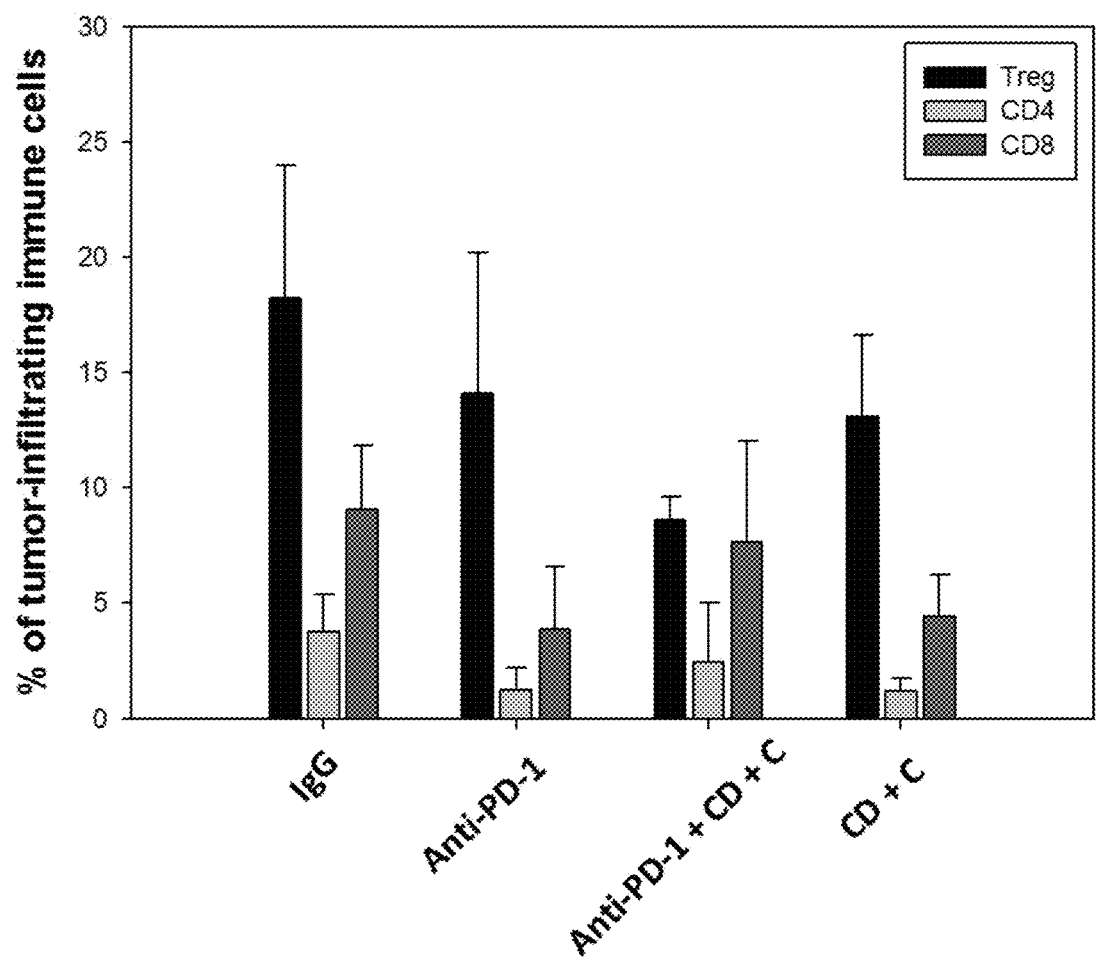
Figure 13G:
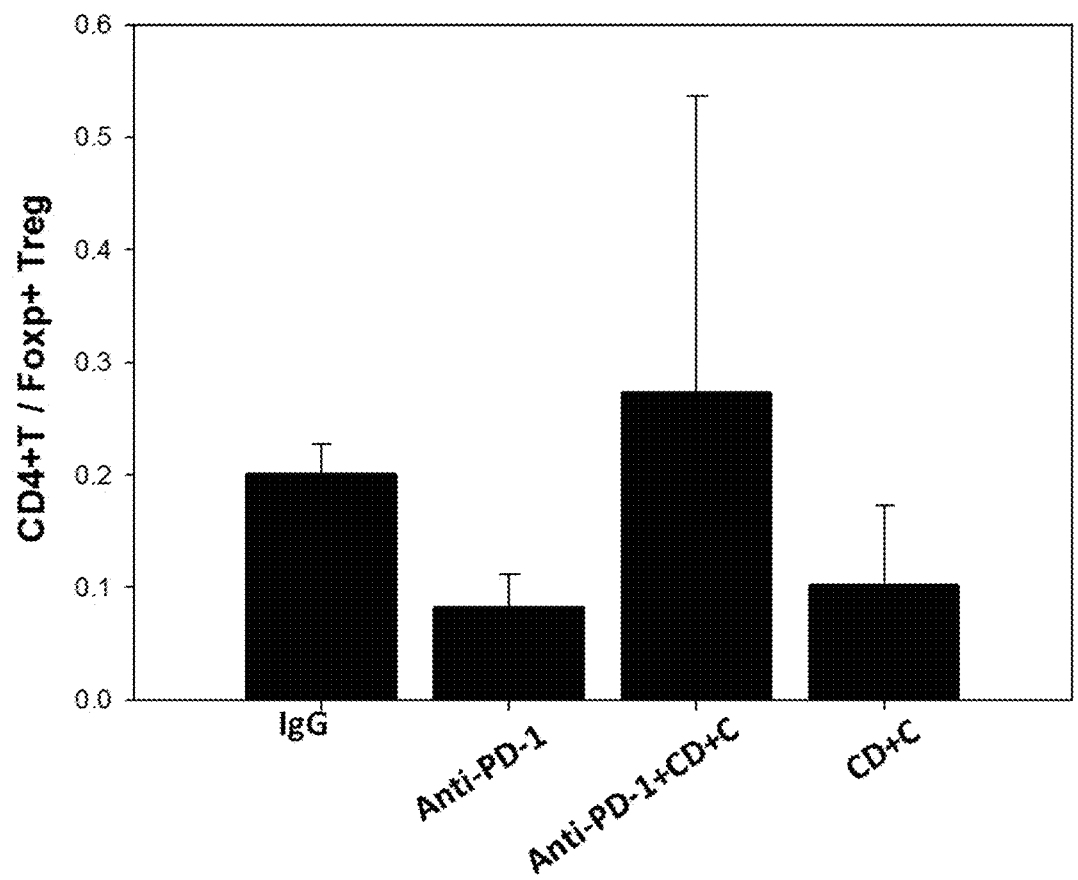
Figure 13H:
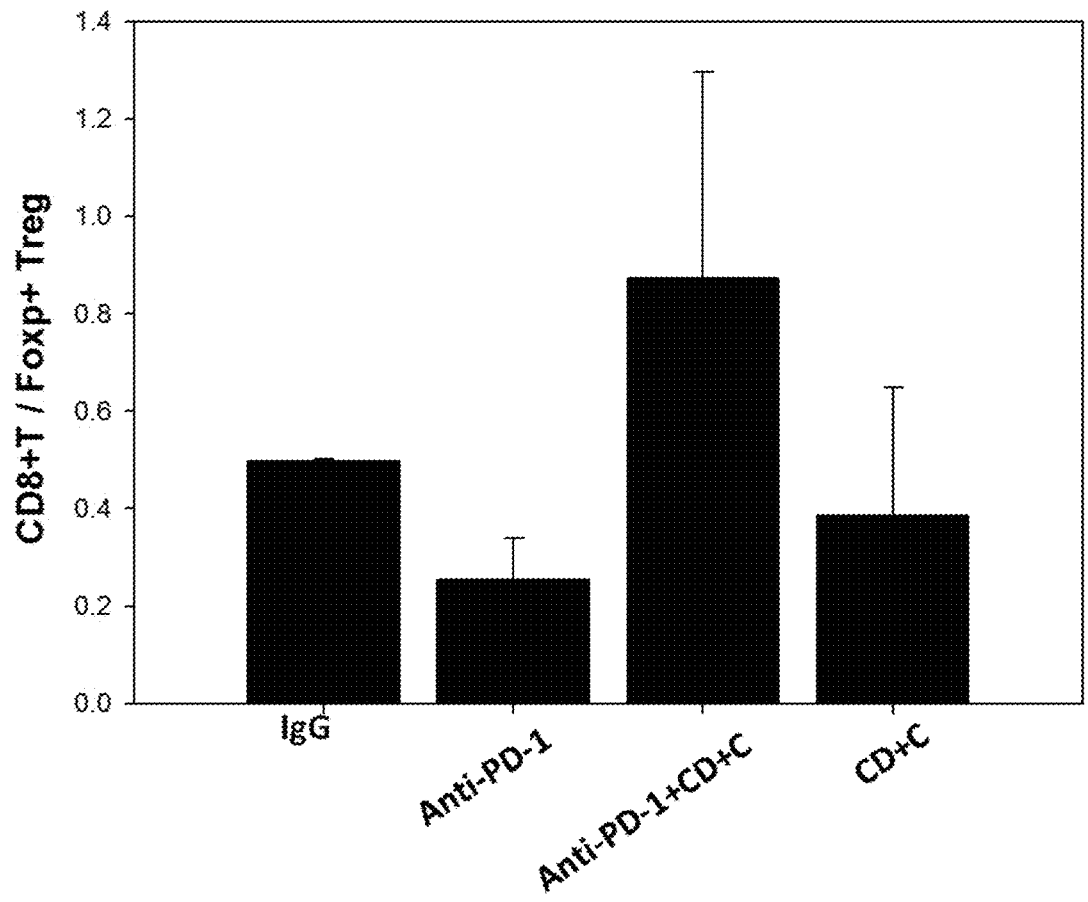

Example 13 to Analyze the Circulating and Tumor-Infiltrating Immune Cells after Treatment with Chidamide Plus Celecoxib Combined with Anti-PD-1 Antibody in CT26-Bearing BALB/c Mice We studied whether epigenetic modulator chidamide combined with a COX-2 inhibitor affected immune cell population in both blood circulation and tumor microenvironment. By using flow cytometry, we first analyzed the circulating immune cell population ($CD_4^+$ T cells, $CD_8^+$ T cells, PMN-MDSC and M-MDSC, and Treg cells) of normal mice (without tumor) and tumor-bearing mice. We found that in CT26 tumor-bearing mice there was a 4.7-fold increase in circulating granulocytic MDSCs (PMN-MDSCs; defined as $CD11b^+Ly6G^+Ly6C^{low}$) and 25% increase in circulating monocyte MDSC (M-MDSC; defined as $CD11b^+Ly6G^-Ly6C^+$) compared to normal mice (FIG. 13A). On the other hand, it was also found that $CD_4^+$ T cells, $CD_8^+$ T cells, and Treg cells were markedly decreased in tumor-bearing mice in comparison with normal mice as shown in FIG. 13A. MDSCs (myeloid-derived suppressor cells) are a heterogeneous population of cells that expands during cancer, inflammation, and infection and possess suppression of T cell functions. We focused the study on the effect of treatment regimens to M-MDSCs as indicated in FIG. 13B. Circulating M-MDSC cells were significantly increased in tumor-bearing mice without any treatment. However, it was significantly reduced by treatment with anti-PD-1 antibody alone or chidamide plus celecoxib or chidamide plus celecoxib combined with anti-PD-1 antibody. The treatment resulted in a striking reduction in the number of circulating M-MDSCs to a level similar to that observed in normal mice without any treatment (FIG. 13B). The result also demonstrated that cell number of PMN-MDSCs was not significantly changed by any treatment (data not shown). In addition, we analyzed circulating M-MDSC cells of tumor-bearing mice at day 12 and tumor size at day 23 after treatment as indicated in FIG. 13C. Results showed that cell number of circulating M-MDSCs at day 12 was significantly correlated with tumor size at day 23 after treatment. Other immune cells were not correlated with tumor size (data not shown). These results suggested that maybe circulating M-MDSC cells can be a predictor for tumor development in CT26 bear mice. On the other hand, we found that circulating Treg cells were significantly reduced by treatment with chidamide plus celecoxib with anti-PD-1 antibody at day 8 and chidamide plus celecoxib without anti-PD-1 antibody at day 12 (FIG. 13D). We next analyzed tumor-infiltrating immune cells. Treatment with anti-PD-1 antibody alone markedly reduced the number of myeloid cells and M-MDSC cells. Similar results were also shown in the groups of anti-PD-1 antibody combined with chidamide plus celecoxib or chidamide plus celecoxib as shown in FIG. 13E. The cell number of TAMs was not markedly changed by any treatment except the treatment with chidamide plus celecoxib. The cell number of Tregs was markedly reduced by treatment with anti-PD-1 antibody combined with chidamide plus celecoxib, and moderately reduced by treatment with anti-PD-1 antibody alone or chidamide plus celecoxib as shown in FIG. 13F. We found the ratio of $CD4^+$ T cells to Tregs slightly increased in the tumor tissues of the treatment group treated with combination of anti-PD-1 antibody with chidamide plus celecoxib compared to the other groups (FIG. 13G). This treatment group also showed higher ratio of $CD8^+$ T cells to Tregs than the other groups (FIG. 13H). Taken together, the treatment with chidamide plus celecoxib decreased tumor-infiltrating myeloid cells ($CD45^+CD11b^+$), M-MDSCs (FIG. 13E) and Tregs (FIG. 13F). These results suggested that chidamide plus celecoxib plays an important role in suppression of circulating and tumor-infiltrating suppressor cells, which subsequently contributes to anti-tumor activity in combination with anti-PD-1 antibody observed in CT26 tumor-bearing mice.

What is claimed is:

1. A method of removing immune suppression in a colorectal cancer tumor microenvironment or stimulating an immune system against colorectal cancer cells, comprising administering to a subject an HDAC inhibitor, an NSAID and an immune checkpoint inhibitor, wherein
    the HDAC inhibitor is selected from the group consisting of chidamide and entinostat;
    the NSAID is celecoxib; and
    the immune checkpoint inhibitor is anti-PD-1 antibody.
2. The method of claim 1, wherein the method can inhibit or treat colorectal cancer through immunotherapy.
3. The method of claim 1, wherein the combination further comprises a biguanide compound.
4. The method of claim 3, wherein the biguanide compound is metformin, phenformin, proguanil or chlorproguanil.
5. The method of claim 1, wherein the amounts of the HDAC inhibitor, the NSAID and the immune checkpoint inhibitor range from 10% (w/w) to 70% (w/w), 10% (w/w) to 70% (w/w) or 0.5% (w/w) to 20%, respectively.
6. The method of claim 3, wherein the amount of biguanide compound ranges from 30% to 70% (w/w).
7. The method of claim 1, which further comprises administering one or more additional anti-cancer agents.

* * * * *